US011326150B2

(12) United States Patent
Taniguchi et al.

(10) Patent No.: US 11,326,150 B2
(45) Date of Patent: May 10, 2022

(54) METHOD FOR PRODUCING TISSUE AND ORGAN

(71) Applicant: Public University Corporation Yokohama City University, Yokohama (JP)

(72) Inventors: Hideki Taniguchi, Yokohama (JP); Takanori Takebe, Yokohama (JP)

(73) Assignee: Public University Corporation Yokohama City University, Yokohama (JP)

( * ) Notice: Subject to any disclaimer, the term of this patent is extended or adjusted under 35 U.S.C. 154(b) by 0 days.

(21) Appl. No.: 14/347,482

(22) PCT Filed: Sep. 27, 2012

(86) PCT No.: PCT/JP2012/074840
§ 371 (c)(1),
(2) Date: Mar. 26, 2014

(87) PCT Pub. No.: WO2013/047639
PCT Pub. Date: Apr. 4, 2013

(65) Prior Publication Data
US 2014/0289877 A1 Sep. 25, 2014

(30) Foreign Application Priority Data

Sep. 27, 2011 (JP) .............................. JP2011-210157

(51) Int. Cl.
*C12N 5/071* (2010.01)
*A61K 35/407* (2015.01)
*A61K 35/12* (2015.01)
*A61L 27/38* (2006.01)
*A61L 27/54* (2006.01)
*A61K 35/28* (2015.01)
*A61K 35/44* (2015.01)
*A61K 35/39* (2015.01)
*A61K 35/545* (2015.01)
*A61K 49/00* (2006.01)

(52) U.S. Cl.
CPC ............ *C12N 5/0697* (2013.01); *A61K 35/12* (2013.01); *A61K 35/28* (2013.01); *A61K 35/39* (2013.01); *A61K 35/407* (2013.01); *A61K 35/44* (2013.01); *A61L 27/3804* (2013.01); *A61L 27/3808* (2013.01); *A61L 27/3834* (2013.01); *A61L 27/3886* (2013.01); *A61L 27/54* (2013.01); *C12N 5/0671* (2013.01); *C12N 5/0677* (2013.01); *A01K 2267/03* (2013.01); *A61K 35/545* (2013.01); *A61K 49/0008* (2013.01); *A61L 2300/412* (2013.01); *A61L 2300/414* (2013.01); *A61L 2430/26* (2013.01); *A61L 2430/28* (2013.01); *C12N 2501/115* (2013.01); *C12N 2501/12* (2013.01); *C12N 2501/155* (2013.01); *C12N 2501/16* (2013.01); *C12N 2502/1358* (2013.01); *C12N 2502/28* (2013.01); *C12N 2506/45* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| 2010/0021866 | A1 | 1/2010 | Tsuji et al. | |
| 2010/0041134 | A1* | 2/2010 | Forgacs | A61L 27/222 435/325 |
| 2010/0129771 | A1 | 5/2010 | Tsuji et al. | |
| 2010/0136114 | A1* | 6/2010 | Mao | A61K 35/44 424/486 |
| 2011/0171712 | A1* | 7/2011 | Rivron | C12N 5/0062 435/173.8 |

FOREIGN PATENT DOCUMENTS

| JP | 2005-229802 A | 9/2005 |
| WO | WO 2006/129672 A1 | 12/2006 |
| WO | WO 2008/105499 A1 | 9/2008 |
| WO | WO 2010/149597 A2 | 12/2010 |

OTHER PUBLICATIONS

Si-Tayeb et al., "Highly Efficient Generation of Human Hepatocyte-Like Cells from Induced Pluripotent Stem Cells", Hepatology, 2010, vol. 51, pp. 297-305.*
Gomez-Aristizabal et al., "Mesenchymal Stromal Cells as Supportive Cells for Hepatocytes", Molecular Therapy, 2009, vol. 17, No. 9, pp. 1504-1508.*
Pampaloni et al., "Three-Dimensional Cell Cultures In Toxicology", Biotechnology and Genetic Engineering Reviews, 2009, vol. 26, No. 1, pp. 117-138. (Year: 2009).*
Serban et al., "Effects of extracellular matrix analogues on primary human fibroblast behavior", Acta Biomaterialia, 2008, vol. 4, pp. 67-75. (Year: 2008).*
Chen et al., "Clonal analysis of nestin-vimentin+ multipotent fibroblasts isolated from human dermis", Journal of Science, 2007, vol. 120, pp. 2875-2883. (Year: 2007).*
Bonzo et al., "Human mesenchymal stem cells as a two-edged sword in hepatic regenerative medicine: engraftment and hepatocyte differentiation versus profibrogenic potential", Gut, 2008, 57(2), pp. 223-231. (Year: 2008).*
Johansson et al., "Formation of Composite Endothelial Cell-Mesenchymal Stem Cell Islets A Novel Approach to Promote Islet Revascularization", Diabetes, 2008, vol. 57, pp. 2393-2401. (Year: 2008).*

(Continued)

*Primary Examiner* — Laura Schuberg
(74) *Attorney, Agent, or Firm* — Morgan, Lewis & Bockius LLP

(57) ABSTRACT

The present invention provides a means for reconstituting tissues and organs having mature functions. A method of preparing a tissue or an organ, comprising coculturing an organ cell with a vascular endothelial cell and a mesenchymal cell, generating an organ bud, transplanting the organ bud into a non-human animal, and then isolating from the non-human animal the transplanted organ bud-derived tissue or organ.

16 Claims, 33 Drawing Sheets

(56) References Cited

OTHER PUBLICATIONS

Eiraku et al., "Self-organizing optic-cup morphogenesis in three-dimensional culture," Nature (Apr. 7, 2011), vol. 472, pp. 51-56.
Extended European Search Report issued in European Patent Application No. 12835199.6 dated Apr. 17, 2015.
Matsumoto et al., "Liver Organogenesis Promoted by Endothelial Cells Prior to Vascular Function", Science, vol. 294 (2001) pp. 559-563.
Mcguigan et al., "Vascularized organoid engineered by modular assembly enables blood perfusion", Proceedings of the National Academy of Sciences, vol. 103, No. 31 (2006) pp. 11461-11466.
Nahmias et al., "Endothelium-Mediated Hepatocyte Recruitment in the Establishment of Liver-like Tissue In Vitro", Tissue Engineering, vol. 12, No. 6 (2006) pp. 1627-1638.
Takebe et al., "Generation of a vascularized and functional human liver from an iPSC-derived organ bud transplant", Nature Protocols, vol. 9, No. 2 (2014) pp. 396-409.
Takebe et al., "Vascularized and functional human liver from an iPSC-derived organ bud transplant", Nature, vol. 000 (2013) pp. 1-5.
International Search Report, dated Jan. 15, 2013, issued in PCT/JP2012/074840.
Lee et al., "Enhanced liver-specific functions of endothelial cell-covered hepatocyte hetero-spheroids", Biochemical Engineering Journal vol. 20, pp. 181-187, 2004.
Rouwkema et al., "The use of Endothelial Progenitor Cells for Prevascularized Bone Tissue Engineering", Tissue Ingineering: Part A, vol. 15, No. 8, pp. 2015-2027, 2009.
Takebe et al., "Generation of Functional Human Vascular Network", Transplantation Proceedings, vol. 44, No. 4, pp. 1130-1133, 2012.
Takebe et al., "Self-Organization of Human Hepatic Organoid by Recapitulating Organogenesis In Vitro", Transplantation Proceedings, vol. 44, No. 4, pp. 1018-1020, 2012.
Verseijden et al., "Adult Human Bone Marrow- and Adipose Tissue-Derived Stromal Cells Support the Formation of Prevascular-like Structures from Endothelial Cells in Vitro", Tissue Engineering: Part A, vol. 16, No. 1, pp. 101-114, 2010.
Yagi et al., "Buta Datsu Saiboka Gijutsu to Kan'yokei Kansaibo no Yugo ni yori Sanjigen Kekkan Kozo o Yusu Shinki Ishoku Kanzo no Kaihatsu", Regenerative Medicine, vol. 10, p. 270, 2P-117, Feb. 1, 2011.
English translation of International Preliminary Report on Patentability dated Mar. 27, 2014, in PCT International Application No. PCT/JP2012/074840.
European Office Action issued in European Patent Application No. 12 835 199.6 dated Jul. 3, 2017.
Saito et al., "Transplantation of Liver Organoids in the Omentum and Kidney", Artificial Organs, vol. 35, No. 1 (2010) pp. 80-83.

* cited by examiner

METHOD FOR PRODUCING TISSUE AND ORGAN

TECHNICAL FIELD

The present invention relates to methods of preparing organ buds, tissues and organs from undifferentiated cells such as induced pluripotent stem cells (iPS cells).

BACKGROUND ART

Recently, methods of generating human functional cells useful for drug discovery screening and regenerative medicine by directed differentiation from pluripotent stem cells (such as iPS cells) having capacity to differentiate into various functional cells have attracted a great deal of attention. To date, many attempts have been made to differentiate pluripotent stem cells into various types of functional cells by adding a variety of inducing factors to culture systems (M. Schuldiner, et al. PNAS, 97(21), 11307-11312 (2000); K. Si-Taiyeb, et al. Hepatology, 51 (1): 297-305 (2010)). However, conventional methods of directed differentiation in which three-dimensional tissue structures are not reconstituted have the following big problems: difficulty in inducing the terminal differentiation of functional cells, low efficiency in directed differentiation and poor reproducibility.

On the other hand, in clinical practice, organ transplantation and replacement with artificial organs are carried out to treat severe organ failures. However, organ transplantations are confronted with rejections and critical shortage of donors; and artificial organs are only capable of replacing a part of the required function for a short period of time (Japanese Unexamined Patent Publication No. Hei 9-56814; Japanese Unexamined Patent Publication No. 2004-166717). Thus, both methods have fundamental problems to be solved. With respect to artificial generation of human tissues, though a method in which terminally differentiated cells are seeded on a support (scaffolding) has been designed, no technique has been ever established for creating an organ with complex higher functions such as liver (Non-Patent Document No. 1). Briefly, a method of reconstituting a human tissue or organ having a well-ordered three-dimensional structure composed of a plurality of cell lineages as seen in adult tissues has not been established yet.

PRIOR ART LITERATURE

Patent Documents

Patent Document No. 1: Japanese Unexamined Patent Publication No. Hei 9-56814
Patent Document No. 2: Japanese Unexamined Patent Publication No. 2004-166717

Non-Patent Documents

Non-Patent Document No. 1: Uygun, B. E., et al. Nat Med, 16(7), 814-820 (2010)

DISCLOSURE OF THE INVENTION

Problem for Solution by the Invention

Conventional methods of directed differentiation using pluripotent stem cells are attempts to induce cell differentiation with a various combination of differentiation factors such as addition of humoral factors, gene transfer, etc. However, with these conventional methods, it is impossible to induce terminally differentiated functional cells. Furthermore, even the induction of early differentiation into tissue stem cells (i.e., progenitor populations of functional cells) has not been sufficiently achieved by those methods.

On the other hand, cells constituting tissues and organs comprise not only functional cells but also a plurality of cell species such as vascular cells and mesenchymal cells. Such cells take an orderly spatial arrangement, which generates coordinate interactions. As a result, a tissue structure is formed. However, at present, only a method using a support such as scaffolding is available as a technique to reconstitute human tissues and organs. This method has the following problems. Seeded functional cells have an extremely low engraft rate, and long-term culture of them is difficult. Further, the function of reconstituted tissue/organ is extremely immature.

It is an object of the present invention to solve the above-described problems and to provide the means to reconstitute tissues and organs having mature functions.

Means to Solve the Problem

For solving the above-described problems, the present inventors believe that it is essential to induce cell differentiation and morphogenesis simultaneously by precisely recapitulating processes of organogenesis. Briefly, it is extremely important to develop a novel method for reconstituting a three-dimensional tissue structure in which different cell lineages are arranged well spatiotemporally. In the present invention, the inventors have attempted to develop a technique for reconstituting three-dimensional tissues and organs by an approach of recapitulating the interactions among a plurality of cells generated in organogenesis.

During physiological organogenesis processes, organogenesis accompanied by autonomous constitution of tissue structures and cell differentiation progresses through close interactions of organ cells with vascular endothelial cells and undifferentiated mesenchymal cells.

The present invention intends to artificially generate organ buds (that become a starting material for tissues and organs in vitro) by artificially recapitulating those early processes of organogenesis to thereby direct early differentiation via interactions among a plurality of cell lineages and induce the histogenetic capacity of those organ cells which achieved early differentiation. Further, the present invention intends to generate tissues and organs which are composed of terminally differentiated functional cells and vascular networks by transplanting those organ buds induced in culture systems into living bodies so as to initiate blood flow.

Specifically, organ cells at an optimal differentiation stage as obtained from pluripotent stem cells such as iPS cells are cocultured with vascular endothelial cells and mesenchymal cells. These three different cell components may preferably be cultured at an optimal mixture ratio. When these cells are cultured for a short time in a differentiation-inducing medium containing specific nutritional factors and humoral factors under special circumstances where cells are supported by extracellular matrix components, it becomes possible to induce three-dimensional organ buds with microvasculature in vitro. Further, by transplanting those organ buds induced in culture systems into a living body and initiating blood flow by promoting vascularization, it becomes possible to generate tissues and organs which have a highly ordered tissue structure comparable to that of adult tissues. The inventors believe that either one or both of vascular endothelial cells and mesenchymal cells may be replaced by a substance such as a factor secreted from vascular endothelial cells, a factor secreted from mesenchymal cells, or a factor secreted as a result of the presence of both vascular endothelial cells and mesenchymal cells.

Such a technique which focuses on interactions among a plurality of cells and attempts three-dimensional reconstitution of tissues and organs has not existed to date. It is believed to be a method of extremely high novelty.

A summary of the present invention is as described below.

(1) A method of preparing an organ bud, comprising culturing an organ cell together with at least one cell and/or factor selected from the group consisting of vascular endothelial cells, mesenchymal cells, factors secreted from vascular endothelial cells, factors secreted from mesenchymal cells, and factors secreted as a result of the presence of both vascular endothelial cells and mesenchymal cells.

(2) The method of (1) above, wherein the organ cell is a differentiated cell.

(3) The method of (1) above, wherein the organ cell is an undifferentiated cell.

(4) The method of any one of (1) to (3) above, wherein the organ cell is a cell of an endodermal organ or a cell capable of differentiating thereinto, a cell of a mesodermal organ or a cell capable of differentiating thereinto, or a cell of an ectodermal organ or a cell capable of differentiating thereinto.

(5) The method of (4) above, wherein the organ cell is a cell of an endodermal organ or a cell capable of differentiating thereinto.

(6) The method of (5) above, wherein the endodermal organ is liver or pancreas.

(7) The method of any one of (1) to (6) above, wherein the organ cell is an induced pluripotent stem cell-derived cell.

(8) The method of (7) above, wherein the induced pluripotent stem cell is derived from human.

(9) The method of any one of (1) to (8) above, wherein the organ cell is cultured in a medium for culturing vascular endothelial cells, together with at least one cell and/or factor selected from the group consisting of vascular endothelial cells, mesenchymal cells, factors secreted from vascular endothelial cells, factors secreted from mesenchymal cells, and factors secreted as a result of the presence of both vascular endothelial cells and mesenchymal cells.

(10) The method of any one of (1) to (9) above, wherein the organ cell is plated on a gel and cultured together with at least one cell and/or factor selected from the group consisting of vascular endothelial cells, mesenchymal cells, factors secreted from vascular endothelial cells, factors secreted from mesenchymal cells, and factors secreted as a result of the presence of both vascular endothelial cells and mesenchymal cells.

(11) The method of any one of (1) to (10) above, wherein the vascular endothelial cell is a differentiated cell.

(12) The method of any one of (1) to (10) above, wherein the vascular endothelial cell is an undifferentiated cell.

(13) The method of any one of (1) to (12) above, wherein the mesenchymal cell is a differentiated cell.

(14) The method of any one of (1) to (12) above, wherein the mesenchymal cell is an undifferentiated cell.

(15) A method of preparing a tissue or an organ, comprising transplanting the organ bud prepared by the method of any one of (1) to (14) above into a non-human animal and differentiating the organ bud into a tissue or an organ.

(16) A method of transplanting an organ bud, comprising transplanting the organ bud prepared by the method of any one of (1) to (14) above into a human or a non-human animal.

(17) The method of (16) above, wherein the site of transplantation of the organ bud is selected from the group consisting of the intracranial space, the mesentery, the liver, the spleen, the kidney, the kidney subcapsular space, and the supraportal space.

(18) A method of regeneration or function recovery of a tissue or an organ, comprising transplanting the organ bud prepared by the method of any one of (1) to (14) above into a human or a non-human animal and differentiating the organ bud into a tissue or an organ.

(19) A method of preparing a non-human chimeric animal, comprising transplanting the organ bud prepared by the method of any one of (1) to (14) above into a non-human animal and differentiating the organ bud into a tissue or an organ.

(20) A method of evaluating a drug, comprising using at least one member selected from the group consisting of the organ bud prepared by the method of any one of (1) to (14) above, the tissue or organ prepared by the method of (15) above, and the non-human chimeric animal prepared by the method of (19) above.

Effect of the Invention

Conventionally, functional cells obtained from pluripotent stem cells by directed differentiation remained at an immature differentiation stage, compared to those functional cells that constitute biological tissues. This is because terminal differentiation of functional cells has not been achieved by the conventional directed differentiation method. According to the present invention, establishment of a method of inducing terminal differentiation of human functional cells based on reconstitution of three-dimensional structures is expected (for example, reconstitution of cell polarity against vasculature). This method is highly valuable as a technique for generating human functional cells.

Further, in conventional directed differentiation methods for pluripotent stem cells, it has been totally impossible to obtain tissue stem cells. When generation of tissue stem cells from iPS cells is achieved according to the present invention, the human liver stem cell manipulation technique developed by the present inventors in the past (WO/2009/139419) may potentially be combined with this accomplishment to provide a cell manipulation technique useful for mass generation of human liver cells.

Further, in the present invention, it is possible to reconstitute three-dimensional human tissue structures with vascular networks by artificially recapitulating the interactions among a plurality of cells generated in organogenesis. Therefore, the method of the present invention is expected to become a basic technique for generating human tissues and organs with blood flow through appropriately arranged vascular networks; generation of such tissues or organs has never been achieved by conventional techniques.

The present specification encompasses the contents disclosed in the specification and/or drawings of Japanese Patent Application No. 2011-210157 based on which the present application claims priority.

BEST MODES FOR CARRYING OUT THE INVENTION

Figure 1:
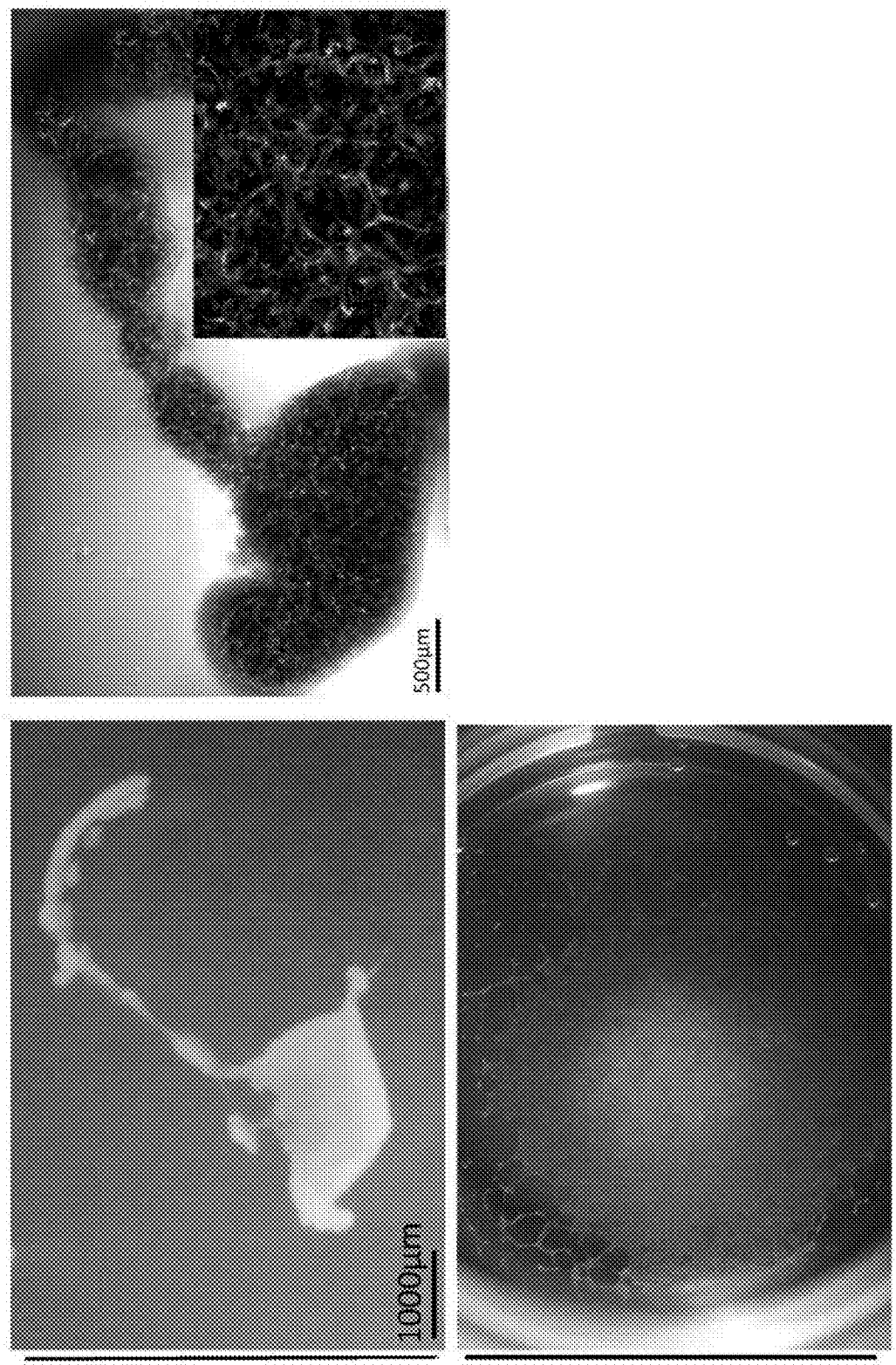
FIG. 1 This figure shows autonomous organization of human iPS cell-derived hepatic endoderm cells. Lower left panel shows human hepatic endoderm cells. Upper left panel shows a three-dimensional structure (liver bud) formed by coculture of three cell lineages of hepatic endoderm cells, vascular endothelial cells and undifferentiated mesenchymal cells (at day 4 of culturing). Upper right panel is a fluorescence microscopic photograph of the above-described three-dimensional structure. Vascular endothelial cells (HUVECs) are labeled with EGFP and undifferentiated mesenchymal cells (hMSCs) are labeled with KO but iPS cells are not labeled.

Hereinbelow, the present invention will be described in detail.

The method of preparing an organ bud of the present invention is characterized by culturing an organ cell together with at least one cell and/or factor selected from the group consisting of vascular endothelial cells, mesenchymal cells, factors secreted from vascular endothelial cells, factors secreted from mesenchymal cells, and factors secreted as a result of the presence of both vascular endothelial cells and mesenchymal cells.

In the present invention, the term "organ bud" means a structure capable of differentiating into an organ through maturing, the structure comprising three types of cells which are organ cells, vascular endothelial cells and undifferentiated mesenchymal cells or cells differentiated therefrom. Whether a structure is an organ bud or not can be judged, for example, by transplanting the structure into an organism and examining whether or not it is capable of differentiating into an organ of interest (the structure can be judged as organ bud if it has differentiated into the organ of interest); and/or by examining whether or not the structure comprises all of the above-described three types of cells (the structure can be judged as organ bud if it comprises all of the three types of cells). The organ bud may be one which differentiates into an organ such as kidney, heart, lung, spleen, esophagus, stomach, thyroid, parathyroid, thymus, gonad, brain, spinal cord or the like. Preferably, the organ bud is one which differentiates into an endodermal organ such as one which differentiates into liver (liver bud), one which differentiates into pancreas (pancreas bud), or one which differentiates into intestinal tract. Whether an organ bud is one which differentiates into an endodermal organ or not can be judged by examining the expression of marker proteins (if any one or a plurality of the marker proteins described later are expressed, the organ bud can be judged as the organ bud of interest). For example, HHEX, SOX2, HNF4A, AFP, ALB and the like are markers for liver buds; PDX1, SOX17, SOX9 and the like are markers for pancreas bud; and CDX2, SOX9 and the like are markers for organ buds which differentiate into intestinal tract. Among the terms used by those skilled in the art, the following are included in the organ bud of the present invention: liver bud, liver diverticula, liver organoid, pancreatic (dorsal or ventral) buds, pancreatic diverticula, pancreatic organoid, intestinal bud, intestinal diverticula, intestinal organoid (K. Matsumoto, et al. Science. 19; 294 (5542): 559-63 (2001)) and so on.

In the present invention, the term "organ cell" means functional cells constituting organs or undifferentiated cells which differentiate into functional cells. Examples of "undifferentiated organ cell" include, but are not limited to, cells capable of differentiating into an organ such as kidney, heart, lung, spleen, esophagus, stomach, thyroid, parathyroid, thymus, gonad, brain or spinal cord; cells capable of differentiating into an ectodermal organ such as brain, spinal cord, adrenal medulla, epidermis, hair/nail/dermal gland, sensory organ, peripheral nerve or lens; cells capable of differentiating into a mesodermal organ such as kidney, urinary duct, heart, blood, gonad, adrenal cortex, muscle, skeleton, dormis, connective tissue or mesothelium; and cells capable of differentiating into an endodermal organ such as liver, pancreas, intestinal tract, lung, thyroid, parathyroid or urinary tract. Whether or not a cell is capable of differentiating into an ectodermal organ, mesodermal organ or endodermal organ can be judged by examining the expression of marker proteins (if any one or a plurality of marker proteins are expressed, the cell can be judged as a cell capable of differentiating into an endodermal organ). For example, in cells capable of differentiating into liver, HHEX, SOX2, HNF4A, AFP, ALB and the like are markers; in cells capable of differentiating into pancreas, PDX1, SOX17, SOX9 and the like are markers; in cells capable of differentiating into intestinal tract, CDX2, SOX9 and the like are markers; in cells capable of differentiating into kidney, SIX2 and SALL1 are markers; in cells capable of differentiating into heart, NKX2-5, MYH6, ACTN2, MYL7 and HPPA are markers; in cells capable of differentiating into blood, C-KIT, SCA1, TER119 and HOXB4 are markers; and in cells capable of differentiating into brain or spinal cord, HNK1, AP2, NESTIN and the like are markers. Among the terms used by those skilled in the art, the following are included in the "undifferentiated organ cell" of the present invention: hepatoblast, hepatic progenitor cells, hepatic precursor cells, pancreatoblast, pancreatic progenitors, pancreatic progenitor cells, pancreatic precursor cells, endocrine precursors, intestinal progenitor cells, intestinal precursor cells, intermediate mesodeim, metanephric mesenchymal precursor cells, multipotent nephron progenitor, renal progenitor cells, cardiac mesoderm, cardiovascular progenitor cells, cardiac progenitor cells (J R. Spence, et al. Nature.; 470(7332):105-9. (2011); Self, et al. EMBO J.; 25(21): 5214-5228. (2006); J. Zhang, et al. Circulation Research.; 104: e30-e41(2009); G. Lee, et al. Nature Biotechnology 25, 1468-1475 (2007)) and so on. Undifferentiated organ cells may be prepared from pluripotent stem cells such as induced pluripotent stem cells (iPS cells) or embryonic stem cells (ES cells) according to known methods. For example, organ cells capable of differentiating into liver may be prepared as previously described (K. Si-Taiyeb, et al. Hepatology, 51 (1): 297-305(2010); T. Touboul, et al. Hepatology. 51 (5):1754-65 (2010)); organ cells capable of differentiating into pancreas may be prepared as previously described (D. Zhang, et al. Cell Res.; 19(4):429-38 (2009)); organ cells capable of differentiating into intestinal tract may be prepared as previously described (J. Cai, et al. J Mol Cell Biol.; 2(1):50-60 (2010); R. Spence, et al. Nature.; 470 (7332):105-9 (2011)); cells capable of differentiating into heart may be prepared as previously described (J. Zhang, et al. Circulation Research.; 104: e30-e41(2009); and organ cells capable of differentiating into brain or spinal cord may be prepared as previously described (G. Lee, et al. Nature Biotechnology 25, 1468-1475 (2007)). Examples of "differentiated organ cell" include, but are not limited to, endocrine cells of pancreas, pancreatic duct epithelial cells of pancreas, hepatocytes of liver, epithelial cells of intestinal tract, tubular epithelial cells of kidney, podocytes of kidney, cardiomyocytes of heart, lymphocytes and granulocytes of blood, erythrocytes, neurons and glial cells of brain, and neurons and Schwann cells of spinal cord. As organ cells, human-derived cells are mainly used. However, organ cells derived from non-human animals, such as mouse, rat, dog, pig or monkey, may also be used.

In the present invention, the term "vascular endothelial cell" means cells constituting vascular endothelium or cells capable of differentiating into such cells. Whether a cell is vascular endothelial cell or not can be judged by examining the expression of marker proteins such as TIE2, VEGFR-1, VEGFR-2, VEGFR-3 and CD41 (if any one or a plurality of the above-listed marker proteins are expressed, the cell can be judged as vascular endothelial cell). The vascular endothelial cell used in the present invention may be either differentiated or undifferentiated. Whether a vascular endothelial cell is differentiated or not can be judged by means of CD31 and CD144. Among the terms used by those skilled in the art, the following are included in the "vascular endothelial cell" of the present invention: endothelial cells, umbilical vein endothelial cells, endothelial progenitor cells, endothelial precursor cells, vasculogenic progenitors, hemangioblast (H J. Joo, et al. Blood. 25; 118(8):2094-104 (2011)) and so on. As vascular endothelial cells, human-derived cells are mainly used. However, vascular endothelial cells derived from non-human animals, such as mouse, rat, dog, pig or monkey, may also be used.

In the present invention, the term "mesenchymal cell" means connective tissue cells that are mainly located in mesoderm-derived connective tissues and which form support structures for cells that function in tissues. The "mesenchymal cell" is a concept that encompasses those cells which are destined to, but are yet to, differentiate into mesenchymal cells. Mesenchymal cells used in the present invention may be either differentiated or undifferentiated. Whether a cell is an undifferentiated mesenchymal cell or not may be determined by examining the expression of marker proteins such as Stro-1, CD29, CD44, CD73, CD90, CD105, CD133, CD271 or Nestin (if any one or a plurality of the above-listed marker proteins are expressed, the cell can be judged as undifferentiated mesenchymal cell). A mesenchymal cell in which none of the above-listed markers are expressed can be judged as differentiated mesenchymal cell. Among the terms used by those skilled in the art, the following are included in the "mesenchymal cell" of the present invention: mesenchymal stem cells, mesenchymal progenitor cells, mesenchymal cells (R. Peters, et al. PLoS One. 30; 5(12):e15689 (2010)) and so on. As mesenchymal cells, human-derived cells are mainly used. However, mesenchymal cells derived from non-human animals, such as mouse, rat, dog, pig or monkey, may also be used.

Culture ratios of the three cell types in coculture are not particularly limited as long as the ratio enables the formation of organ buds. A preferable cell count ratio is as follows. Organ cell:vascular endothelial cell:undifferentiated mesenchymal cell=10:10-5:2-1.

Either one or both of vascular endothelial cell and mesenchymal cell may be substituted by substances such as factors secreted by vascular endothelial cells, factors secreted by mesenchymal cells, factors secreted as a result of the presence of both vascular endothelial cells and mesenchymal cells, and so forth.

Examples of the substances such as factors secreted by vascular endothelial cells, factors secreted by mesenchymal cells, factors secreted as a result of the presence of both vascular endothelial cells and mesenchymal cells, and so forth include, but are not limited to, FGF2, FGF5, BMF4, BMP6 and CTGF.

With respect to the amount of addition of these substances, FGF2 may be added at 10-100 ng/ml, preferably at about 20 ng/ml, per $1 \times 10^6$ cells; and BMF4 may be added at 10-100 ng/ml, preferably at about 20 ng/ml, per $1 \times 10^6$ cells.

The medium used for culturing is not particularly limited. Any medium may be used as long as it enables the formation of organ buds. Preferably, a medium for culturing endothelial vascular cells, a medium for culturing organ cells or a mixture of these two media may be used. As a medium for culturing endothelial vascular cells, any medium may be used but, preferably, a medium containing at least one of the following substances may be used: hEGF (recombinant human epidermal growth factor), VEGF (vascular endothelial growth factor), hydrocortisone, bFGF, ascorbic acid, IGF1, FBS, antibiotics (e.g., gentamycin or amphotericin B), heparin, L-glutamine, phenol red and BBE. Specific examples of this medium which may be used in the present invention include, but are not limited to, EGM-2 BulletKit (Lonza), EGM BulletKit (Lonza), VascuLife EnGS Comp Kit (LCT), Human Endothelial-SFM Basal Growth Medium (Invitrogen) and human microvascular endothelial cell growth medium (TOYOBO). As a medium for culturing organ cells, any medium may be used but, when the organ cell is hepatocyte, a medium containing at least one of the following substances may be preferably used: ascorbic acid, BSA-FAF, insulin, hydrocortisone and GA-1000. As a medium for culturing hepatocyte, HCM BulletKit (Lonza) from which hEGF (recombinant human epidermal growth factor) has been removed and RPMI1640 (Sigma-Aldrich) to which 1% B27 Supplements (GIBCO) and 10 ng/mL hHGF (Sigma-Aldrich) have been added may typically be used. With respect to formation of human liver buds, use of a medium prepared as described below has been found effective for maturation of liver buds. Briefly, GM BulletKit (Lonza) and HCM BulletKit (Lonza) from each of which hEGF has been removed are mixed at 1:1 and to the resultant mixture, dexamethasone, oncostatin M and HGF are added.

Preferably, organ cells are plated on a gel and cultured. The gel used for this purpose is not particularly limited. For example, BD Matrigel (BD Pharmingen) may be used.

The temperature at the time of culture is not particularly limited. The temperature is preferably 30-40° C., more preferably 37° C.

The time period of culture is not particularly limited. The period is preferably 3-10 days, more preferably 6 days.

The thus prepared organ bud is transplanted into a non-human animal, in which the organ bud is allowed to mature to thereby yield a tissue or organ. As the non-human animal, mouse, rabbit, pig, dog, monkey or the like may be used. Further, the non-human animal used herein is preferably an immunodeficient animal for the purpose of avoiding immunorejection.

Therefore, the present invention also provides a method of transplanting an organ bud, comprising transplanting the organ bud prepared by the above-described method into a human or a non-human animal. The site of transplantation of the organ bud may be any site as long as transplantation is possible. Specific examples of the transplantation site include, but are not limited to, the intracranial space, the mesentery, the liver, the spleen, the kidney, the kidney subcapsular space, and the supraportal space. When the organ bud is to be transplanted into the cranium, about 1 to 3 organ buds of 5 mm in size, prepared in vitro, may be transplanted. When the organ bud is to be transplanted into the mesentery, about 1 to 6 organ buds of 5 nm in size, prepared in vitro, may be transplanted. When the organ bud is to be transplanted in the supraportal space, about 1 to 20 organ buds of 5 mm in size, prepared in vitro, may be transplanted. When the organ bud is to be transplanted in the kidney subcapsular space, about 1 to 5 organ buds of 5 mm in size, prepared in vitro, may be transplanted. When the organ bud is to be transplanted into the liver, spleen or kidney, about 100 to 200 organ buds of 100 μm in size, prepared in vitro, may be transplanted.

The tissue and organ prepared as described above may be used for drug discovery screening and regenerative medicine.

Therefore, the present invention also provides a method for regeneration or function discovery of a tissue or an organ, comprising transplanting an organ bud prepared by the above-described method into a human or a non-human animal and differentiating the organ bud into a tissue or an organ. As the non-human animal, mouse, rabbit, pig, dog, monkey or the like may be enumerated.

Further, the present invention also provides a method of preparing a non-human chimeric animal, comprising transplanting an organ bud prepared by the above-described method into a non-human animal and differentiating the organ bud into a tissue or an organ. The non-human animal (e.g., mouse) into which the organ bud has been transplanted is capable of mimicking the physiological function of the organism species from which the organ cell used in preparing the organ bud has been derived (e.g., human). In an Example to be described later, it was confirmed that mice into which organ buds prepared from human-derived iPS cells had been transplanted mimicked human liver function. Therefore, it is held possible to predict human drug metabolism profiles using those mice.

Further, the present invention also provides a method of evaluating a drug, comprising using at least one member selected from the group consisting of an organ bud, a tissue or organ and a non-human chimeric animal prepared by the above-described methods. Specific examples of drug evaluation include, but are not limited to, prediction of the drug metabolism profiles of candidate compounds for a drug, evaluation of drug efficacy, toxicity evaluation and evaluation of drug interactions.

Further, it is also possible to generate tissue stem cells from the tissues or organs prepared by the method of the invention. Thus, the present invention is applicable to a cell manipulation technique intended for mass generation of human tissue cells and organ cells.

EXAMPLES

Hereinbelow, the present invention will be described in more detail with reference to the following Examples.

Example 1

Preparation of an Organ from Undifferentiated Organ Cell

Experimental Methods (1) Preparation of Human Hepatic Endoderm Cells
  Human iPS cells (human skin-derived TkDA3 hiPSC clone (provided by Mr. Koji Eto and Mr. Hiromitsu Nakauchi)) were cultured in an activin-supplemented serum-free medium to thereby induce CXCR4- and E-cadherin-positive endodermal cells. The resultant endodermal cells were cultured in the presence of added BMP4 and FGF2 for 2 days to thereby obtain CXCR4-negative and HNF4α-positive hepatic endoderm cell populations. Expression of CXCR4 and HNF4α was confirmed by immunostaining and gene expression analysis as described previously (Hepatology, 51(1), 297-305, 2010).

(2) Preparation of Human Liver Buds

The resultant hepatic endoderm cell was cocultured with a vascular endothelial cell (human umbilical cord blood-derived vein endothelial cell) (Lonza, Basel, Switzerland) and an undifferentiated mesenchymal cell (human mesenchymal stem cell) (Lonza, Basel, Switzerland) mixed at 10:5-10:2. The vascular endothelial cell and the undifferentiated mesenchymal cell were individually labeled with fluorescence in advance. In the coculture, cell suspension was seeded on pre-solidified Matrigel (BD pharmingen) (stock gel or 2-fold dilution) in a culture dish. As a culture broth, endothelial cell medium kit-2: EGM-2 BulletKit (product code CC-3162: Lonza) was used.

Cells were cultured for a short period of time (3-10 days) to prepare human three-dimensional structures (liver buds). The process of formation and the formed structures were observed under confocal microscope, and kinetic/static analyses of cell morphology and localization were performed. Further, gene expression analysis was performed on the thus formed human three-dimensional structures.

(3) Preparation of Human Liver Tissue

The formed human three-dimensional structure was transplanted into the living body of an immunodeficient mouse (NOD/SCID mouse (Sankyo Lab. Co., Tsukuba, Japan)). Macroscopic and confocal microscopic live observations were performed, followed by confirmation of engraftment/proliferation of human cells and analysis of post-transplantation vascular maturation processes. Early samples (2 weeks post-transplantation) were recovered and analyzed histologically.

Figure 2:
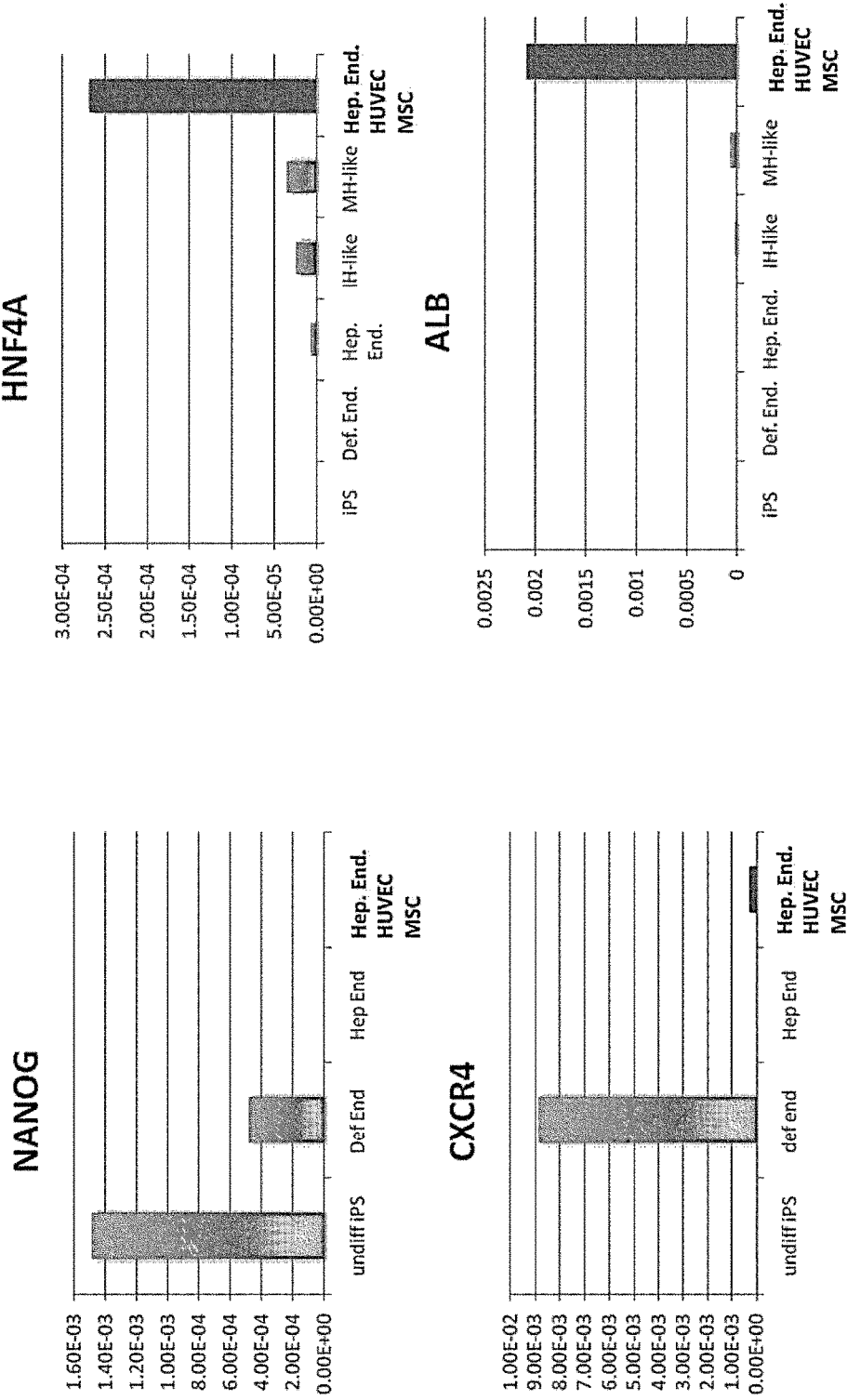
FIG. 2 This figure shows expression levels of marker proteins as for cells that constitute organ buds. "Hep. End. HUVEC MSC" represents cells constituting organ buds; "undiff iPS" and "iPS" represent iPS cells; "Def End" represents activin-induced endoderm cells; "Hep End" represents BMP4- and FGF2-induced hepatic endoderm cells. "IH-like" represents immature hepatocyte-like cells described in K. Si-Taiyeb, et al. Hepatology, 51 (1): 297-305 (2010) and "MH-like" represents mature hepatocyte-like cells described in the same reference.
Figure 3:
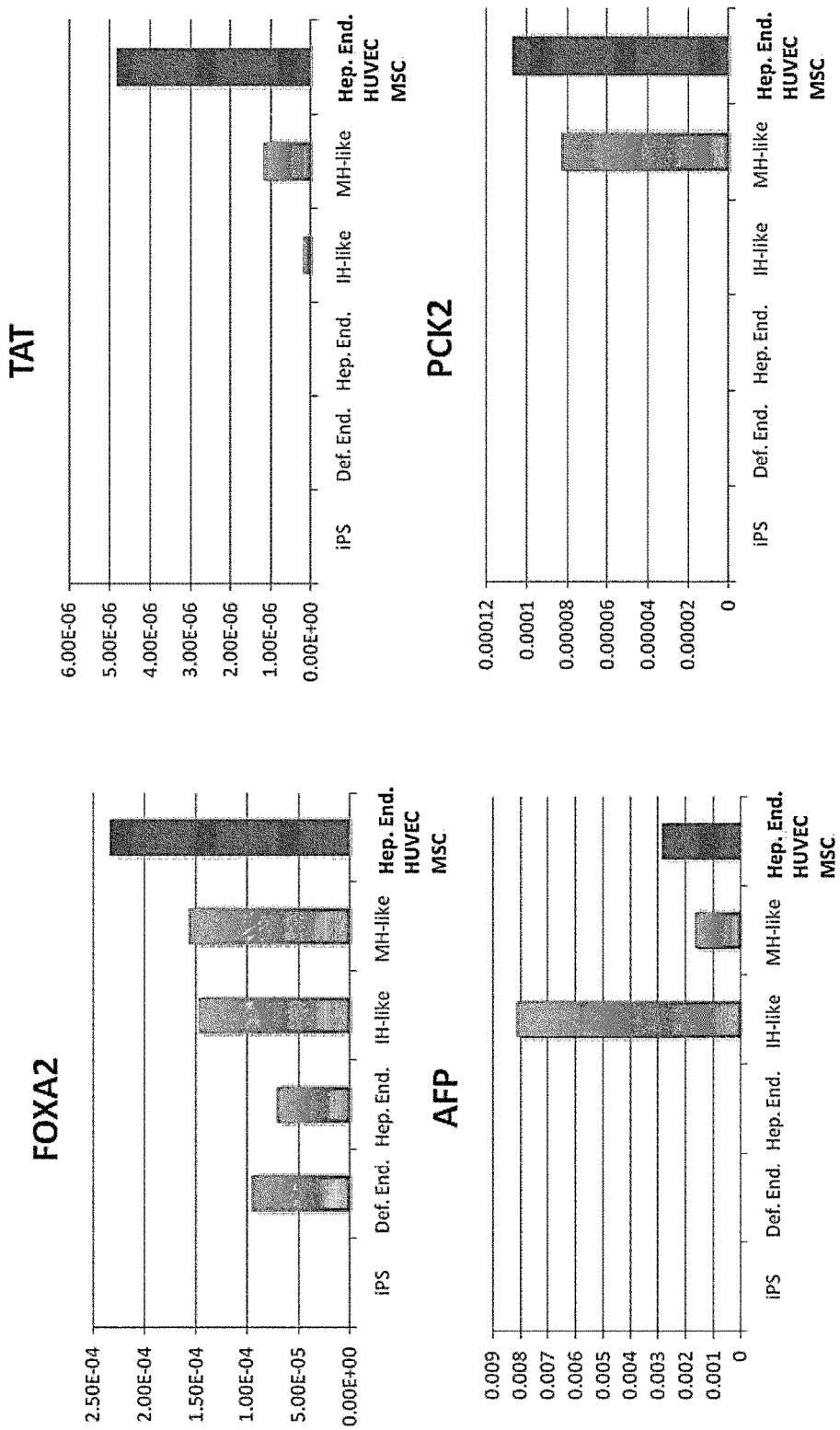
FIG. 3 This figure shows expression levels of marker proteins as for cells that constitute organ buds. "Hep. End. HUVEC MSC" represents cells constituting organ buds; "iPS" represents iPS cells; "Def End" represents activin-induced endoderm cells; "Hep End" represents BMP4- and FGF2-induced hepatic endoderm cells. "IH-like" represents immature hepatocyte-like cells described in K. Si-Taiyeb, et al. Hepatology, 51 (1): 297-305 (2010) and "MH-like" represents mature hepatocyte-like cells described in the same reference.
Figure 4:
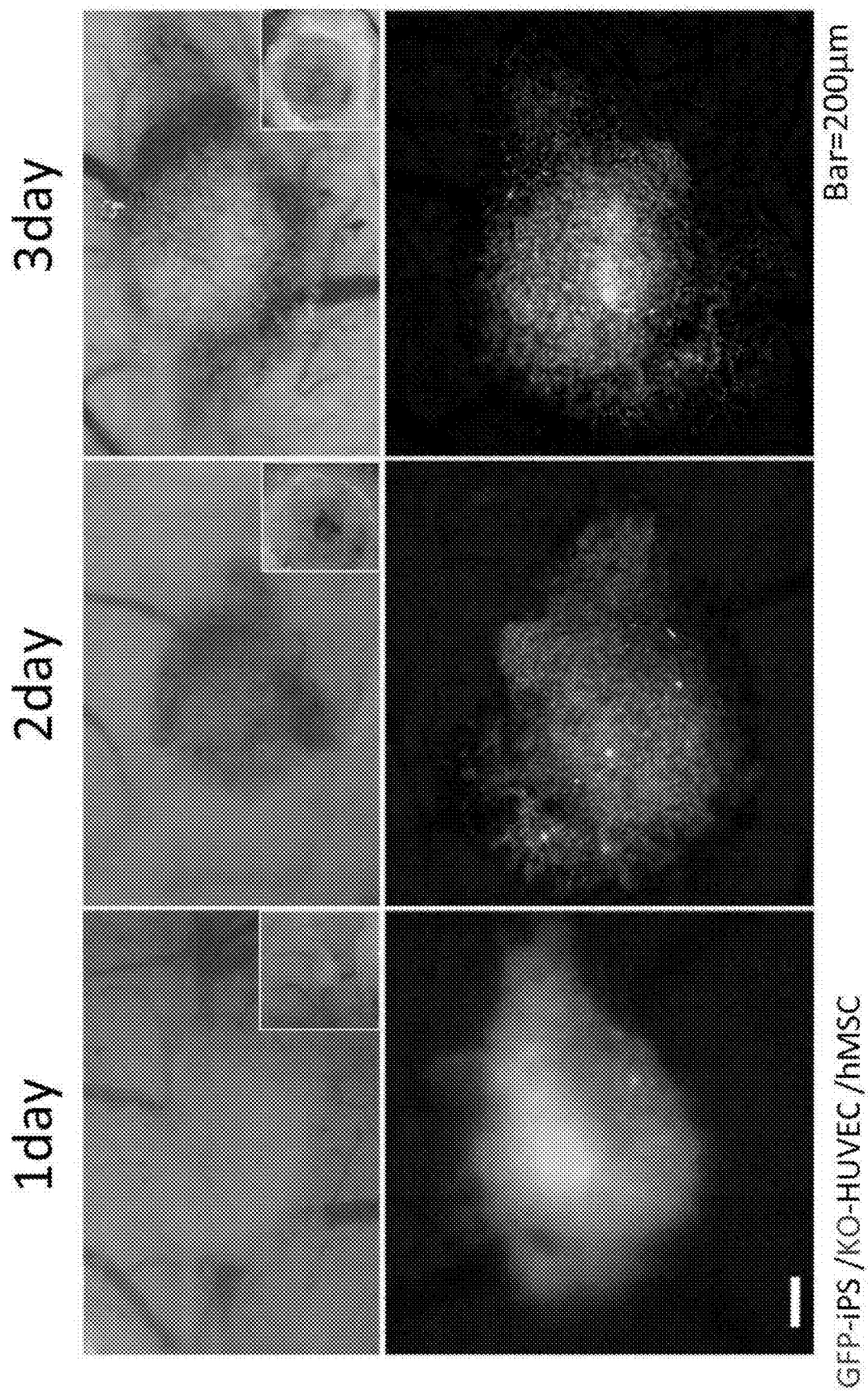
FIG. 4 This figure shows the state of a liver bud transplanted into an immunodeficient mouse. iPS cells are labeled with GFP and undifferentiated endothelial cells are labeled with KO.
Figure 5:
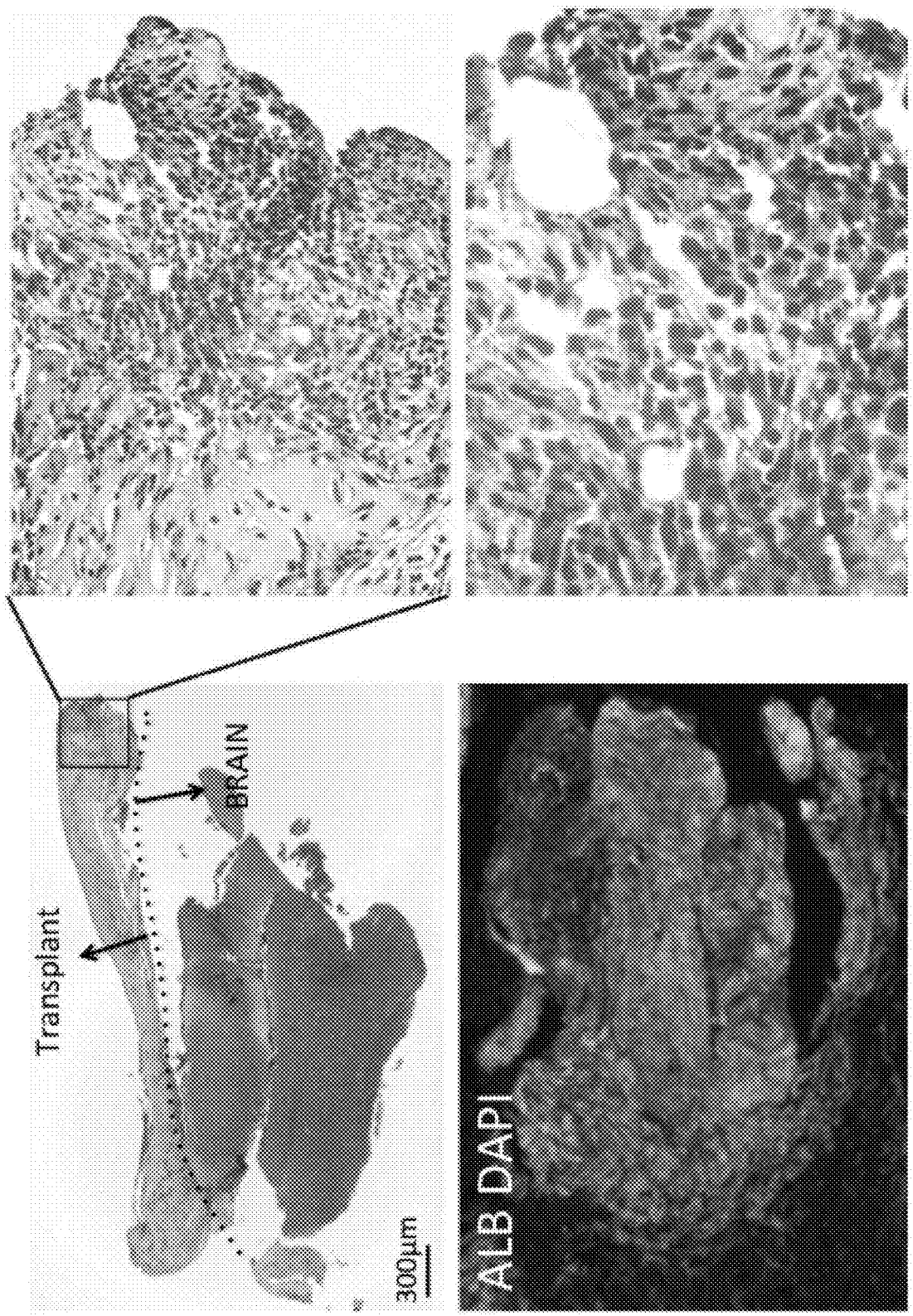
FIG. 5 This figure shows histological analysis of a liver bud 2 weeks after transplantation.

Experimental Results (1) Autonomous organization progressed only from human cells, forming a macroscopically observable three-dimensional structure (FIG. 1)
(2) At day 4 of culture, a vessel-like luminal structure was confirmed (FIG. 1, upper right panel, enlarged image).
(3) The formed three-dimensional structure was attenuated in the expression of undifferentiated cell markers NANOG and CXCR4 (FIG. 2).
(4) Compared with those cells in which terminal differentiation was induced by conventional techniques, expression of a hepatocyte differentiation marker albumin (ALB) was enhanced more than 100 times (FIG. 2) and expressions of other differentiation markers (FOXA2, TAT and PCK2) were also enhanced about several ten times (FIG. 3).
(5) By transplantation, human blood vessels were connected with mouse blood vessels, and blood perfusion began early (2 days post-transplantation) (FIG. 4).
(6) Proliferation of human iPS cell-derived hepatocytes was confirmed (FIG. 5).
(7) Histological analysis of early samples (2 weeks post-transplantation) confirmed formation of albumin-positive cord-like structures. Formation of sinusoid-like structures was also confirmed (FIG. 5).
(8) In the coculture, when cell suspension was not seeded on Matrigel-solidified culture dish but embedded in Matrigel, or seeded on non-coated culture dish, or seeded on type I collagen-coated culture dish, no three-dimensional structures formed.
(9) In the coculture, when Hepatocyte Medium (XenoTech) or BMP4- and FGF2-supplemented hepatocyte inducing medium (Hepatology, 51(1), 297-305, 2010) was used instead of the endothelial cell medium as a culture broth, enhanced expression of genes characteristic of liver buds (Alb, TTR, etc.) was not recognized.

Example 2

Preparation of an Organ from Differentiated Organ Cell

Experimental Methods

Pancreatic β cell strain (MIN6) was cocultured with a vascular endothelial cell (human umbilical cord blood-derived vein endothelial cell) and an undifferentiated mesenchymal cell (human mesenchymal stem cell) mixed at 5:5-10:2. The pancreatic β cell strain (KO) and the vascular endothelial cell (EGFP) were individually labeled with fluorescence in advance. In the coculture, cell suspension was seeded on pre-solidified Matrigel (BD pharmingen) (stock gel or 2-fold dilution) in a culture dish. When cell suspension was embedded in Matrigel, or seeded on non-coated culture dish, or seeded on type I collagen-coated culture dish, no three-dimensional structures formed. As a culture broth, endothelial cell medium kit-2: EGM-2 BulletKit (product code CC-3162: Lonza) was used.

Cells were cultured for a short period of time (3-10 days) to prepare three-dimensional structures. The process of formation and the formed structures were observed under confocal microscope, and kinetic/static analyses of cell morphology and localization were performed.

The formed three-dimensional structure was transplanted into the living body of an immunodeficient mouse (NOD/SCID mouse (Sankyo Lab. Co., Tsukuba, Japan)). Macroscopic and confocal microscopic live observations were performed, followed by confirmation of engraftment/proliferation of cells and analysis of post-transplantation vascular maturation processes. Transplant samples (4 weeks post-transplantation) were recovered and analyzed histologically.

[Experimental Results]

Figure 6:
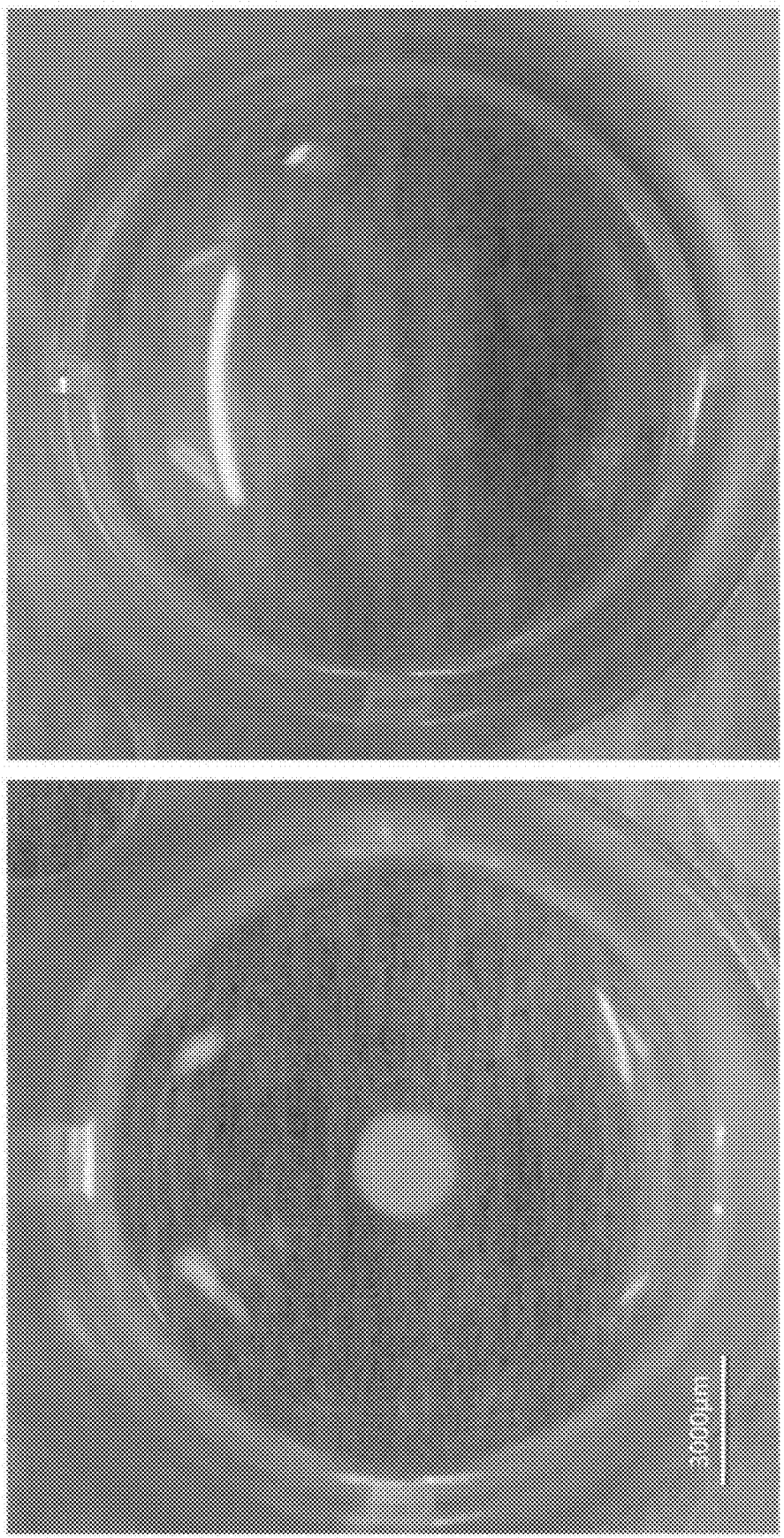
FIG. 6 This figure shows autonomous organization of pancreatic β cells. Left panel shows cocultured pancreatic β cells, and right panel shows independently cultured pancreatic β cells.
Figure 7:
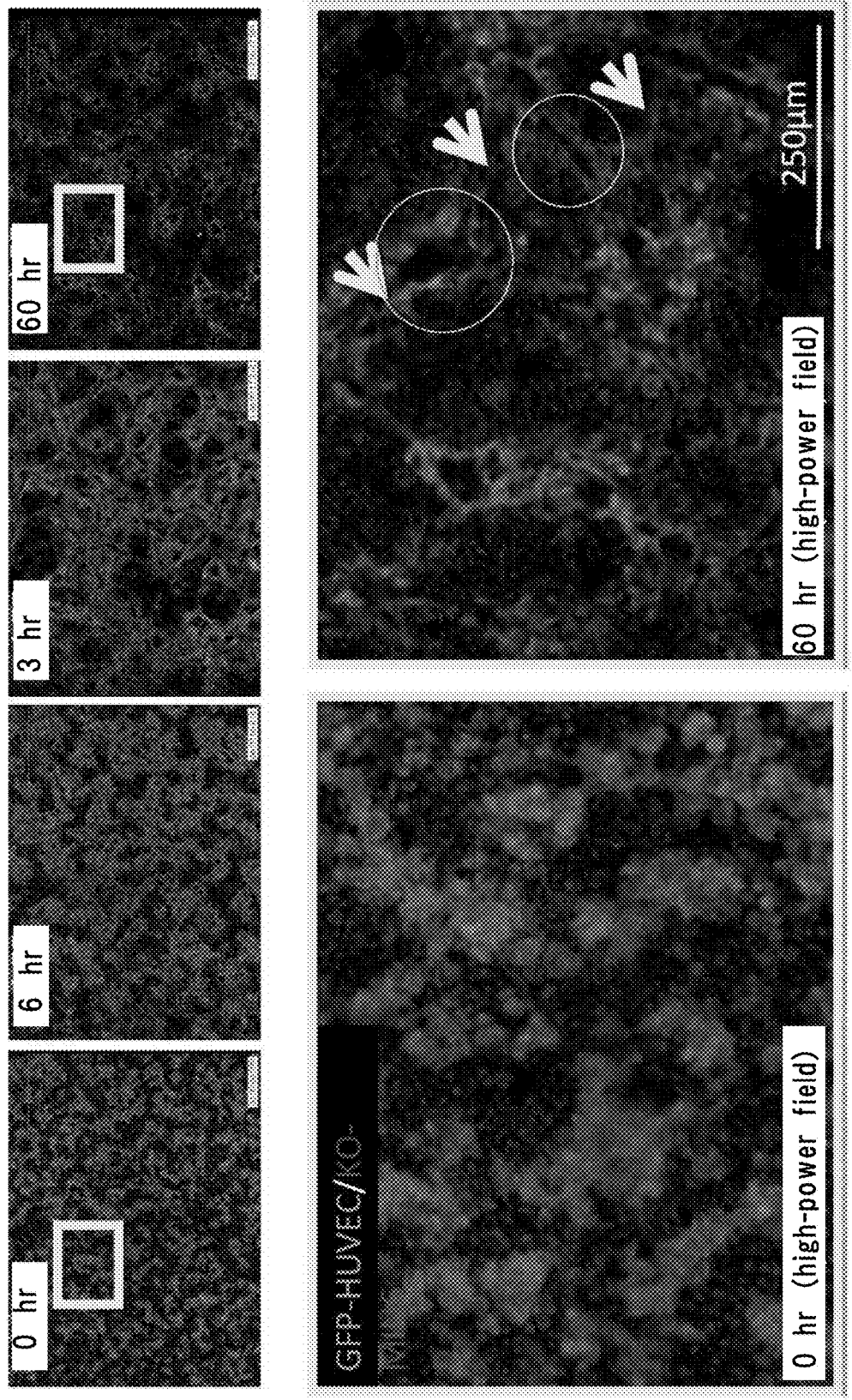
FIG. 7 This figure shows masses and vessel-like luminal structures of pancreatic β cells.
Figure 8:
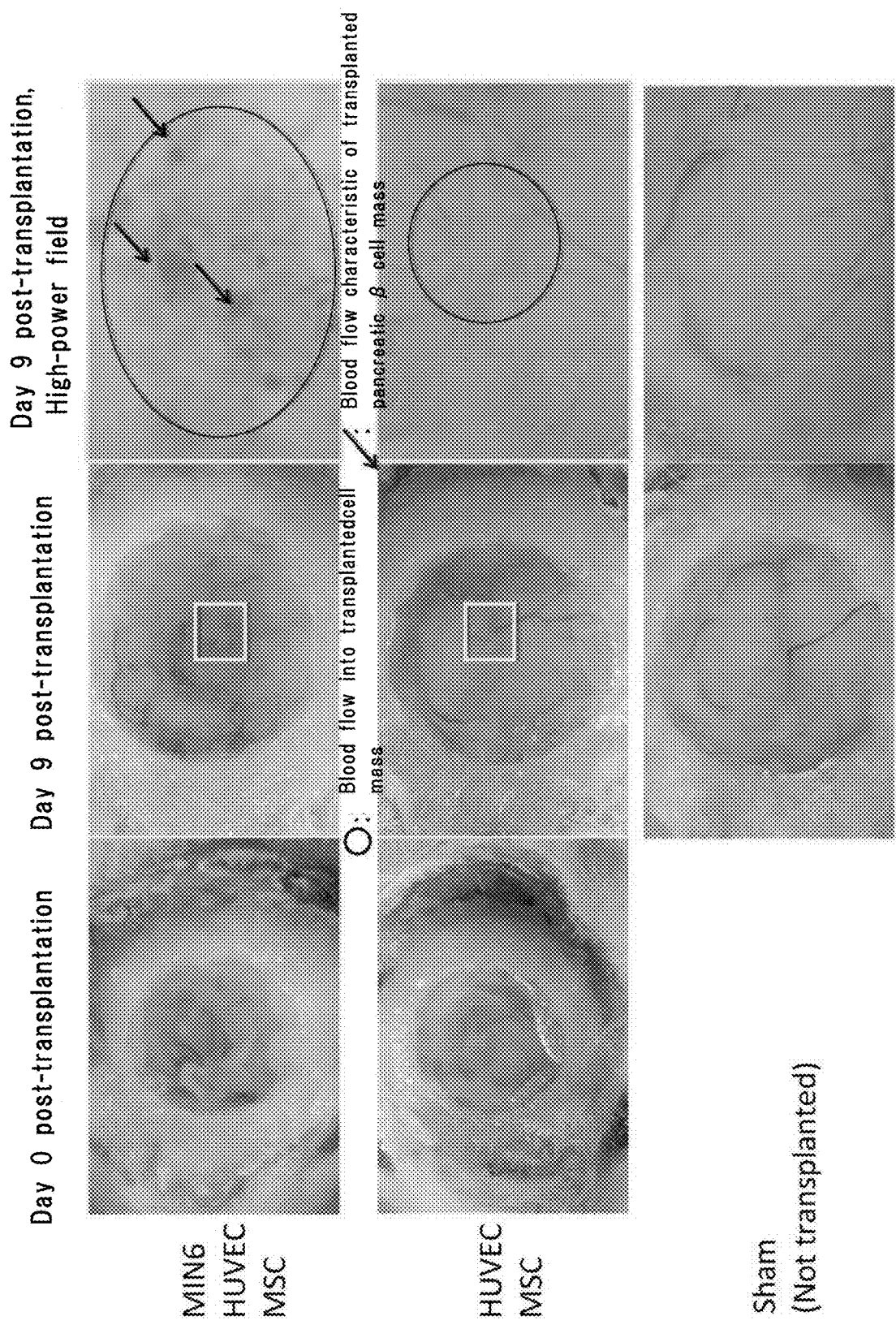
FIG. 8 This figure shows blood perfusion into transplanted cell masses.
Figure 9:
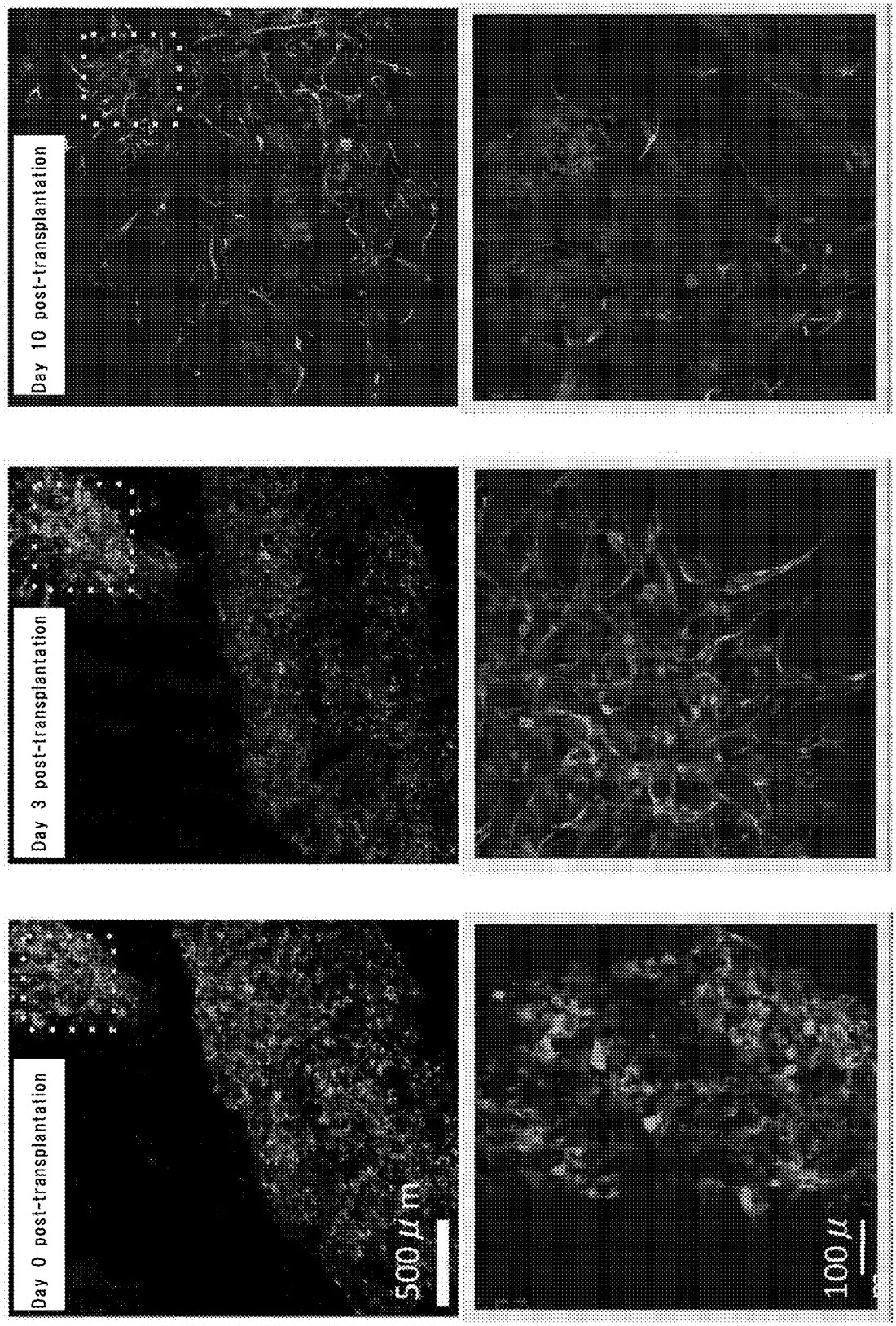
FIG. 9 This figure shows the process of spheroid formation from pancreatic β cells. Vascular endothelial cells (HUVECs) are labeled with GFP and pancreatic β cells (MIN6) are labeled with KO.
Figure 10:
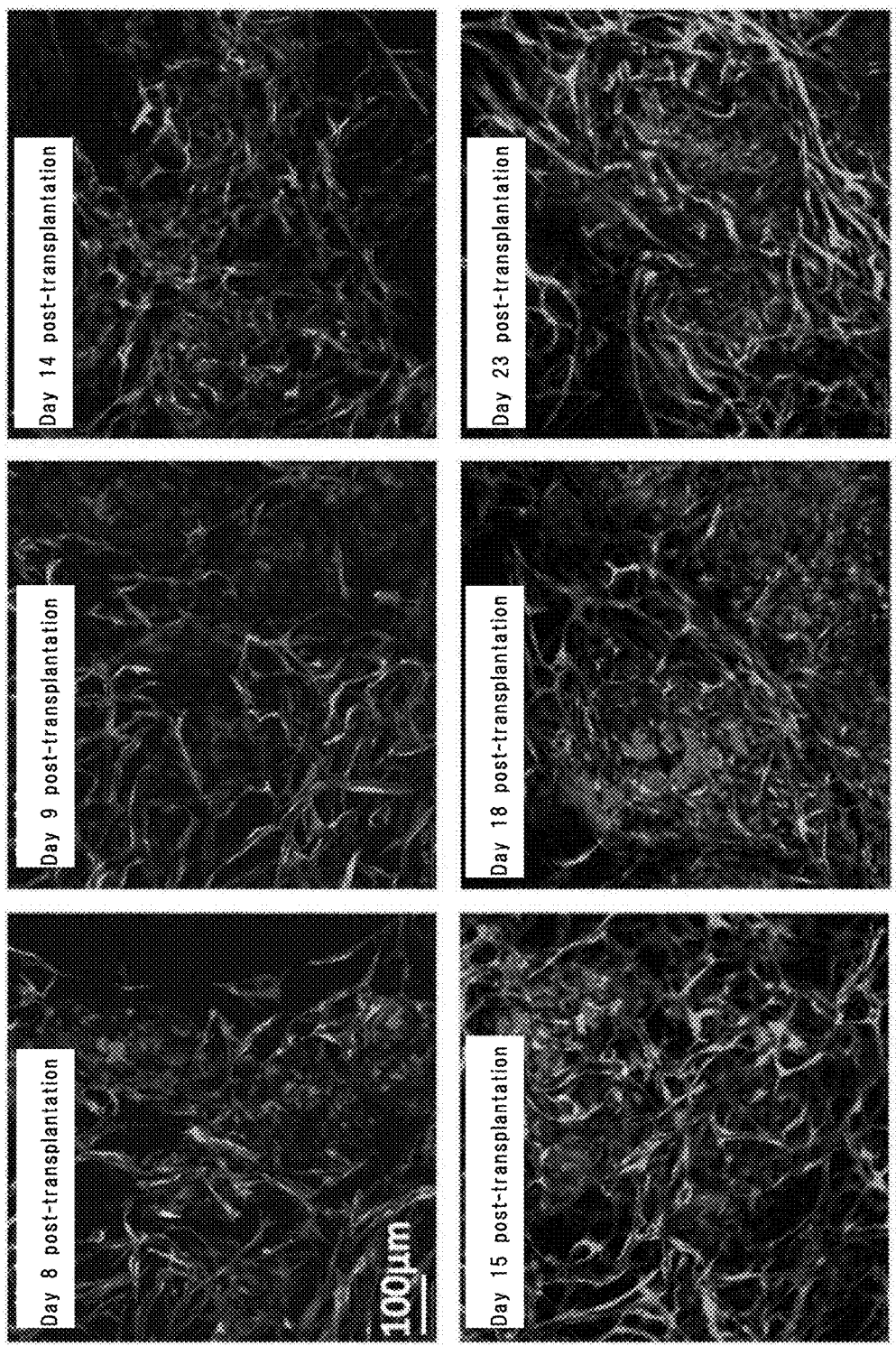
FIG. 10 This figure shows angiogenesis in pancreatic β cell populations. Vascular endothelial cells (HUVECs) are labeled with GFP and pancreatic β cells (MIN6) are labeled with KO.
Figure 11:
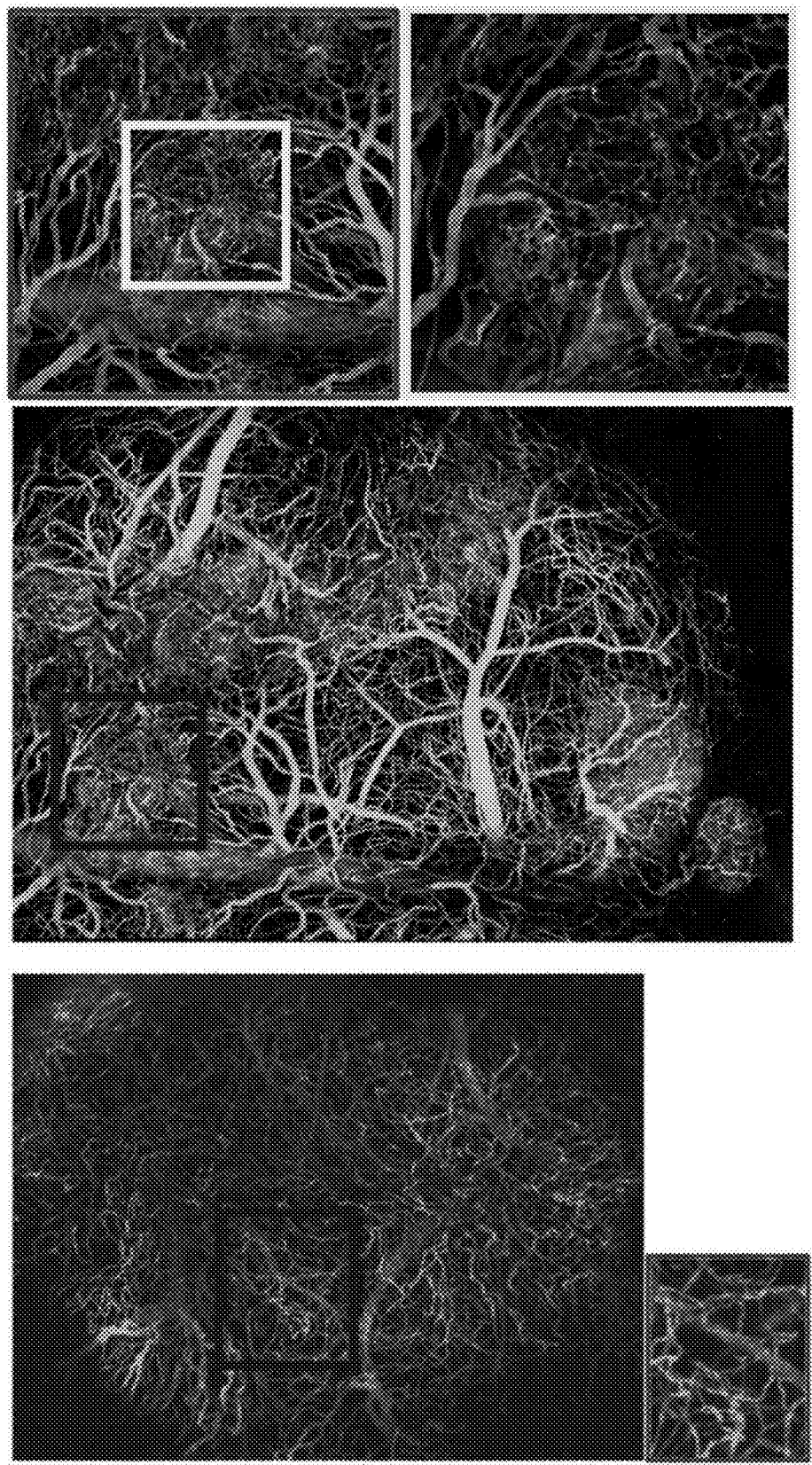
FIG. 11 This figure shows blood perfusion into pancreatic β cell populations. Blood flow is visualized with labeled dextran.

(1) Autonomous organization progressed only from cells, form a macroscopically observable three-dimensional structure on the following day (FIG. 6).
(2) At day 2 of culture, pancreatic β cell strain formed cell masses, around which human vessel-like luminal structures were confirmed (FIG. 7).
(3) By transplantation, human blood vessels were connected with mouse blood vessels, and blood perfusion started early after transplantation (FIG. 8).
(4) Pancreatic β cells proliferated to form cell masses and formed pancreatic islet-like structures (FIG. 9).
(5) Formation of vasculatures consisting of human cells was confirmed in the formed pancreatic islet-like structures (FIG. 10).
(6) Visualization of blood flow confirmed that sufficient blood perfusion re-started inside the pancreatic islet-like structure (FIG. 11).

Figure 12:
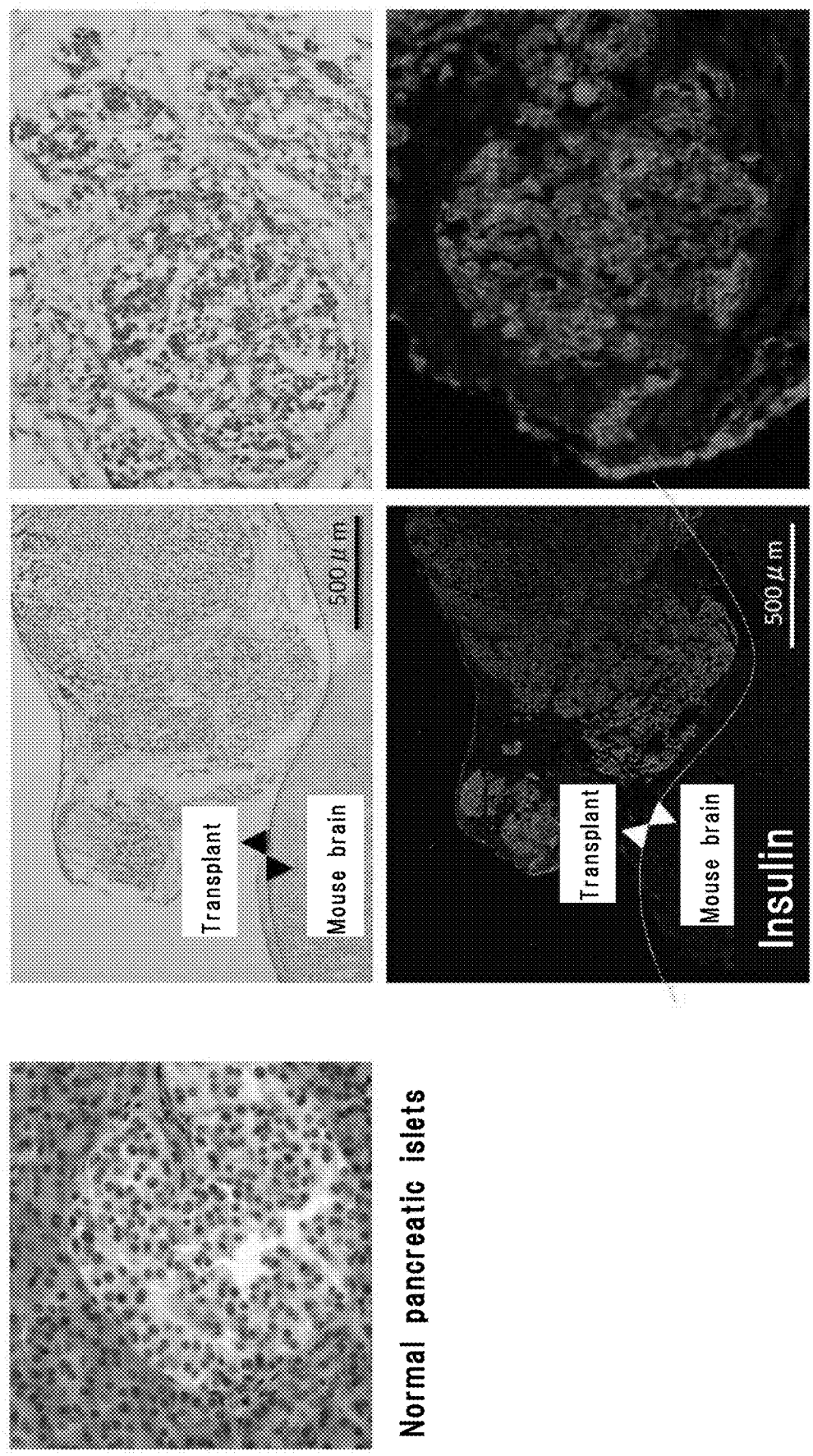
FIG. 12 This figure shows histological analysis of pancreatic β cell populations.

(7) Histological analysis of transplant samples confirmed formation of insulin-positive islet-like structures. The formed structures had complex vasculatures in their inside and had a similar structure to normal mouse pancreatic islets (FIG. 12).

Example 3

Generation of a Functional and Vascularized Human Liver from an Induced Pluripotent Stem Cell-Derived Organ Bud Transplant A critical shortage of donor organs for treating end-stage organ failure highlights the urgent need for generating organs from patient-derived induced pluripotent stem cells (hiPSCs)[1,2]. Despite many reports describing functional cell differentiation[3-7], no studies have succeeded in generating a three-dimensional vascularized organ such as liver. The present inventors have successfully generated a vascularized and functional human liver from hiPSCs by transplantation of liver buds created in vitro (hiPSC-LBs). When endothelial and mesenchymal cells were added to promote organogenesis[8], iPS cell-derived hepatic endoderm cells self-organized into three-dimensional hiPSC-LBs Immunostaining and gene-expression analyses revealed a resemblance between in vitro-grown hiPSC-LBs and in vivo liver buds. Human vasculatures in hiPSC-LB transplants connected to the host blood vessels within 48 hours to start blood perfusion. It became clear that the formation of functional vasculatures stimulated the maturation of hiPSC-LBs into a tissue resembling the adult liver. Highly metabolic hiPSC-derived transplant tissue performed liver-specific functions such as human-type protein production and human-specific drug metabolism, without recipient's liver replacement[9,10]. Furthermore, mesenteric transplantation of hiPSC-LBs rescued a drug-induced lethal liver failure model. As far as the present inventors know, this is the first report demonstrating the generation of a functional human organ from pluripotent stem cells. Although efforts must be made to apply these techniques to clinical treatments, this proof-of-concept demonstration of organ-bud transplantation provides a promising new approach to regenerative medicine.

Since the discovery of embryonic stem cells in 1981, decades of laboratory studies have failed to generate a complex vascularized organ such as liver from pluripotent stem cells, giving rise to the prevailing belief that in vitro recapitulation of the complex interactions among cells and tissues during organogenesis is essentially impractical[2,11]. The present inventors challenged this idea by focusing on the earliest process of organogenesis, that is, cellular interactions during organ-bud development.

Figure 17:
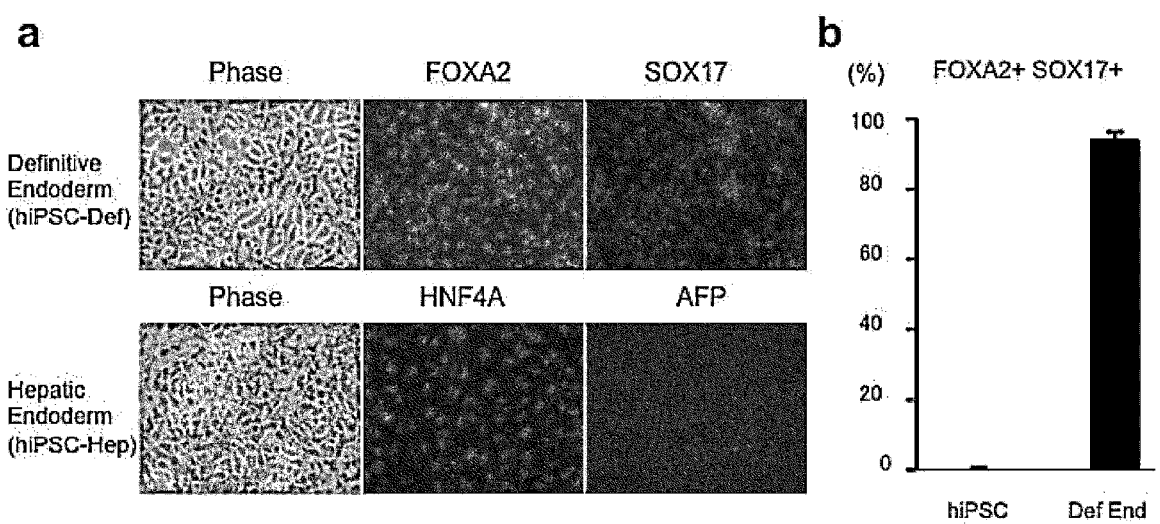
FIG. 17 Induction of early differentiation of hiPSCs into hepatic endoderm.
(a) Differentiation into embryonic endoderm and differentiation into hepatic endoderm both from hiPSCs were monitored by immunostaining for FOXA2, SOX17, HNF4A and AFP at day 6 and 9. (b) Efficiency of differentiation into embryonic endoderm was assessed at day 6 of induction by immunostaining for FOXA2 and SOX17 (results are means±S.D., n=3).

During early liver organogenesis, cells delaminate from the foregut endodermal sheet and form a three-dimensional liver bud (LB)[12]. Such large-scale morphogenetic changes depend on the exquisite orchestration of signals between endodermal, mesenchymal and endothelial progenitors before blood perfusion[8]. Based on these observations, the present inventors hypothesized that three-dimensional liver-bud formation can be recapitulated in vitro by culturing hepatic endoderm cells with endothelial and mesenchymal lineages (FIG. 13a). To examine this hypothesis, the present inventors first prepared hepatic endoderm cells from human iPSCs (hiPSC-Heps) by directed differentiation with gradual addition of inducing factors. As a result, approximately 80% of the treated cells expressed the hepatic marker HNF4A which is involved in cell fate determination (FIGS. 17 and 13b).

Figure 13:
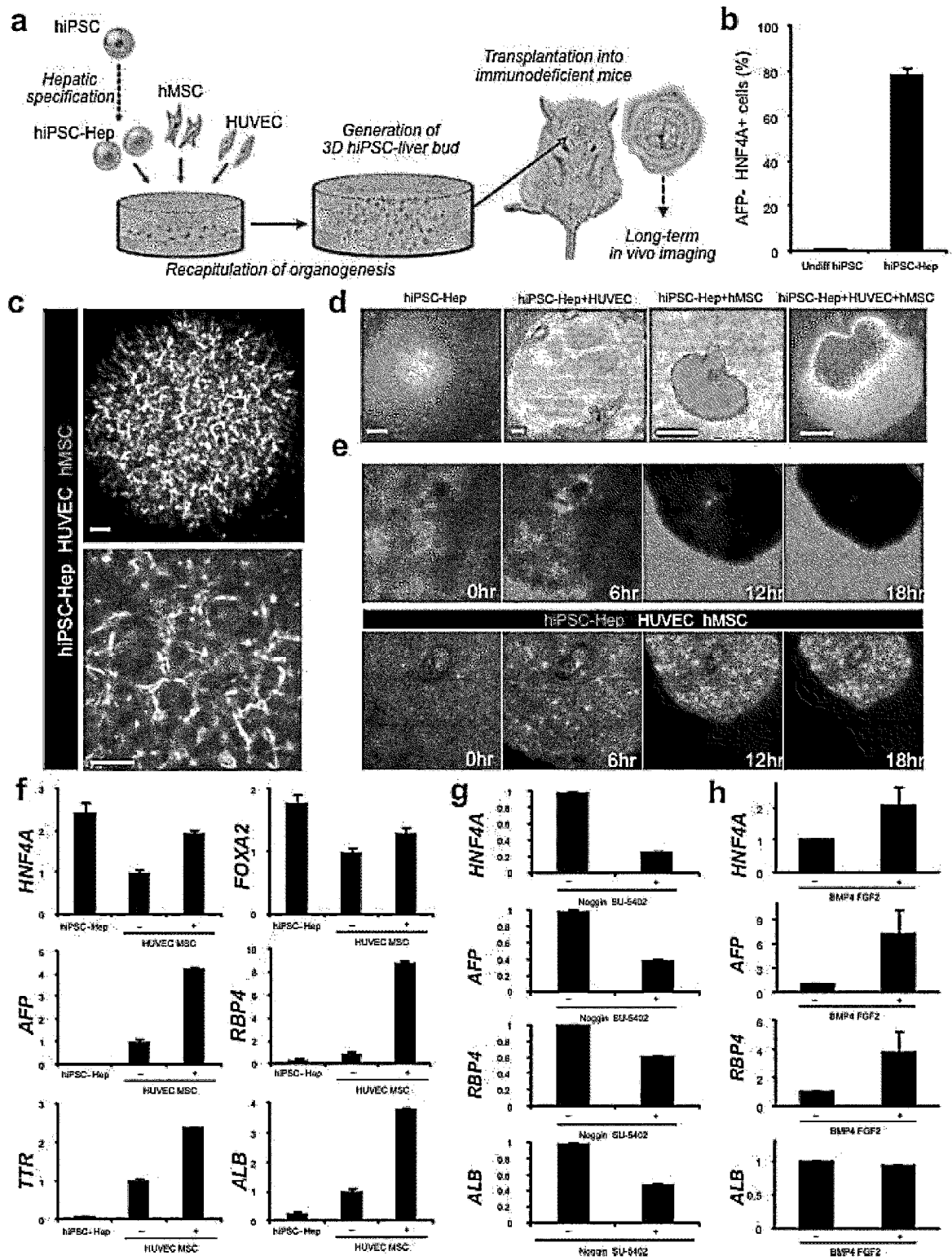
FIG. 13 Generation of human liver buds (hiPSC-LBs) from hiPSCs
(a) Schematic representation of the present technique. (b) Liver endoderm differentiation (hiPSC-Hep) was evaluated by immunostaining for HNF4A and AFP at day 9 (results are shown as means±S.D., n=3). (c) Three-dimensional self-organization of hiPSC-LBs as occurred when hiPSC-Heps were cocultured with HUVECs and hMSCs. Budding of endothelial cells was observed in hiPSC-LBs. Green: EGFP-labeled HUVEC; Red: KOFP (Kusabira Orange Fluorescent Protein)-labeled hMSC. Scale bar, 100 µm. (d) Formation of hiPSC-LBs was not observed in culture systems without hMSCs. Scale bar, 1 mm. (e) Autonomous organization of hiPSC-Heps labeled with Cell Tracker Red CMTMR (Molecular Probes) was confirmed by time-lapse imaging under confocal microscope. Images of confocal Z direction of highest power are projected. (f) Expressions of HNF4A, FOXA2, AFP, RBP4, TTR and ALB from independent culturing of hiPSC-Heps or coculturing of the same with HUVECs and hMSCs in Transwell medium for 96 hours were analyzed by quantitative RT-PCR (qPCR) (results are shown as means±S.D., n=3). (g, h) As a result of expression analysis of hepatic differentiation marker genes, it was shown that addition of the BMP inhibitor Noggin (500 ng/ml) and the FGF inhibitor SU5402 (50 µM) inhibits the efficient hepatic maturation of hiPSC-Heps cocultured with HUVECs and hMSCs (g). On the other hand, when BMP4 (20 ng/ml) and FGF2 (20 ng/ml) were added, it was confirmed that expressions of hepatic markers were enhanced although hiPSC-Heps were cultured independently (h). (Results are shown as means±S.D., n=3).
Figure 18:
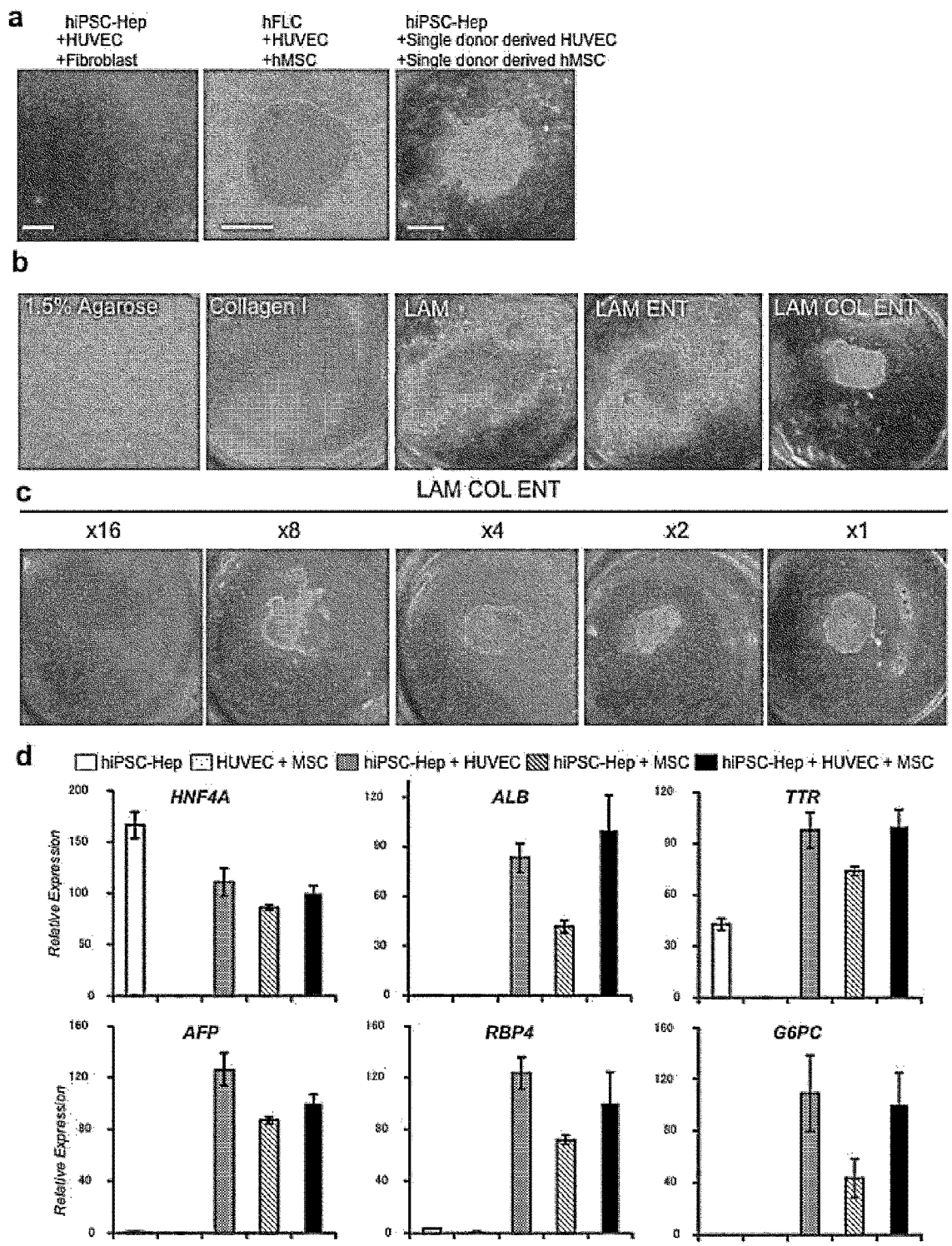
FIG. 18 Optimization of conditions for hiPSC-derived LB formation in vitro.
(a) Formation of liver buds (LB) by coculturing with various cell types. Bars, 1 mm. (b) Hepatic endoderm cells were cocultured with HUVECs and hMSCs on various matrix proteins. Formation of hiPSC-derived LBs (hiPSC-LBs) was observed when cells were seeded on Matrigel (LAM COLENT; a solubilized basement membrane preparation extracted from Engelbreth-Holm-Swarm (EHS) mouse sarcoma). LAM: laminin; ENT: entactin; COL: collagen IV. (c) Effect of matrix protein concentrations on LB formation. (d) qPCR gene expression analysis of hiPSC-LBs. By coculture with endothelial cells and mesenchymal cells, significant increase was observed in the expression levels of early hepatic differentiation markers ALB, RBP4, TTR and G6PC (results are means.+−.S.D., n=3).
Figure 19:
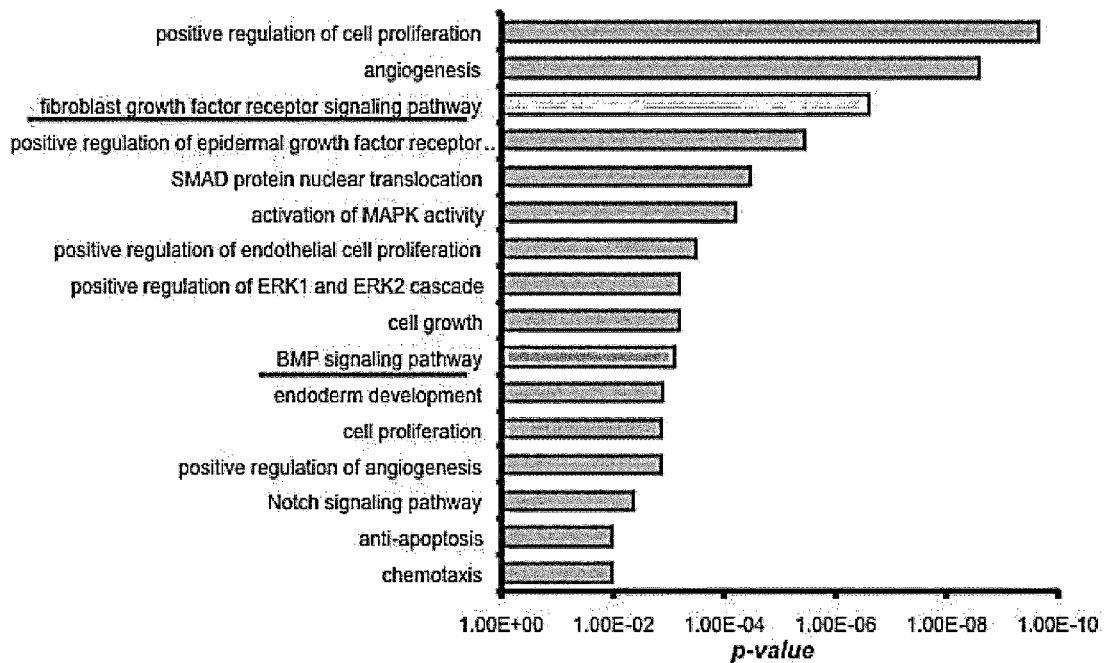
FIG. 19 Identification of humoral factors derived from cocultures with stromal cells.
(a) Gene ontology (GO) analyses of 5000 genes up-regulated in endothelial and mesenchymal cell coculture compared with undifferentiated hiPSCs. Bars represent the significance (P value) of a specific GO category in GO:0008083 (growth factor activity) on biological processes. Among stromal cell-specific genes, FGF signaling (red) and BMP signaling (blue) pathways were emphasized.
(b, c) qPCR analyses of (b) FGFs and (c) BMPs showing that FGF2 and BMP4 are highly expressed in endothelial and mesenchymal cells.
Figure 19:
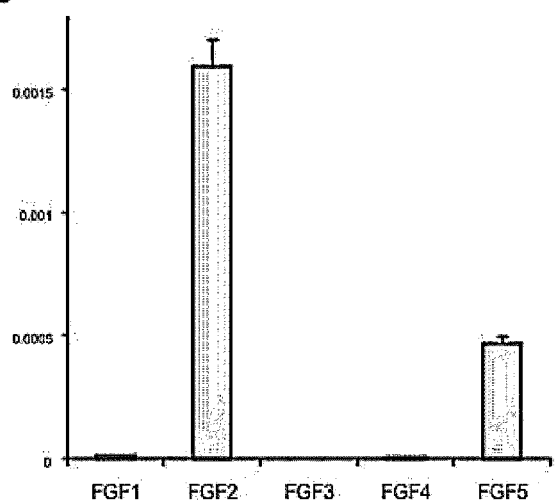
Figure 19:
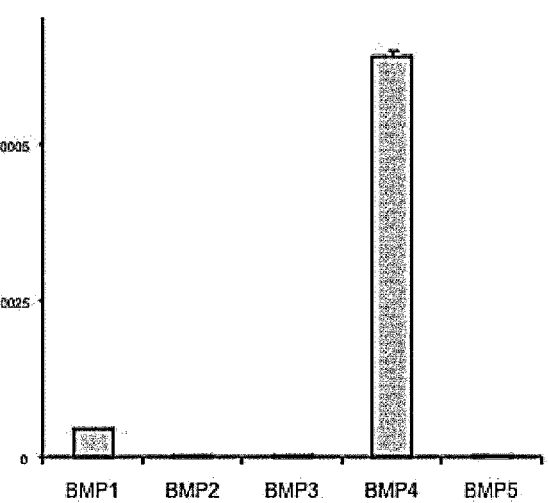

Next, to recapitulate early liver organogenesis, hiPSC-Hep cells were cocultured with stromal cell populations. Human umbilical vein endothelial cells (HUVECs) and human mesenchymal stem cells (hMSCs) were used unless stated otherwise, because of their primitive nature. Notably, though cells were plated in two-dimensional conditions, hiPSC-Hep cells self-organized into macroscopically visible three-dimensional cell clusters by their intrinsic organizing capacity within 24 hours after seeding (FIG. 13 c, d, e). The presumed hiPSC-Hep derived liver buds (hiPSC-LBs) were mechanically stable and could be manipulated physically through transplantation operation. Development of vascular networks accompanied by exquisite bud formation of endothelial cells in hiPSC-LBs was visualized by using fluorescent protein-labeled cells (FIG. 13c). Further, by using a single donor umbilical cord-derived MSCs and HUVECs, hiPSC-LBs were homogeneously distributed (FIG. 18a, right). Quantitative polymerase chain reaction (qPCR) analysis revealed that cells in hiPSC-LBs had significantly increased transcription of early hepatic marker genes such as alpha-fetoprotein (AFP), retinol binding protein 4 (RBP4), transthyretin (TTR) and albumin (ALB)[5] (FIG. 18d). Interestingly, liver maturation of stromal cell-dependent hiPSC-Hep cells was retained to some extent even in coculture systems using Transwell medium (FIG. 13f). Microarray and qPCR analyses were performed to examine intermediary factors which induce liver maturation. Among stromal cell-specific gene groups, expressions of BMP4 and FGF2 were remarkably elevated in coculture systems with endothelial and mesenchymal cells (FIG. 19). Noggin and SU-5402, which are BMP- and FGF-specific signaling inhibitors, inhibited the differentiation promoting effect brought about by coculture with stromal cells. On the other hand, when BMP4 and FGF2 were added to hiPSC-Hep medium, a similar liver differentiation inducing effect was observed (FIG. 13g, h). These results suggest, as observed in animal experiments[13], that in addition to the direct cell-to-cell interactions, paracrine support by stromal cell-dependent humoral factors is partially responsible for early liver maturation through activation of FGF and BMP pathways.

Figure 14:
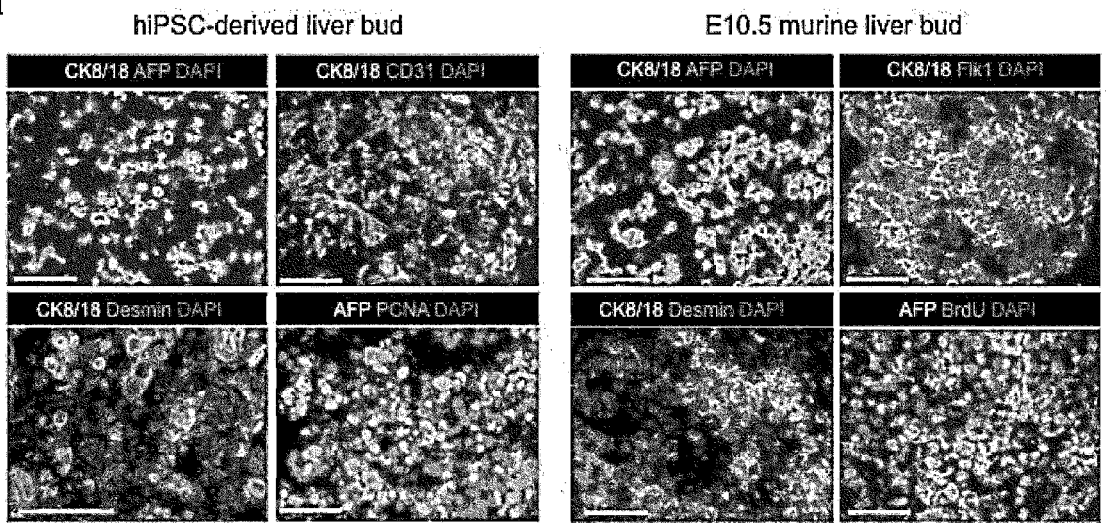
FIG. 14 In vitro Characterization of hiPSC-LBs.
(a) Immunostaining for cytokeratin-8 and -18 (CK8. 18), AFP, PECAM1 (CD31), Flk-1, Desmin, PCNA and 5'-bromo-2'-deoxyuridine (BrdU). Scale bar, 100 µm. (b, c, d, e) The ratios of individual cell species are as follows: hepatoblasts, AFP positive/CK8. 18 positive; proliferating cells, (PCNA positive or BrdU positive)/CK8. 18 positive; endothelial cells, (CD31 positive or Flk1 positive)/DAPI positive; mesenchymal cells, Desmin positive/DAPI positive. The ratios of individual cell species in hiPSC-LBs were almost similar to those of E10.5 mouse LBs (mLBs). In panels b, c and d, the results are shown as means±S.D. In panel e, the results are shown as means S.E.M. In all panels, n=3. (f) With respect to 83 liver-specific genes whose expressions increase gradually during both murine and human liver development, a heat map obtained from microarray data is shown. After in vitro liver bud formation, expressions of this group of liver specific genes remarkably increased. hiPSC-Def: hiPSC-derived embryonic endoderm cells; hiPSC-Hep: hiPSC-derived hepatic endoderm cells; hiPSC-IH: hiPSC-derived immature hepatocyte-like cells; hiPSC-MH: hiPSC-derived mature hepatocytes-like cells; hFLT: fetus (late pregnancy, 22-40 weeks) liver tissue; hALT: human adult (age 30) liver tissue.
Figure 14:
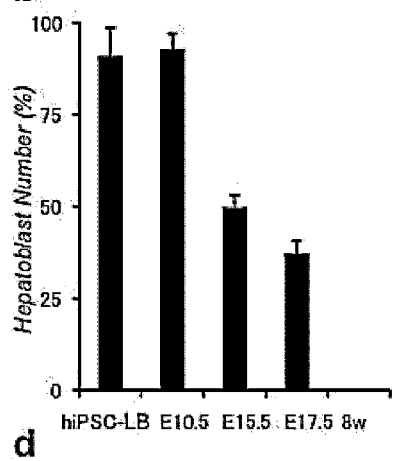
Figure 14:
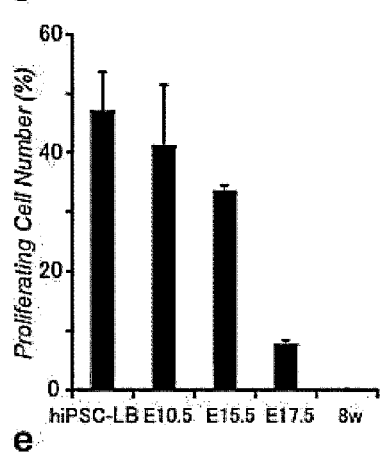
Figure 14:
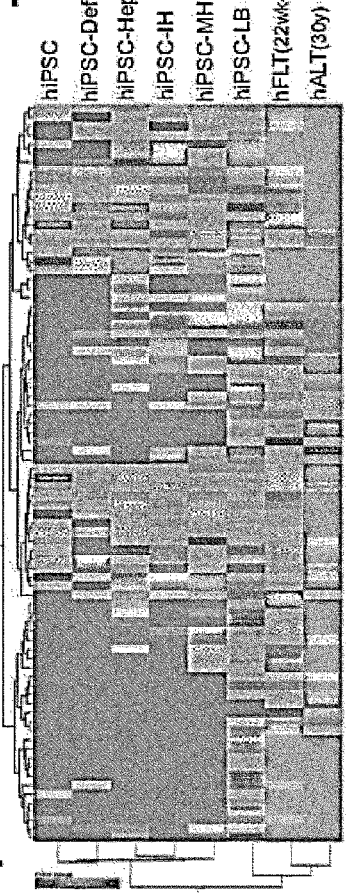
Figure 14:
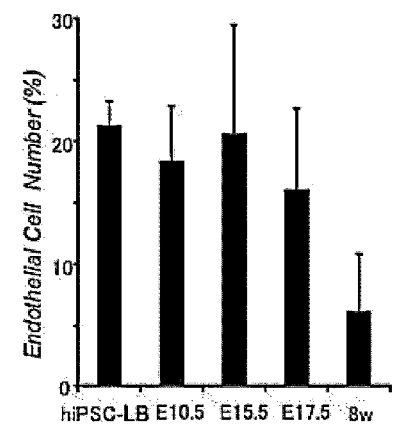
Figure 14:
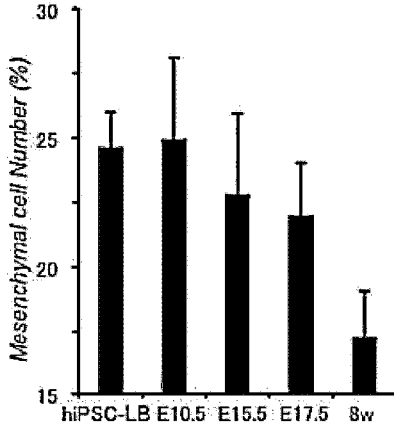
Figure 20:
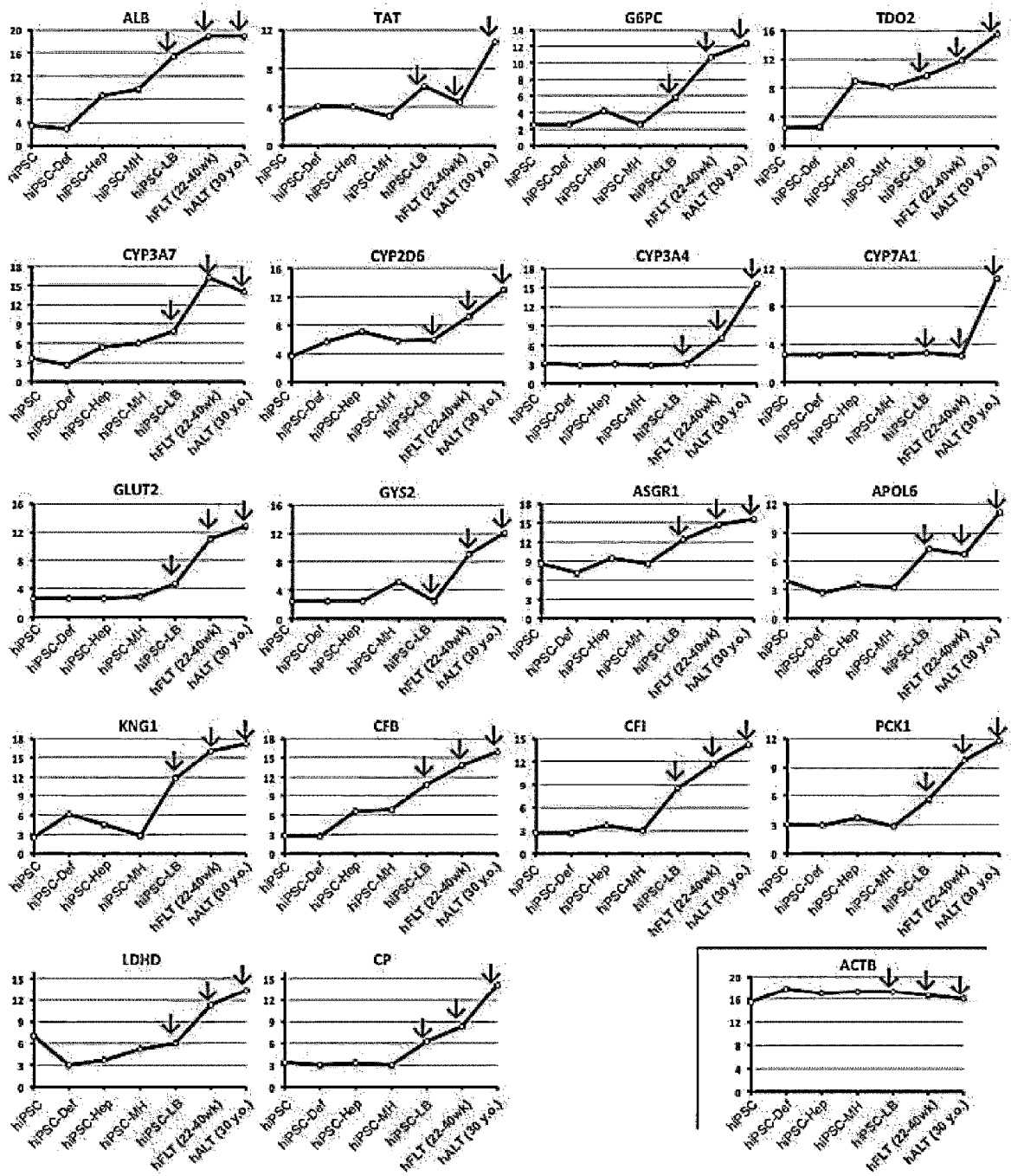
FIG. 20 Expression profiling of representative hepatic marker genes by microarray analysis
Gene expressions of hiPSC-LBs were in an appropriate stage, compared with those of human fetus (22-40 gestational week) and human adult (30 years old) liver tissues. TAT: tyrosine aminotransferase; G6PC: glucose-6-phosphatase; $TDO^2$: tryptophan 2,3-dioxygenase; GLUT2: glucose transporter 2; GYS2: glycogen synthase 2; APOL6: apolipoprotein L; KNG1: kininogen 1; CFB: complement factor B; CFI: complement factor 1; PCK1: phosphoenolpyruvate carboxynase; LDHD: lactate dehydrogenase D; CP: ceruloplasmin; ACTB: actin beta.

Unlike advanced livers as found in late pregnancy or post-natal mice, hiPSC-LBs were largely similar to E10.5 mouse LBs (mLBs) (FIG. 14a). Like mesenchymal and endothelial progenitor cells, hiPSC-LBs and E10.5 mLBs are composed of bipotential, proliferative hepatoblasts which express AFP[14,15]. In hiPSC-LBs and E10.5 mLBs, 90% or more of the presumed liver cells expressed AFP, whereas no AFP expression was observed in E15.5 and E17.5 mLBs (FIG. 14b). Liver cells in hiPSC-LBs had a proliferating capacity comparable to that of E10.5 mLBs (FIG. 14c). Further, hiPSC-LBs were composed of mesenchymal and endothelial progenitor cells in similar proportions to those seen in E10.5 mLBs (FIG. 14d, e). To characterize gene expression, 83 genes that are serially upregulated during liver development were selected and their expressions were studied by microarray RNA profiling. It was described previously[16,17] that E10.5 mLBs correspond to human fetal liver of gestational week 3 to 4 (3-4 GW). Consistent with this, the gene expression patterns of the 83 genes in hiPSC-LBs were recognized to be in an appropriate differentiation stage, as compared with gene expressions in more advanced liver tissues derived from fetuses of 22-40 GW and adults (FIG. 14f and FIG. 20).

Figure 15:
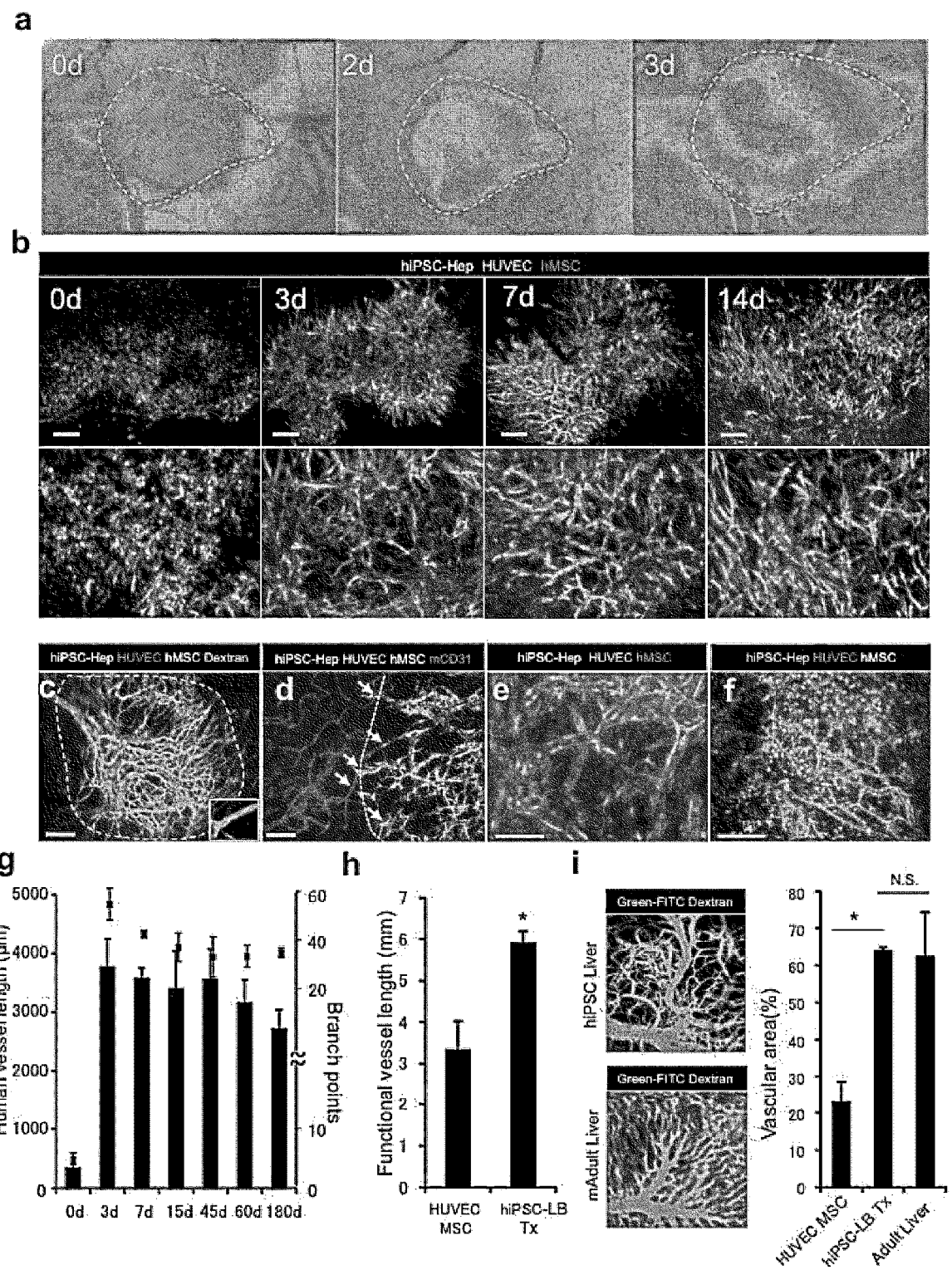
FIG. 15 Generation of human liver tissue with in vivo functional vascular networks
(a) hiPSC-LBs were transplanted into a cranial window of NOD/SCID mouse. When the transplanted hiPSC-LBs were observed macroscopically, blood flow into human vessels was recognized within about 48 hours after transplantation. Dotted area indicates the transplanted hiPSC-LB. Scale bar, 1 mm. (b) Chronological live observation under confocal microscope revealed formation of vascular networks by vascular endothelial cells in the hiPSC-LBs. (c) Intravenous injection of dextran showed that hiPSC-LBs were completely perfused through functional human vascular networks by day 3 post-transplantation. This panel shows connections between human and mouse vessels. Dotted line indicates the end of the transplant. Scale bar, 500 µm. (d) Connections between HUVECs (green, GFP) and host vessels (blue, Alexa647-labeled mouse-specific CD31, intravenous injection) are directly visualized. Scale bar, 250 µm. (e, f) Localization of hMSCs- or hiPSC-derived cells in the formed liver tissue was observed at day 15 post-transplantation. Scale bar, 100 μm (e) and 250 μm (f). (g) Quantitative analysis of human vessels in vivo in hiPSC-LB transplant (results are shown as means+S.E.M., n=3). (h) Lengths of functional vessels were compared between hiPSC-LB and HUVEC hMSC transplants (Tx). (Results are shown as means+S.E.M., n=5, *: P<0.01). (i) Intravital confocal observation after infusion of FITC-dextran. Vascularization in hiPSC-LB-derived tissue is almost equivalent to that in normal adult mouse liver. (Results are shown as means±S.E.M., n=5, *: P<0.01).
Figure 21:
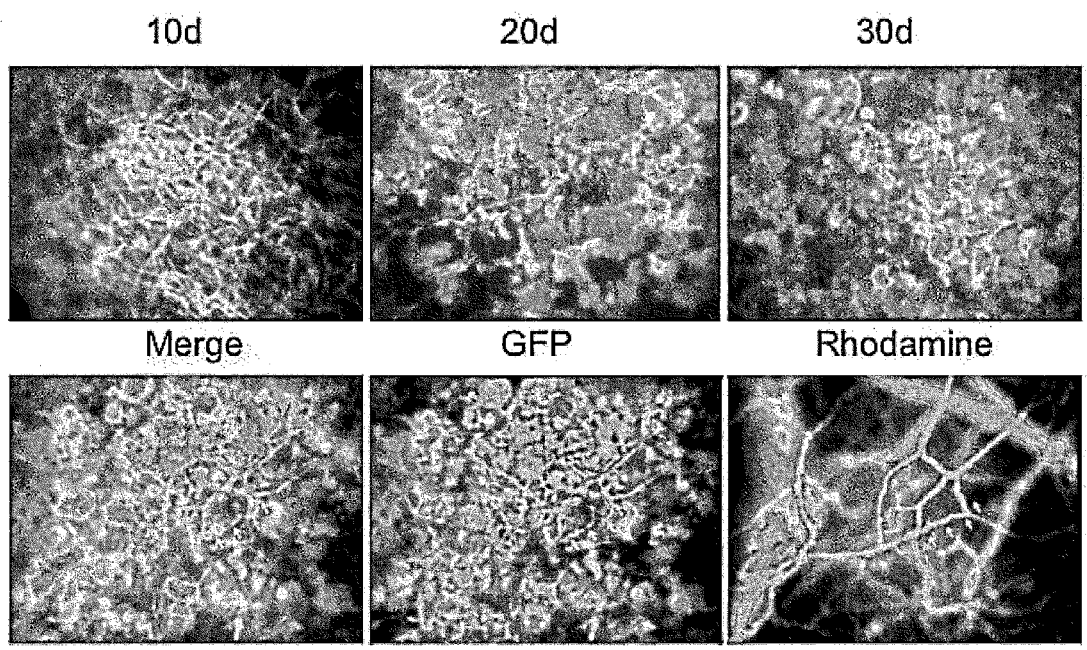
FIG. 21 Generation of murine liver tissue from mouse liver bud-derived cells.
(a) Chronological intravital fluorescence imaging of EGFP-labeled E13.5 mFLC transplants. At day 30 post-transplantation, tetramethylrhodamine-conjugated dextran was injected via the tail vein to reveal functional blood vessels.
(b) HE staining of generated murine liver tissue. Hepatocyte clusters contained sinusoidal endothelial cells (right, arrowhead). Cytokeratin immunostaining confirmed the formation of bile duct-like structures inside the clusters (right, lower panel).
Figure 21:
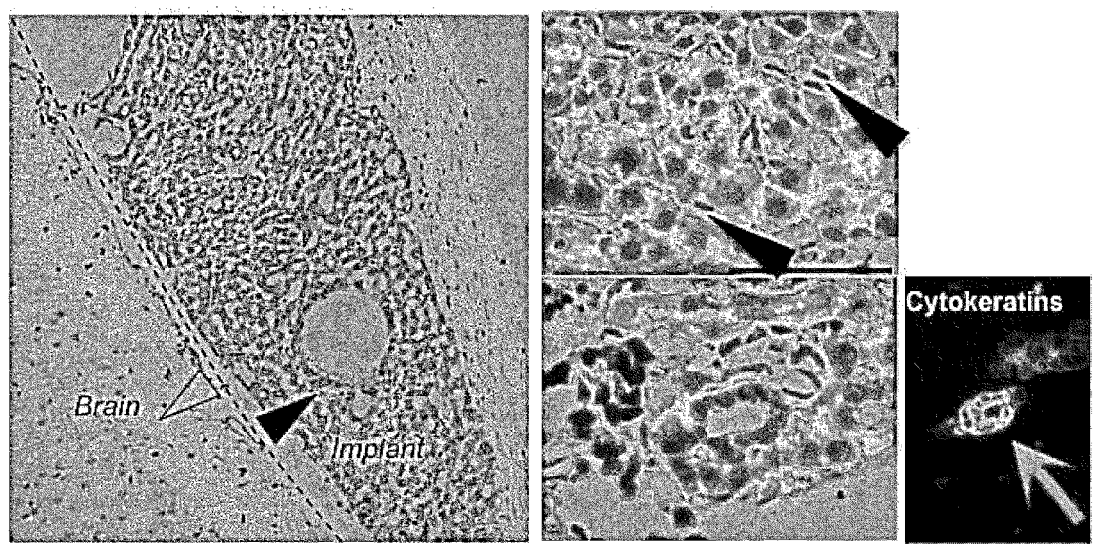
Figure 22:
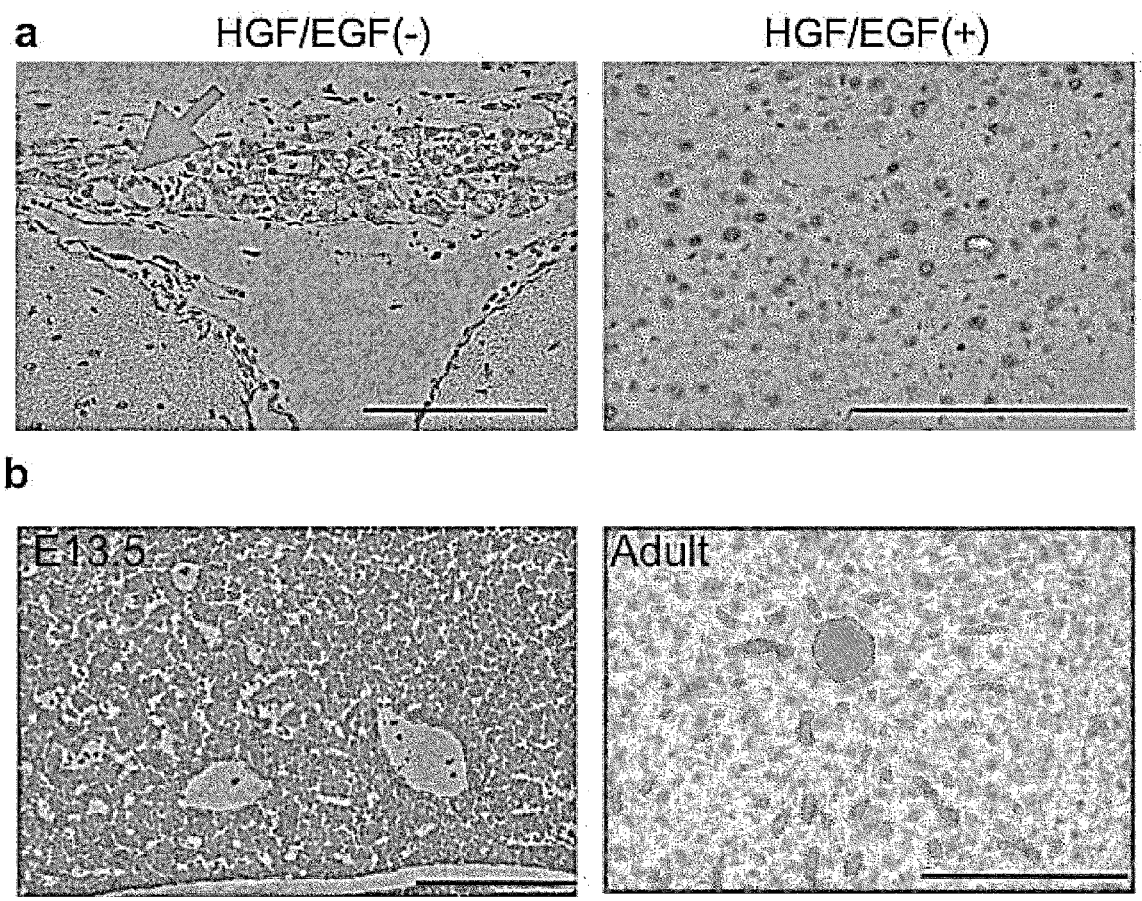
FIG. 22 Histological comparison among generated murine liver tissue, E13.5 fetal liver tissue and adult liver tissue
(a) Addition of HGF (500 ng/ml) and EGF (200 ng/ml) enhanced the recapitulation of liver tissue.
(b) The generated murine liver tissue had histological characteristics similar to those of adult liver tissue rather than those of E13.5 fetal liver tissue. Bars, 200 μm.
Figure 23:
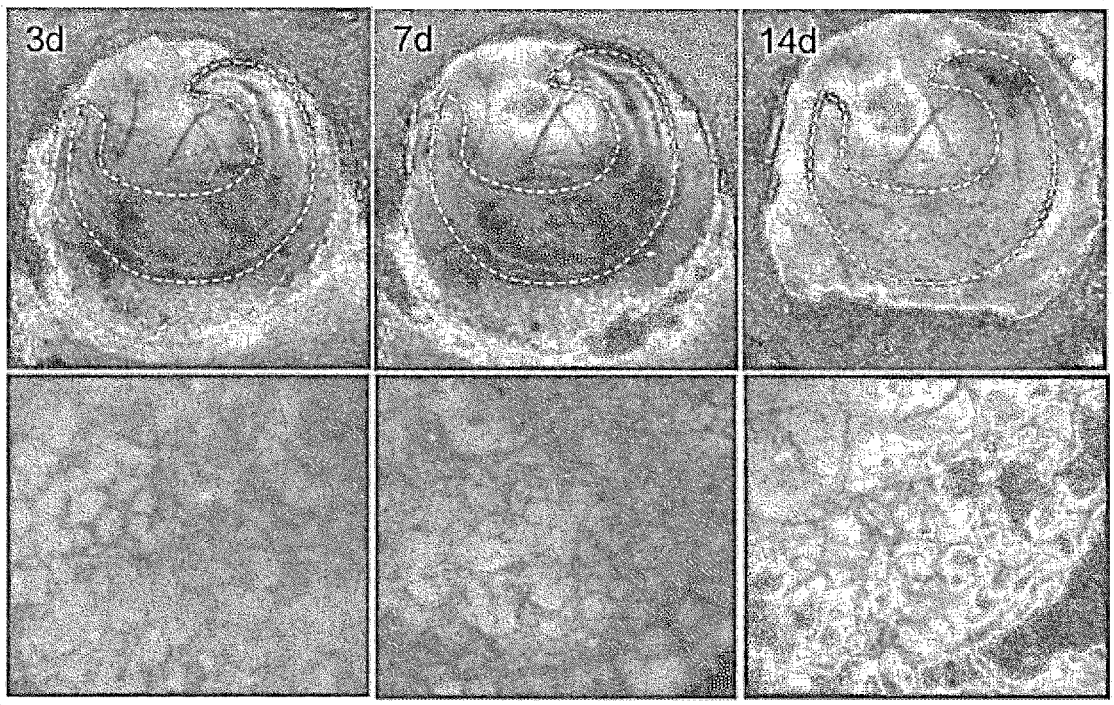
FIG. 23 In vivo transplantation of hFLC-LBs
In vivo grown hFLC-LBs were transplanted under the cranial window of NOD/SCID mice.
(a) Chronological macroscopic images showing the progress of vascularization. Functional blood flow began at day 3, and vessels became more sophisticated and stabilized over time.
(b) Intravital confocal images of hFLC-LB derived tissues at day 3. Green: hFLCs expressing EGFP; red, HUVECs expressing KOFP. Bar, 100 μm.
Figure 23:
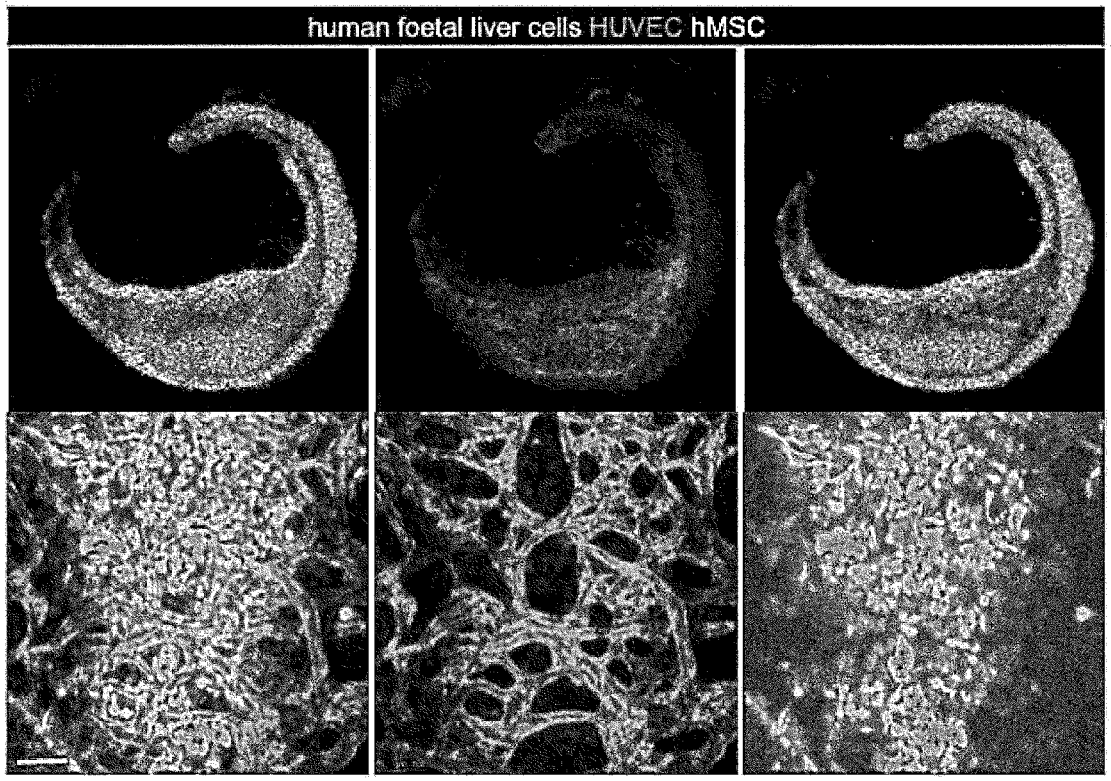
Figure 24:
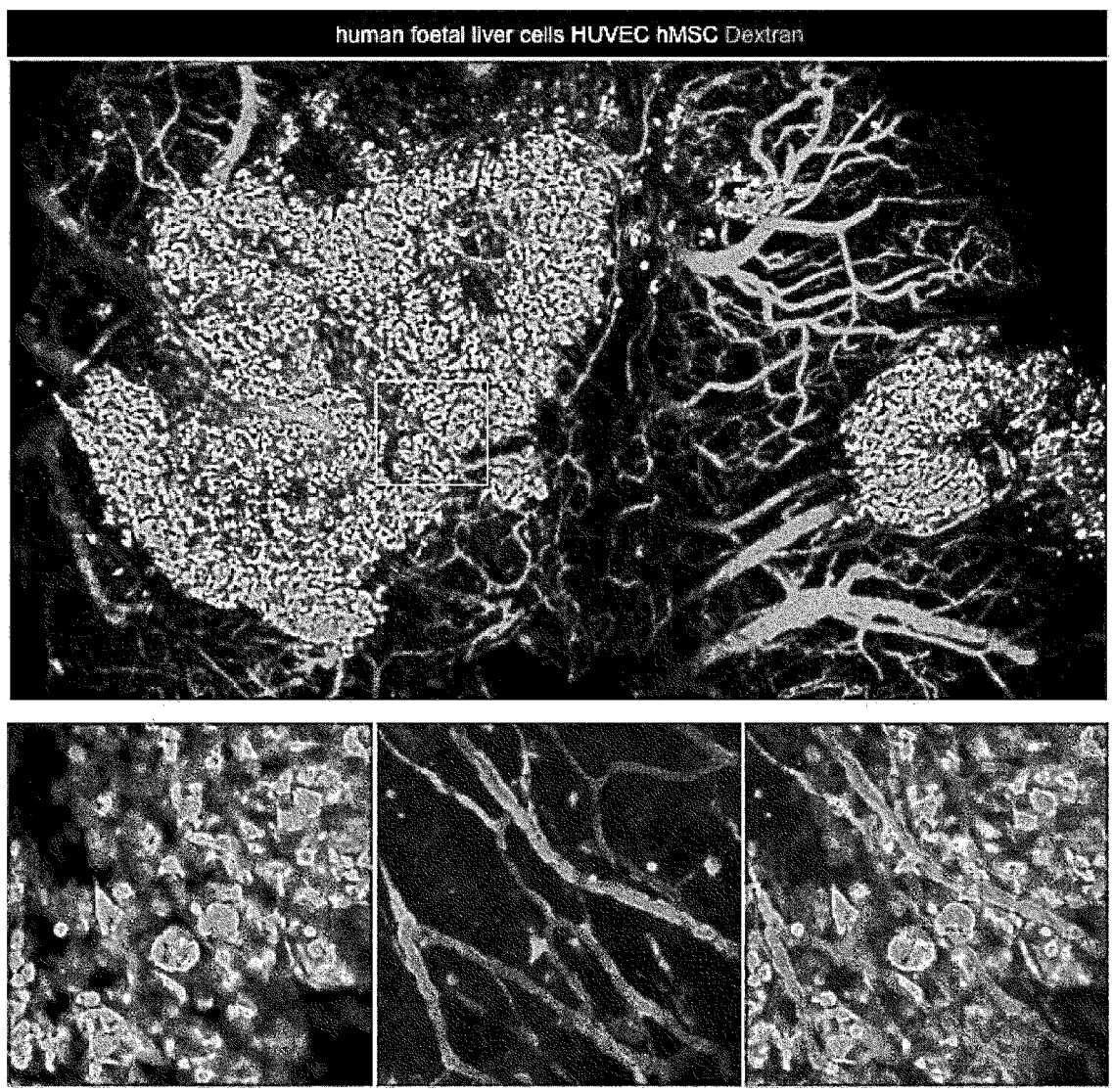
FIG. 24 In vivo formation of functional vascular networks inside the hFLC-derived liver tissue.
Patent vasculature shown by Texas Red-conjugated dextran infusion at day 3.
Figure 25:
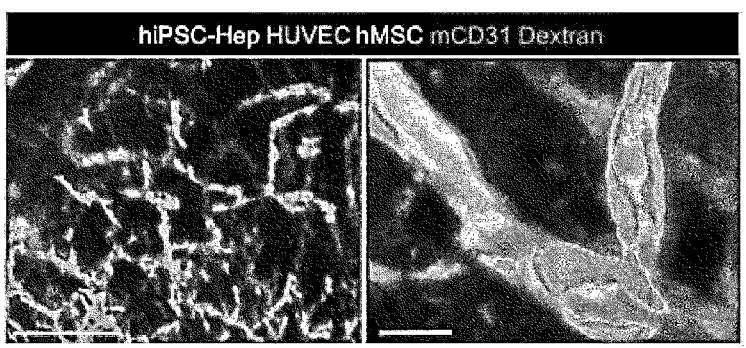
FIG. 25 Formation of human vascular networks connected with host vessels is essential for successful hiPSC-Hep engraftment.
(a) Direct visualization of the connections between HUVECs (green, GFP) and host vessels (blue, Alexa647-conjugated mouse-specific CD31, injected i.v.). Perfused vessels were visualized by i.v. injection of fluorescence-conjugated dextran (red) at day 10. Bar, 250 μm and 25 μm.
(b) Species-specific CD31 immunostaining of explanted hiPSC-LB transplants showing direct connection between human and mouse vessels in hiPSC-derived liver tissues. Bar, 100 μm
(c) Macroscopic images of hiPSC-hMSC transplants without endothelial cells at multiple time points. No identifiable blood vessels are visible.
(d) HE staining of hiPSC/hMSC transplants showed fibrotic tissue formation at day 30 post-transplantation. This result indicates the failure of hiPSC-derived hepatic cell engraftment, suggesting the necessity of endothelial cells. Bars, 100 μm.
Figure 25:
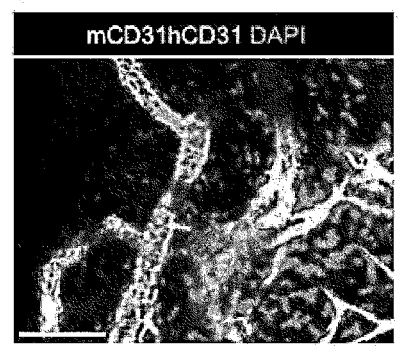
Figure 25:
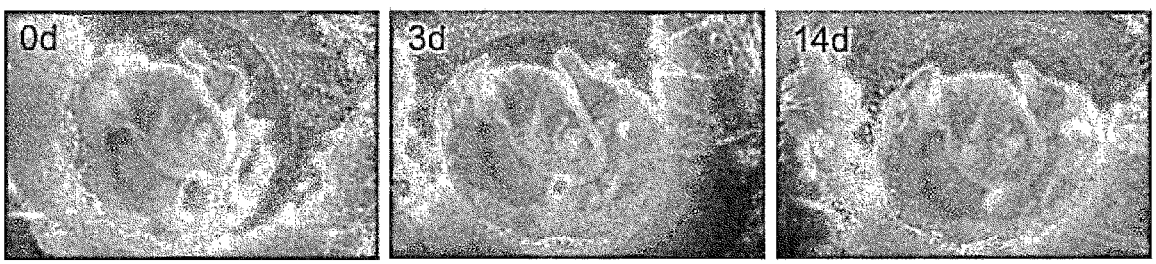
Figure 25:
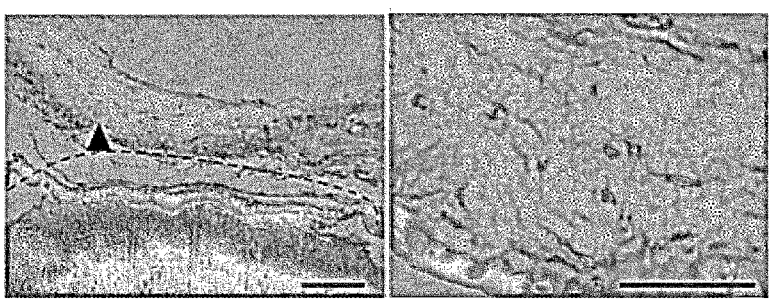
Figure 26:
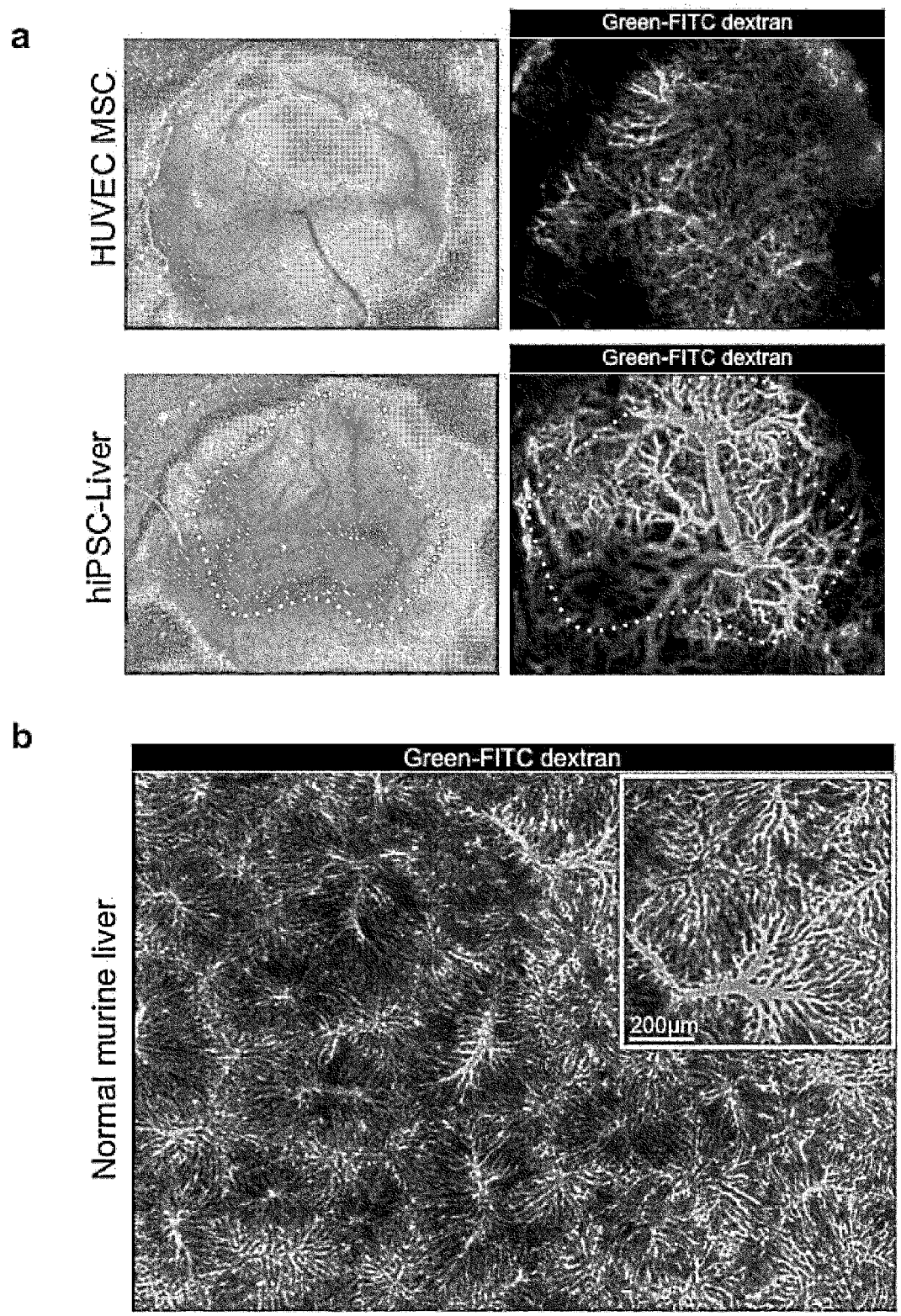
FIG. 26 Intravital imaging of generated human liver and normal murine liver vasculature in vivo.
(a) The vasculature of HUVEC hMSC alone (upper) or hiPSC-LB transplant (lower) visualized by FITC-conjugated dextran infusion at day 30 post-transplantation.
(b) Live imaging of normal murine liver where blood flow is visualized with FITC-conjugated dextran. Bar, 200 μm.
Figure 27:
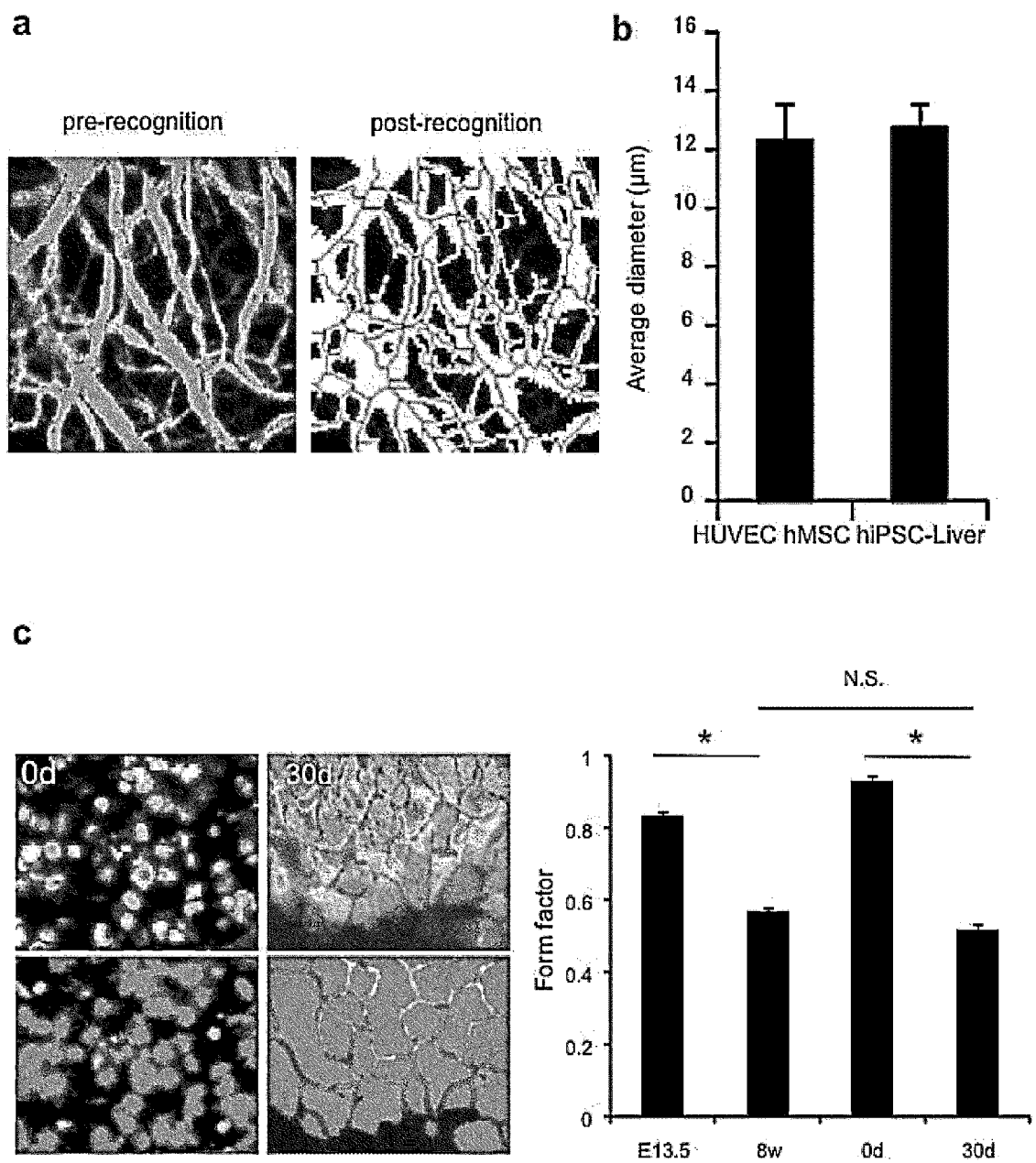
FIG. 27 Intravital evaluation of the human vascular networks and hepatocyte morphology inside liver tissue
(a) Functional human vessels visualized by FITC-conjugated dextran infusion. Image projection (left panel) was then processed using MetaMorph Angiogenesis Module software. Right panel shows representative segmentations of each image.
(b) Determination of vessel diameters (means±S.D.; n=3).
(c) Intravital images of the hepatocyte morphology inside hiFLC-LB transplants and estimate of cell roundness (form factor). (Results are shown as means±S.E.M.; n=3; more than 100 cells were measured for each sample; *: $P<0.05$; N.S.: not significant.)

Haemodynamic stimulation is essential for liver-bud maturation[18]. To test whether hiPSC-LBs are capable of reconstituting completely functional liver tissue, liver buds were transplanted into a cranial observation window which enables repetitive imaging for a long term[19]. First, it was confirmed by using mouse liver bud-derived cells (mLB) in transplantation experiments that this model is capable of recapitulating the maturing process of LB (Supplementary Discussion; FIGS. 21 and 22). Further, in the culture, fetal liver cells having comparable LB (hFLC-LBs) forming capacity was used as a control (FIG. 18a). To track the in vivo fate of transplanted human cells, repeated live imaging of hiPSC-LB-derived tissues was performed at multiple time points. Notably, in vitro derived hiPSC-LBs connected quickly with host vasculatures within 48 hours of transplantation (FIG. 15a, b and FIG. 23). Infusion of fluorescein-conjugated dextran or Alexa 647-labeled mouse-specific CD31 antibody revealed that human blood vessels in the transplanted hiPSC-LBs connect with host vessels at the edge of the transplants. This result was also confirmed by whole mount immunostaining of explants (FIG. 15c, d; FIG. 24; FIG. 25a, b). Further, hiPSC-Heps transplanted without endothelial cells failed to vascularize and engraft, indicating that functional vessel formation was essential for the transplantation and expansion of hiPSC-LBs (FIG. 15f and FIG. 25). Human vessels stabilized by hMSC-derived perivascular cells remained for at least 180 days (FIG. 15e, g). Interestingly, the vascular networks of hiPSC-LB transplants were comparable in density to those of adult livers having a similar morphology. On the other hand, the vasculatures in the transplants composed of only HUVECs and hMSCs were less dense than those in hiPSC-LB transplants, though functional vessels were of similar diameter (approximately 12 μm) in both settings (FIG. 15h, i; FIG. 26; FIG. 27). Further, with the use of intravital imaging, it was found possible to estimate the state of differentiation based on the morphology of liver cells (FIG. 27c and Supplementary Discussion). Recently, results from detailed studies on genetically modified animals suggest that endothelial cells not only form passive conduits to deliver nutrients and oxygen but also establish an instructive vascular niche which stimulates liver organogenesis and regeneration through production of paracrine trophogens[8,20,21]. With such a transplantation model, it can be said that a unique intravital monitoring system even applicable to human tissue has been established for evaluating maturation and differentiation processes during organogenesis. Further studies are expected to elucidate the previously uncharacterized roles of human stromal cell strains during organogenesis which recapitulate physiological liver formation more precisely.

Figure 16:
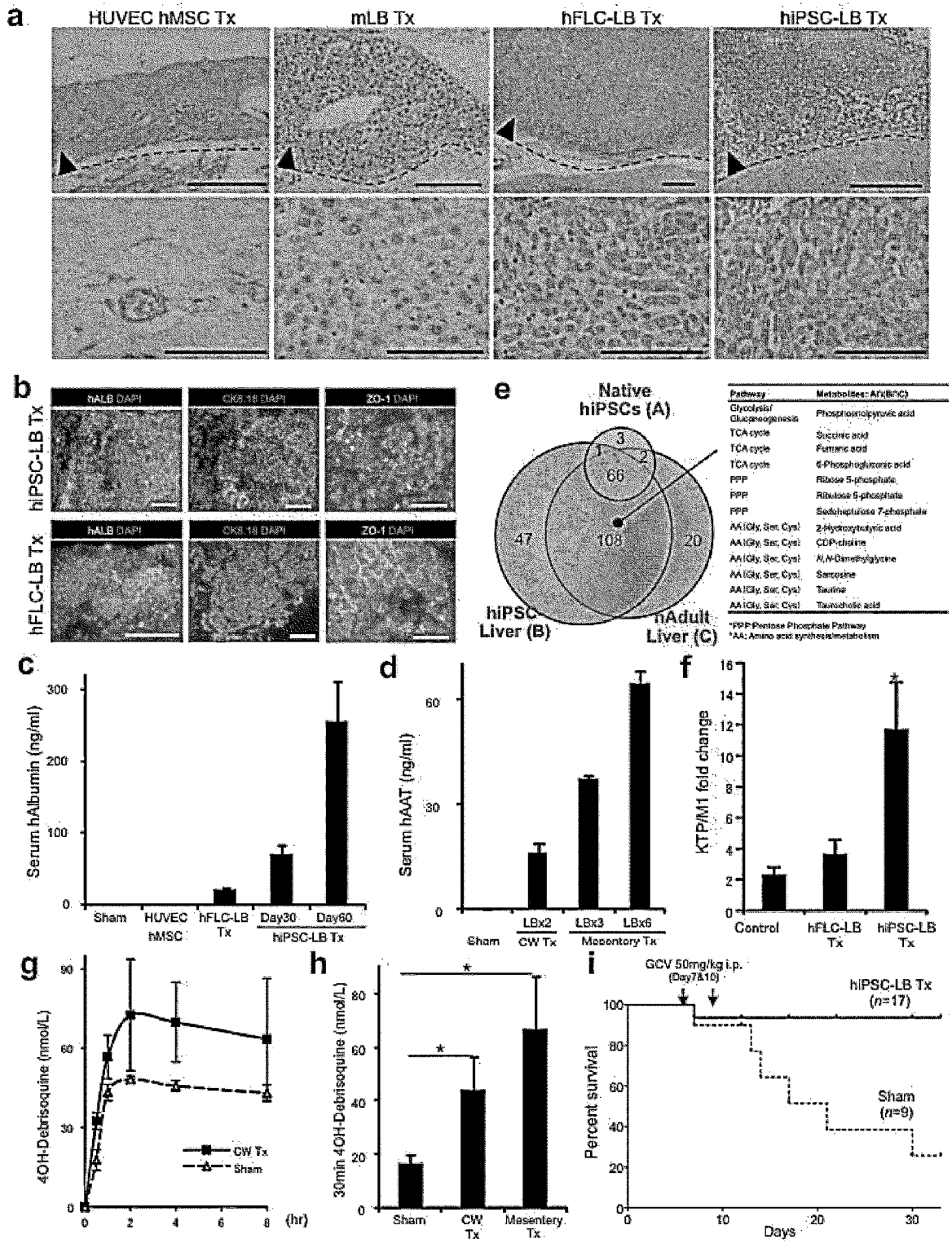
FIG. 16 Functional analysis of hiPSC-derived liver tissue.
(a) HE staining of tissue sections at day 60 post-transplantation showed formation of hepatic cords containing sinusoid-like endothelial cells, whereas such formation was not recognized in HUVEC hMSC transplants (Tx). Dotted line indicates the border of the transplant on the brain. Scale bars, 200 μm (upper panels) and 100 μm (lower panels). (b) Immunostaining showing the expressions of hepatic markers in hiPSC-LB- and hFLC-LB-derived tissues. Scale bars, 100 μm (left, middle) and 25 μm (right). (c, d) Levels of human ALB and AAT in mouse serum over time. (Results are shown as means±S.E.M., n=6 in c and n=3 in d). ATT production was proportional to the number of hiPSC-LB transplants. Two LBs were transplanted into the cranium and 3 or 6 LBs were transplanted into the mesentery. (e) Venn diagram showing the metabolic profiles of hiPSC-LB transplants measured by CE-TOFMS (FIG. 31). Of the metabolites found in hi-PSC-LB transplants, 78% was consistent with those found in adult liver. Right panel shows major metabolites which were found in both hiPSC-LB transplants and normal human adult liver, and not found in original hiPSCs. (f) Human-specific ketoprofen metabolite detected in mouse urine by mass-spectrometry. (Results are shown as means+S.E.M., n=3, *: P<0.05). (g) Formation of serum metabolite 4-OHDB in debrisoquine-administered mice (oral administration) was examined by pharmacokinetic analysis. (h) Formation of serum metabolite 4-OHDB was compared between intracranially transplanted (CW) and mesenterically transplanted mice. (Results are shown as means+S.E.M., n=3, *: P<0.05). (i) Kaplan-Meier survival curves of TK-NOG mice after hiPSC-LB transplantation. Wilcoxon statistical analysis showed a significant difference between curves of the sham-operated control group and the hiPSC-LB transplanted group (P=0.0120).
Figure 28:
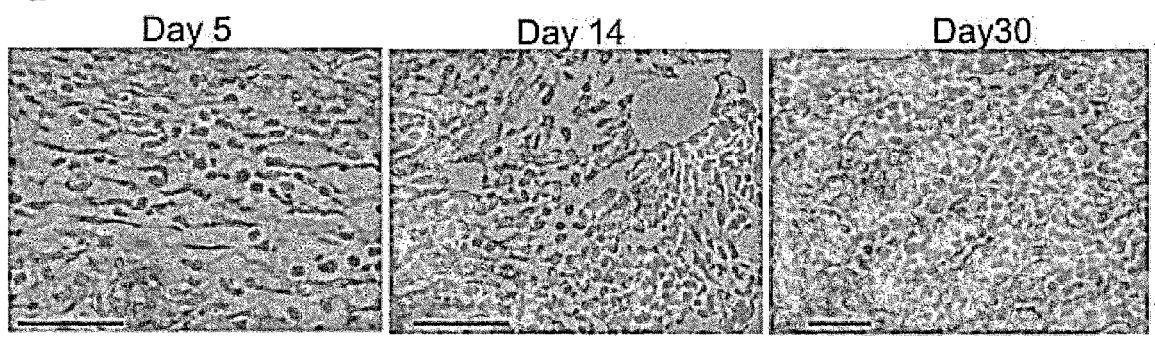
FIG. 28 Time course-dependent changes of hiPSC-LB transplants in vivo.
(a) Long-term HE staining of hiPSC-LB transplants. Round shaped hiPSCs-derived hepatoblasts expanded extensively and differentiated into immature hepatocytes with enlarged cytoplasm, as observed in normal murine liver development[1]. Bars, 50 μm.
(b) Determination of proliferating cell count inside the hiPSC-LB transplants in vivo by Ki67 immunostaining 2 weeks and 1, 2 and 4 months post-transplantation.
Figure 28:
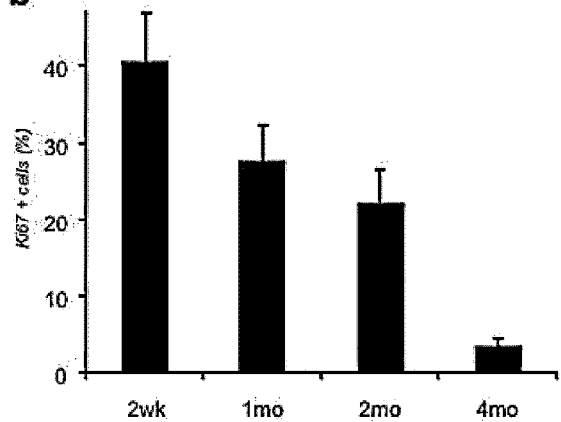
Figure 29:
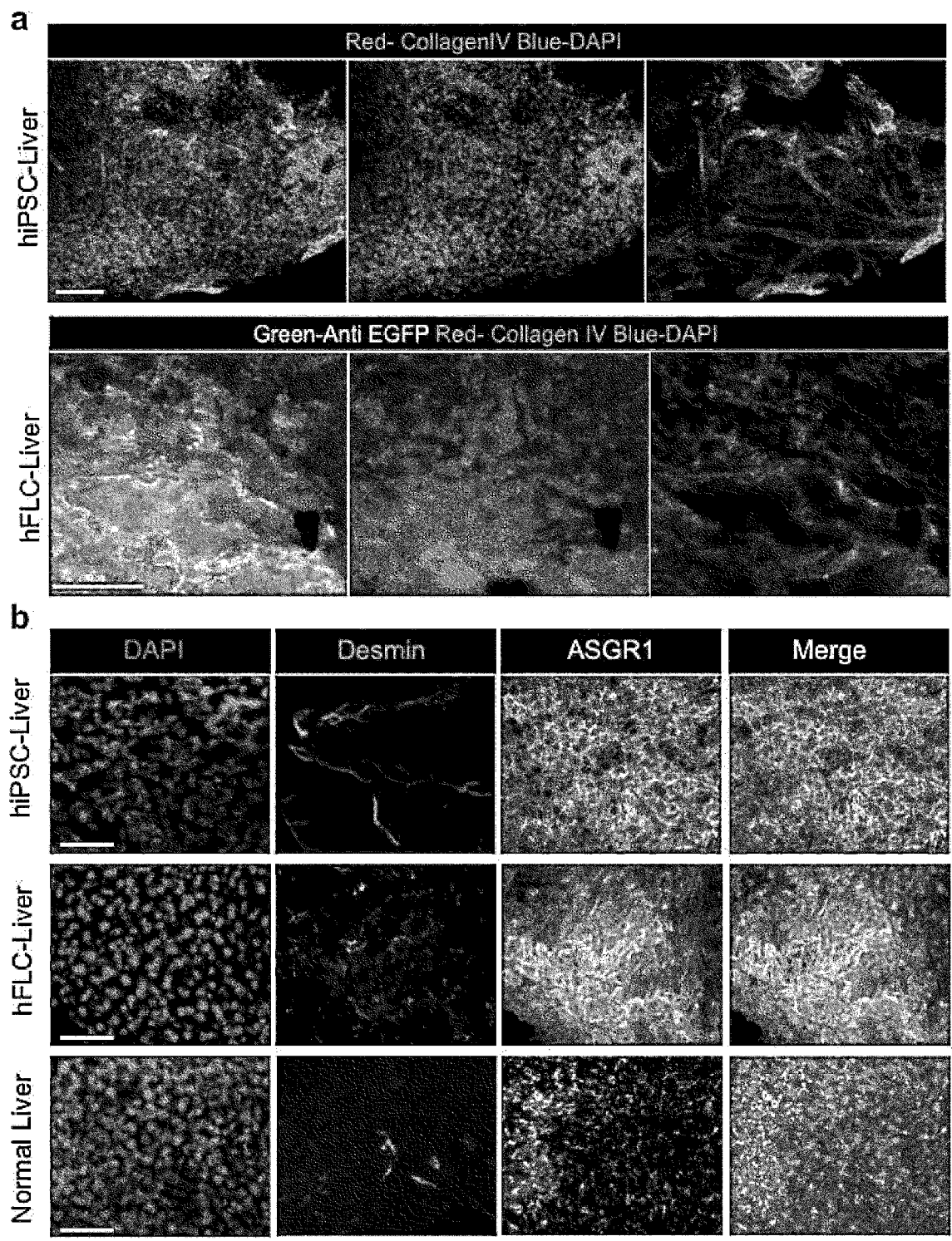
FIG. 29 Whole mount immunostaining of hiPSC-LB or hFLC-LB transplants.
(a) Collagen IV immunostaining showing the reconstitution of basement membrane protein inside the generated liver tissues. Bars, 100 μm and 50 μm.
(b) The transplant-derived human liver tissue composed of mature hepatocytes and mesenchymal cells, resembling normal murine liver tissue. Bars, 50 μm.
Figure 30:
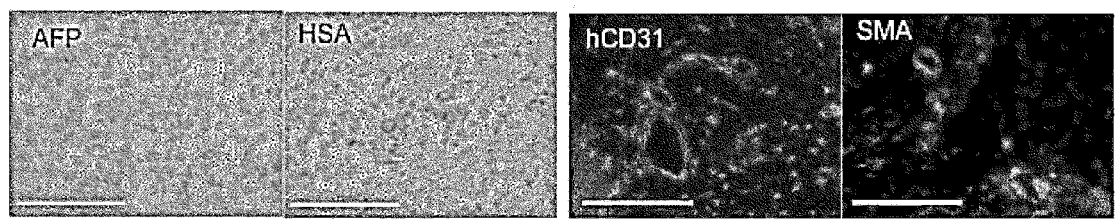
FIG. 30 Immunostaining and transmission electron microscopy analyses of hFLC-LB derived human liver tissue
(a) Liver tissue from hFLC-LB transplants expresses hepatocyte-specific antigen (HSA) but not AFP (left). Immunostaining for human CD31 and alpha-smooth muscle actin (SMA) shows the formation of major vessels inside the liver tissue (right). Bars, 100 μm.
(b, c, d, e) Electronmicroscopic images of hFLC-LB derived liver tissues. Hepatocytes with tight junctions (b, c), bile canaliculi, abundant mitochondria and glycogen & lipid accumulations (d, e) are shown.
Figure 30:
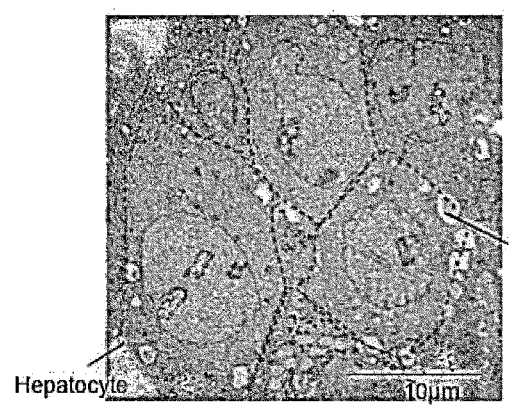
Figure 30:
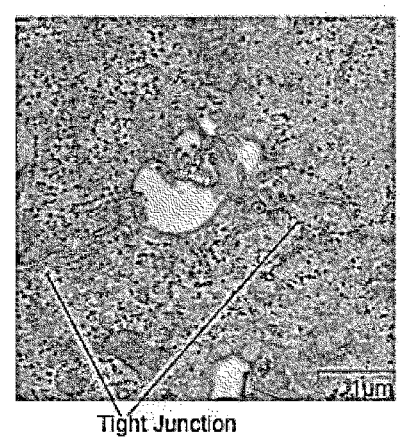
Figure 30:
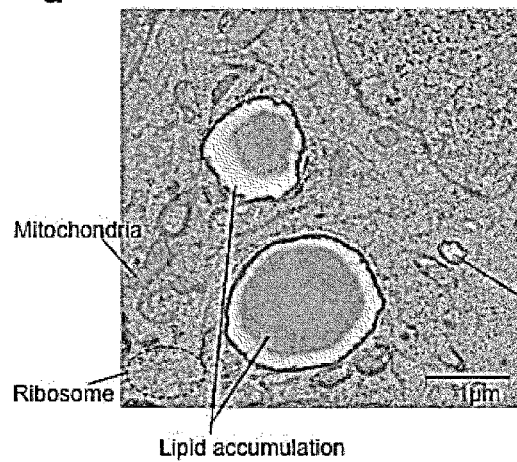
Figure 30:
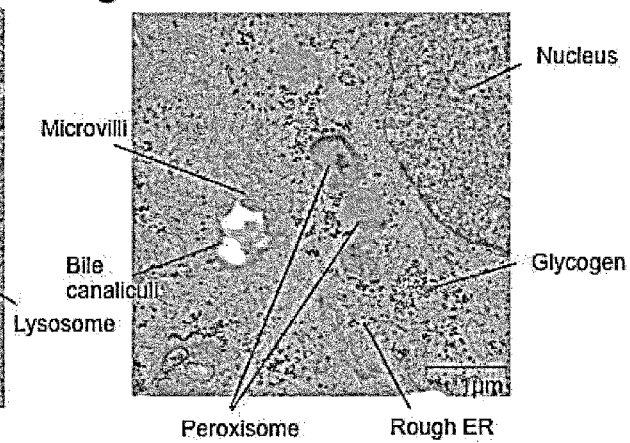

The LB transplants were examined histologically at day 60 post-transplantation. Similar to hFLC-LBs, hiPSC-LB transplants consisted of hepatic cord-like structures characteristic of adult liver (FIG. 16a and FIG. 28a). These structures were composed of cells expressing tight junction protein zona occludens 1 (ZO1), ALB and cytokeratin 8 and 18 (CK8/18) (FIG. 16b) and basement membrane containing collagen IV (FIG. 29a) which is normally found along the entire length of the sinusoid[22]. Further, the analysis revealed expression of asialoglycoprotein receptor 1 (ASGR1), a mature hepatocyte marker, and non-expression of AFP, an immature hepatocyte marker (FIG. 29b and FIG. 14a). Four months after transplantation, expression of Ki-67 (a proliferation marker) confirmed that proliferation terminated in most of the liver tissue constituting cells, just like hepatocytes in normal liver (FIG. 28b). Transplant-derived cells had the ultrastructural features characteristic of mature hepatocytes, such as well-developed oval mitochondria, formation of tight junctions, intracytoplasmic accumulation of glycogen and lipids, bile canaliculi, etc. (FIG. 30b, c, d, e).

Figure 31:
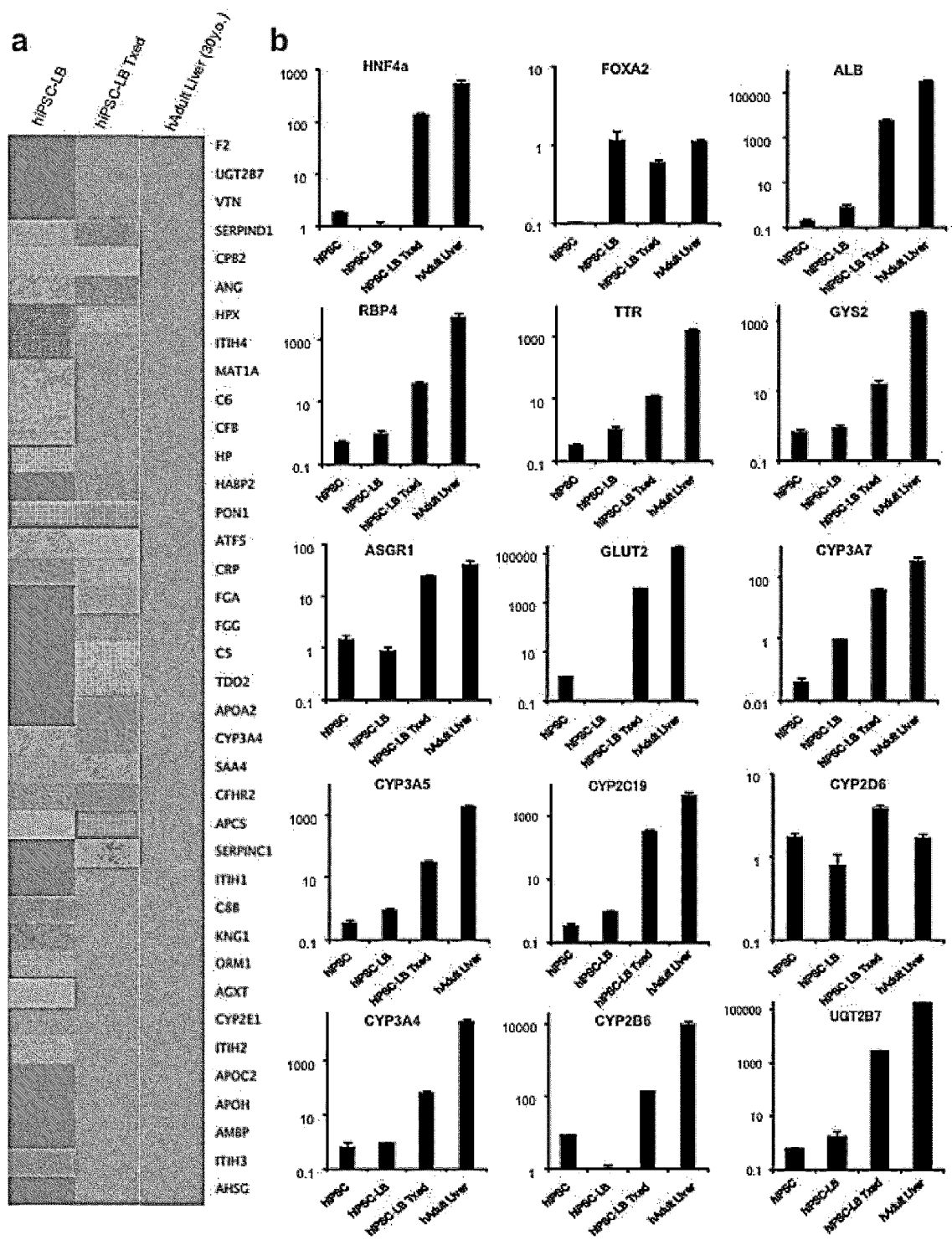
FIG. 31 Gene expression profile for hiPSC-LB transplants
(a) Microarray profiles and (b) qPCR validations of multiple hepatic maturation marker genes at day 60 post-transplantation revealed that hiPSC-LBs mature into mature hepatocytes through transplantation.
Figure 32:
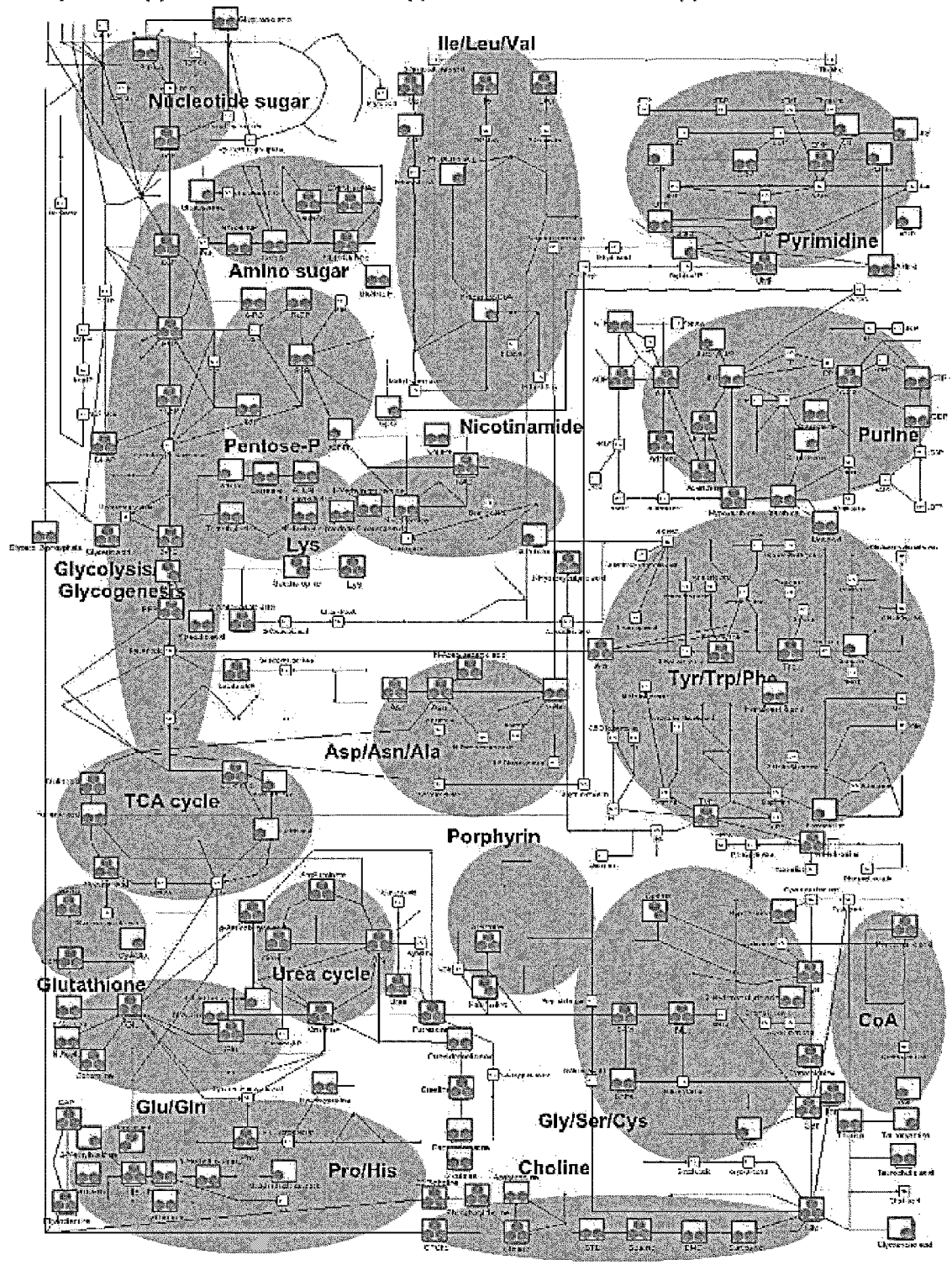
FIG. 32 Metabolic pathway maps of day 60 hiPSC-LB transplants (blue), human adult liver (red) and native hiPSCs (green).
Metabolites identified in the pathway map were indicated by different colored squares. N.D.: not detected.

Analysis of sera from hiPSC-LB-transplanted mice confirmed production and secretion of human-type ALB and A1 antitrypsin (AAT) (both are human proteins) (FIG. 16e). At day 60 post-transplantation, hiPSC-LBs were explanted and analyzed by qPCR. The results revealed significant liver maturation compared with in vitro-derived hiPSC-LBs (FIG. 31). Furthermore, to characterize the profiles of low molecular weight metabolites such as the products of sugar, amino acid and nucleotide metabolism, metabolome analysis of hiPSC-LB transplants was performed, resulting in the detection of 222 metabolites, including liver-specific metabolites such as taurocholic acid (FIG. 16F). These high metabolic profiles were similar to those of human adult liver rather than those of original hiPSCs (FIG. 32). Further, to analyze the drug metabolism activity that is a major function of the liver, the mice were challenged with ketoprofen[23] or debrisoquine[24,25], which are known to be metabolized differently in mice and humans. After the drug exposure, formation of human-specific metabolites was recognized in urine and serum samples collected from hiPSC-LB-transplanted mice (FIG. 16f, g, h and Supplementary Discussion). This result shows that it is possible to predict drug metabolism profiles of humans by using the transplanted mouse and mimicking in vivo human physiological function. This is particularly striking, since conventional methods require high quality adult hepatocytes for transplantation into a host mouse bearing severely damaged liver[26,27]. It is very significant that, in future, human-type drug responsiveness could be precisely validated by using human iPS cells.

Figure 33:
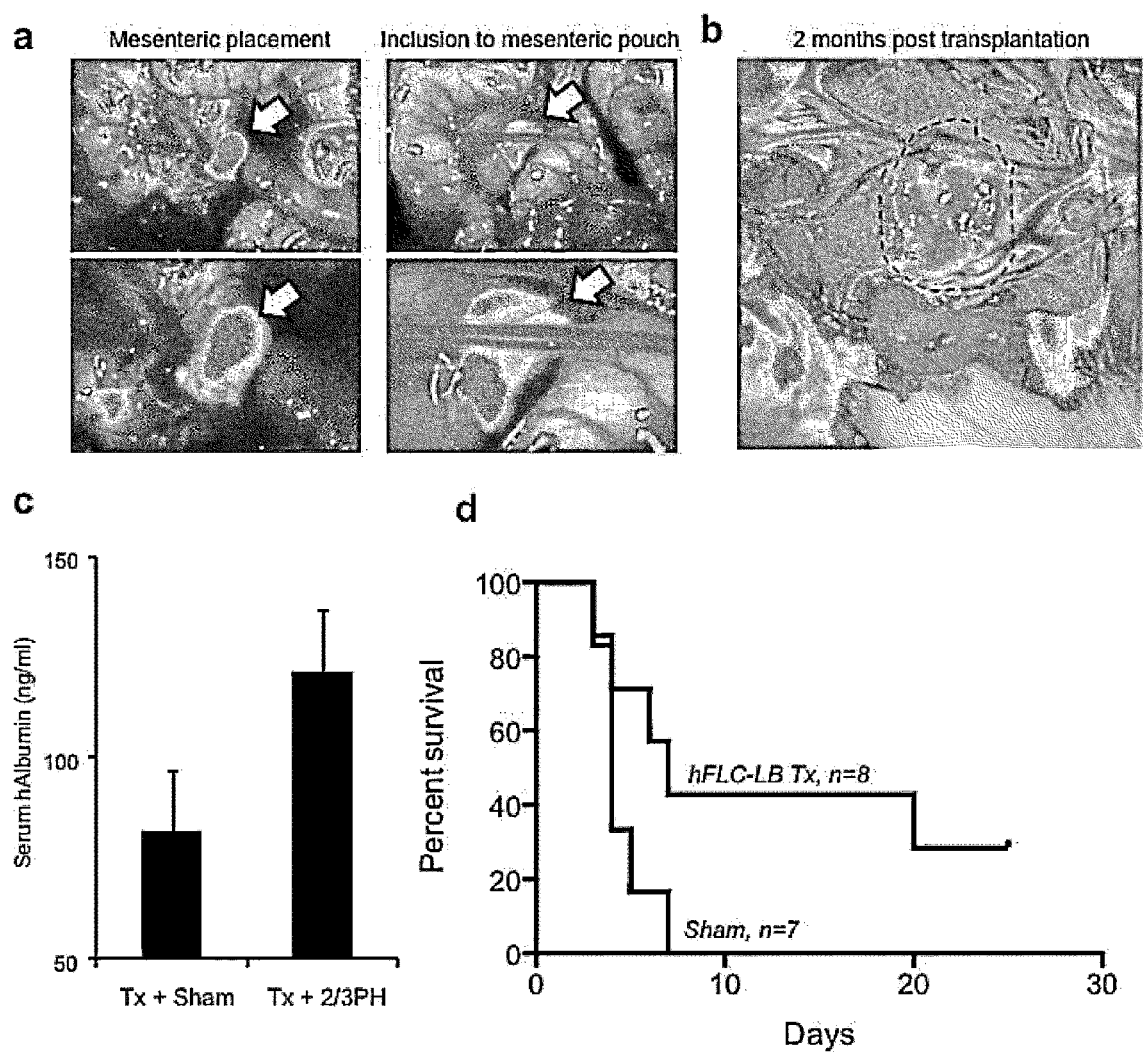
FIG. 33 Establishment of a mesenteric transplantation model towards therapeutic application.
(a) In vivo grown hiPSC- or FLC-derived LBs were transplanted onto the mesentery covered with fibrin glue.
(b) Macroscopic observation of the hiPSC-derived liver tissue at day 60 post-transplantation. Dotted area indicates the transplant.
(c) Production of human albumin increased at day 30 after hiPSC-LB transplantation by ⅔PH. (n=3)
(d) Kaplan-Meier survival curves of hFLC-LB transplanted group (n=8) and sham-operated group (n=7) in DT-infused Alb-TRECK/SCID mice.

Towards clinical application in the future, the present inventors evaluated the possibility of a minimally invasive mesenteric transplantation model; the mesentery would be a more realistic target site than the cranium. When hiPSC-LBs were transplanted onto the mesentery covered with fibrin glue, human blood vessels connected with host vessels after a month and macroscopic observation confirmed the successful engraftment of transplanted LBs on mesentery (FIG. 33a, b). The hiPSC-LBs transplanted onto mesentery had higher functions in terms of protein production and drug metabolism than when they were transplanted into the cranium. As disclosed previously[28], importance of portal circulation was supported. Further, transplantation of hiPSC-LBs improved the survival of TK-NOG mice[29] after gancyclovir-induced liver failure compared with sham-operated mice (FIG. 16i and Supplementary Discussion). Thus, the present inventors have successfully induced a vascularized and functional human liver by transplanting in vitro hiPSCs-derived LBs.

Regenerative medicine using autologous pluripotent stem cells holds extremely great promise. However, clinical trials of cell transplantation, currently an important target of the stem-cell-based approach, have presented unsatisfactory results[30,31]. The present study has demonstrated that transplantation of organ buds is effective as a novel technique for preparing a three-dimensional, vascularized organ in vivo. These results highlight the enormous therapeutic potential of in vitro-grown organ-bud transplantation for treating organ failure.

Methods Summary

Hepatic early differentiation of hiPSCs was induced based on a protocol reported previously[5]. HUVECs and hMSCs (Lonza, Basel, Switzerland) were maintained in endothelial growth medium (EGM) (Lonza) or MSC growth medium (Lonza) at 37° C. in a humidified 5% $CO_2$ incubator. To generate human LBs in vitro, $1 \times 10^6$ hiPSC-derived hepatic cells, $0.8-1 \times 10^6$ HUVECs and $2 \times 10^5$ hMSCs were suspended in a mixture of EGM and hepatocyte culture medium (HCM) (Cambrex, Baltimore, Md.) [containing dexamethasone (0.1 µM, Sigma-Aldrich, St Louis, Mo.), oncostatinM (10 ng/ml, R&D System, Minneapolis, Minn.), HGF (20 ng/ml, PromoKine) and SingleQuots (Lonza)] and plated on Matrigel (BD Biosciences, Bedford, Mass., USA). After 4 to 6 days of culture, generated hiPSC-LBs were detached, collected and transplanted into a pre-formed cranial window[19] of an immunodeficient mouse.

Methods

Cell culture and differentiation. TkDA3 human iPSC clone was kindly provided by Mr. Koji Eto and Mr. Hiromitsu Nakauchi. Undifferentiated hiPSCs were grown on mouse embryonic fibroblast cells as feeder cells. For endodermal differentiation, hiPSCs were seeded on a Matrigel-coated dish, transferred to RPMI1640 medium with 1% B27 without insulin and (100 ng/ml), and cultured for 5 to 6 days. For hepatic specification, hiPSC-derived endodermal cells were treated further with RPMI1640 containing hbFGF (10 ng/ml), hBMP4 (20 ng/ml) and 1% B27 for 3 to 4 days. Recombinant human activin A/EDF was kindly provided by Mr. Yuzuru Eto (Ajinomoto Co.). hFLCs (CS-ABI-3716; Applied Cell Biology Research Institute) were plated on collagen IV-coated 6-well plates (BD Biosciences) and cultured in the standard medium of the present inventors' lab (1:1 mixture of DMEM and F-12 (Sigma Aldrich) supplemented with 10% FBS (Lot 7219F; ICN Biochemical, USA), 50 mmol/L HEPES (Wako Pure Chemical Industries, Japan), 2 mmol/L L-glutamine (Life Technologies Corporation, USA), 50 mmol/L 2-mercaptoethanol (Sigma), 1× penicillin/streptomycin (Life Technologies), 10 mmol/L nicotinamide (Sigma), 1×10 M Dexamethasone (Sigma) and 1 µg/ml insulin (Wako)). Human recombinant HGF (50 ng/ml) and EGF (20 ng/ml) (Sigma) were added before cultivation. HUVECs and hMSCs (Lonza) were maintained in endothelial growth medium or MSC growth medium (Lonza) at 37° C. in a humidified 5% $CO_2$ incubator.

Retroviral transduction. For live imaging, cells were infected with retroviruses expressing EGFP or Kusabira-Orange (KOFP) as described[19]. In brief, a retrovirus vector pGCDNsam IRES-EGFP or KOFP was transfected into 293 gp and 293 gpg packaging cells (kindly provided by Mr. Masafumi Onodera), in which viral particle production was induced using a tetracycline inducible system. Culture supernatants of retrovirus-infected cells were passed through a 0.45-µm filter (Whatman, GE Healthcare, Japan) and used immediately for infection. KOFP displays a major absorption wavelength maximum at 548 nm with a slight shoulder at 515 nm and emits a bright orange fluorescence with a peak at 561 nm[32].

Transplantation. In vitro-generated LBs were detached, collected and transplanted into a pre-formed cranial window of a severely immunodeficient (NOD/SCID) mouse (Sankyo Lab. Co., Tsukuba, Japan). The in vivo fate of transplanted cells was monitored by intravital imaging using a fluorescence microscope (model BZ-9000; Keyence, Osaka, Japan) or the Leica TCS SP5 confocal microscope (Leica Microsystems). For survival curves, TK-NOG mice (body weights <20 to 30 g) were used in this study (supplied by the Central Institute for Experimental Animals, Kanagawa, Japan)[29]. Ganciclovir (GCV, 50 mg/kg, intraperitoneal), a drug that is not toxic to human or mouse tissues, was administered to induce tissue-specific ablation of transgenic liver parenchymal cells at day 7 and 10 after a dozen hiPSC-LBs were transplanted on the mesentery. The mice were bred and maintained according to the Yokohama City University institutional guidelines for the use of laboratory animals.

Quantification of perfusion brought about by engrafted vessels. Tail vein injections of 1% tetramethylrhodamine-conjugated dextran (2,000,000 MW), fluorescein-isothiocyanate-conjugated dextran (2,000,000 MW) and Texas-Red-conjugated dextran (70,000 MW, neutral) were used to identify vessel lumens (all from Invitrogen, Carlsbad, Calif., USA). Confocal image stacks were acquired for the implanted vessels and dextran. Image projections were processed using MetaMorph Angiogenesis Module software (Molecular Devices, Union City, Calif., USA). Total tubule length, the percentage of tubules per field and tube diameter were then logged automatically into an Excel spreadsheet.

Gene-expression analysis. Quantitative PCR analyses were conducted as described previously[33]. Total RNA of human fetal liver (Lot No. A601605) and human adult liver (Lot No. B308121) were obtained from Biochain Institute (Hayward, Calif., USA).

Gene expression microarray and data analysis. Total RNA was prepared from hiPSC-derived cells/tissues (hiPSC, hiPSC-Def, hiPSC-Hep, hiPSC-IH, hiPSC-MH, hiPSC-LB, hiPSC-LB-Tx) using an RNeasy Mini Kit (Qiagen, Valencia, Calif.). Total RNA of human fetal liver (Lot No. A601605) and human adult liver (Lot No. B308121) were obtained from Biochain Institute (Hayward, Calif., USA). cRNA was amplified, labeled using Low Input Quick Amp Labeling Kit (Agilent Technologies, Palo Alto, Calif.) and hybridized to 44K 60-mer oligomicroarray (Human Gene Expression 4×44K v2 Microarray Kit; Agilent Technologies) according to the manufacturer's instructions. Hybridized microarray slides were scanned with Agilent High-Resolution Microarray Scanner. Using Feature Extraction Software version 10.7.3.1 (Agilent Technologies), relative hybridization intensity and background hybridization value were calculated. According to the protocol recommended by Agilent Technologies and using flag standards in GeneSpring 11.5.1 Software, raw signal intensity and flag of each probe were calculated from hybridization intensity and spot information. Further, the row signal intensity of samples was log 2 converted and normalized with quantile algorithm. For all samples, probes were selected except for "compromised" flag. As a result, 34,183 probes were obtained as detected genes. Further, expression data for 26,153 genes were focused at gene level. Heat maps were prepared by GeneSpring. Normalized intensities were loaded and scaling-adjusted with the distance from the median of each probe. Samples and genes were classified using a hierarchical clustering method with Euclidean distance. To evaluate differences in gene expression patterns in hiPSCs of various stages, expression changes in the selected 83 genes were analyzed. These genes were identified in a previous study of the present inventors using microarray analyses of mouse liver cells of various developmental stages and human liver tissues of two different stages. Of all genes, 83 genes were selected as liver-specific genes because their expressions increased continuously during both murine and human liver development.

ELISA. Blood samples were allowed to clot in a centrifuge tube (approximately 5 min) at room temperature, loosened from the sides of the tube and kept at 4° C. (melting ice) for 20 min. Clotted blood was centrifuged for 10 to 15 min at 400 g, 4° C. and the serum fraction was removed, with care being taken to exclude erythrocytes or clotted materials. Human ALB and AAT in the mouse serum samples were measured using Human Albumin ELISA Quantitation Kit (Bethyl Laboratories Inc., Montgomery, Tex., USA) and human alpha 1-antitrypsin ELISA Quantitation Kit (GenWay Biotech Inc., Inc., San Diego, Calif., USA) according to the manufacturers' instructions.

Whole mount immunostaining. Mice were perfused with 4% paraformaldehyde (PFA) in PBS through cardiac puncture. The cover-glass forming the cranial window was removed, and the transplants (approximately 300 μm thick) were resected and placed in 4% PFA for 1.5 hours on ice. For immunostaining, fixed collagen gels were washed three times in PBS (10 min each), blocked with 3% BSA/0.1% Triton X-100 for 1 hour, incubated with primary antibodies at 4° C. overnight, followed by three 10-min washes in PBS/0.1% Triton X-100. The sample was incubated with secondary antibodies at 4° C. overnight, followed by three 10-min washes in PBS/0.1% Triton X-100. Tissue samples were counterstained with DAPI and mounted on glass slides in mounting media (Vector Laboratories, USA), under a cover slip. The following primary antibodies were used: mouse anti-human ZO1, mouse anti-human CD31 and rat anti-mouse CD31 (BD Biosciences), rabbit anti-mouse collagen IV (Millipore, USA) and desmin (Dako Corporation, Carpinteria, Calif.). Immunostaining was analyzed using the Leica TCS SP5 confocal microscope.

Tissue processing and immunostaining. Tissues were fixed overnight at 4° C. in 4% PFA, processed, and embedded in paraffin. Transverse sections (4 μm) were placed on MAS-coated slides (Matsunami, Osaka, Japan) for immunostaining with haematoxylin and eosin (HE) or standard histological staining. Immunostaining was preceded by autoclave antigen retrieval in citrate buffer (pH 6.0). The primary antibodies used were anti-human: CD31, smooth muscle actin, AFP, CK8/18 (all from Dako Corporation) and ALB (BD Biosciences). Tissue sections were incubated with secondary antibody Alexa Fluor (Life Technologies) for 1 hour at room temperature, followed by DAPI (Sigma) nuclear staining. The images were acquired using LSM510 laser scanning microscope (Carl Zeiss Co., Germany).

Statistical analysis. Data are expressed as the means±S.D. from three or six independent experiments. Comparisons between three or four groups were analyzed using Kruskal-Wallis test by ranks, and post-hoc comparisons were performed using Mann-Whitney U-test with Bonferroni correction. Two-tailed P values of <0.05 were considered significant.

REFERENCES

1 Klein, A. S. et al. Organ donation and utilization in the United States, 1999-2008. Am J Transplant 10, 973-986, (2010).
2 Sanal, M. G. Future of liver transplantation: non-human primates for patient-specific organs from induced pluripotent stem cells. World J Gastroenterol 17, 3684-3690, (2011).
3 Kriks, S. et al. Dopamine neurons derived from human ES cells efficiently engraft in animal models of Parkinson's disease. Nature 480, 547-551, (2011).
4 Kroon, E. et al. Pancreatic endoderm derived from human embryonic stem cells generates glucose-responsive insulin-secreting cells in vivo. Nat Biotechnol 26, 443-452, (2008).
5 Si-Tayeb, K. et al. Highly efficient generation of human hepatocyte-like cells from induced pluripotent stem cells. Hepatology 51, 297-305, (2010).
6 Jiang, H. et al. Parkin controls dopamine utilization in human midbrain dopaminergic neurons derived from induced pluripotent stem cells. Nat Commun 3, 668, (2012).
7 Cai, J. et al. Directed differentiation of human embryonic stem cells into functional hepatic cells. Hepatology 45, 1229-1239, (2007).
8 Matsumoto, K., Yoshitomi, H., Rossant, J. & Zaret, K. S. Liver organogenesis promoted by endothelial cells prior to vascular function. Science 294, 559-563, (2001).
9 Espejel, S. et al. Induced pluripotent stem cell-derived hepatocytes have the functional and proliferative capabilities needed for liver regeneration in mice. J Clin Invest 120, 3120-3126, (2010).
10 Sekiya, S. & Suzuki, A. Direct conversion of mouse fibroblasts to hepatocyte-like cells by defined factors. Nature 475, 390-393, (2011).
11 Kobayashi, T. et al. Generation of rat pancreas in mouse by interspecific blastocyst injection of pluripotent stem cells. Cell 142, 787-799, (2010).
12 Zhao, R. & Duncan, S. A. Embryonic development of the liver. Hepatology 41, 956-967, (2005).
13 Si-Tayeb, K., Lemaigre, F. P. & Duncan, S. A. Organogenesis and development of the liver. Dev Cell 18, 175-189, (2010).
14 Lee, C. S., Friedman, J. R., Fulmer, J. T. & Kaestner, K. H. The initiation of liver development is dependent on Foxa transcription factors. Nature 435, 944-947, (2005).
15 Jung, J., Zheng, M., Goldfarb, M. & Zaret, K. S. Initiation of mammalian liver development from endoderm by fibroblast growth factors. Science 284, 1998-2003, (1999).
16 Gouysse, G. et al. Relationship between vascular development and vascular differentiation during liver organogenesis in humans. J Hepatol 37, 730-740, (2002).
17 Collardeau-Frachon, S. & Scoazec, J. Y. Vascular development and differentiation during human liver organogenesis. Anat Rec (Hoboken) 291, 614-627, (2008).
18 Korzh, S. et al. Requirement of vasculogenesis and blood circulation in late stages of liver growth in zebrafish. BMC Dev Biol 8, 84, (2008).
19 Koike, N. et al. Tissue engineering: creation of long-lasting blood vessels. Nature 428, 138-139, (2004).
20 Ding, B. S. et al. Inductive angiocrine signals from sinusoidal endothelium are required for liver regeneration. Nature 468, 310-315, (2010).
21 Ding, B. S. et al. Endothelial-derived angiocrine signals induce and sustain regenerative lung alveolarization. Cell 147, 539-553, (2011).
22 Martinez-Hernandez, A. The hepatic extracellular matrix. I. Electron immunohistochemical studies in normal rat liver. Lab Invest 51, 57-74, (1984).
23 Ishizaki, T. et al. Pharmacokinetics of ketoprofen following single oral, intramuscular and rectal doses and after repeated oral administration. Eur J Clin Pharmacol 18, 407-414, (1980).
24 Yu, A. M., Idle, J. R. & Gonzalez, F. J. Polymorphic cytochrome P450 2D6: humanized mouse model and endogenous substrates. Drug Metab Rev 36, 243-277, (2004).
25 Rautio, A., Kraul, H., Kojo, A., Salmela, E. & Pelkonen, O. Interindividual variability of coumarin 7-hydroxylation in healthy volunteers. Pharmacogenetics 2, 227-233, (1992).
26 Katoh, M. et al. In vivo drug metabolism model for human cytochrome P450 enzyme using chimeric mice with humanized liver. J Pharm Sci 96, 428-437, (2007).
27 Kamimura, H. et al. Assessment of chimeric mice with humanized liver as a tool for predicting circulating human metabolites. Drug Metab Pharmacokinet 25, 223-235, (2010).

28 Chen, A. A. et al. Humanized mice with ectopic artificial liver tissues. Proc Natl Acad Sci USA 108, 11842-11847, (2011).
29 Hasegawa, M. et al. The reconstituted 'humanized liver' in TK-NOG mice is mature and functional. Biochem Biophys Res Commun 405, 405-410, (2011).
30 Mizuguchi, T., Mitaka, T., Katsuramaki, T. & Hirata, K. Hepatocyte transplantation for total liver repopulation. J Hepatobiliary Pancreat Surg 12, 378-385, (2005).
31 Dudley, S. C., Jr. Beware of cells bearing gifts: cell replacement therapy and arrhythmic risk. Circ Res 97, 99-101, (2005).
32 Sanuki, S. et al. A new red fluorescent protein that allows efficient marking of murine hematopoietic stem cells. J Gene Med 10, 965-971, (2008).
33 Kobayashi, S. et al. Reconstruction of human elastic cartilage by a CD44+ CD90+ stem cell in the ear perichondrium. Proc Natl Acad Sci USA 108, 14479-14484, (2011).

Supplementary Methods

HUVEC MSC isolation. Umbilical cord samples were obtained following the approved guidelines set forth by the ethical committee at Yokohama City University (Approval No. 13120510008). HUVECs and MSCs were simultaneously isolated from the umbilical cord as previously described[2].

mFLC isolation. E13.5 mFLCs isolated from C57BL/6-Tg CAG::EGFP (SLC, Japan) were mechanically dissociated by pipetting in Dulbecco's modified Eagle's medium (DMEM) containing 10% foetal bovine serum (FBS) (JRH Bioscience, USA). Liver cells were separated from non-parenchymal cells by several rounds of low-speed centrifugation (690 rpm/4° C. for 1 min). Dissociated cells were passed twice through a 70 μm cell strainer (Falcon, USA) to obtain single cells Quantification of engrafted hepatocyte morphology. Intravital confocal images were processed with IN Cell Investigator software (GE Healthcare, Fairfield, Conn., USA), and the states of hepatocyte differentiation were classified using a "form factor" (standard estimation of roundness which correlates perimeter with area). The thus measured values vary from 0 to 1, with 1 being taken as a complete circle.

Acquisition of metabolome profiles. At day 60 post-transplantation, hiPSC-LB transplants (n=3) were harvested and analyzed. CE-TOFMS was carried out using an Agilent CE Capillary Electrophoresis System equipped with an Agilent 6210 Time of Flight mass spectrometer, Agilent 1100 isocratic HPLC pump, Agilent G1603A CE-MS adapter kit, and Agilent G1607A CE-ESI-MS sprayer kit (Agilent Technologies, Waldbronn, Germany). The system was controlled by Agilent G2201AA ChemStation software version B.03.01 for CE (Agilent Technologies, Waldbronn, Germany). Cationic metabolites were analyzed with a fused silica capillary (50 μm i.d.×80 cm total length), with Cation Buffer Solution (Human Metabolome Technologies) as an electrolyte. The sample was injected at a pressure of 50 mbar for 10 sec (approximately 10 nl). The applied voltage was set at 27 kV. Electrospray ionization-mass spectrometry (ESI-MS) was conducted in the positive ion mode, and the capillary voltage was set at 4,000 V. The spectrometer was scanned from m/z 50 to 1,000. Other conditions were the same as in the cation analysis[3].

Anionic metabolites were analyzed with a fused silica capillary (50 μm i.d.×80 cm total length), with Anion Buffer Solution (Human Metabolome Technologies) as an electrolyte. The sample was injected at a pressure of 50 mbar for 25 sec (approximately 25 nl). The applied voltage was set at 30 kV. ESI-MS was conducted in the negative ion mode, and the capillary voltage was set at 3,500 V. The spectrometer was scanned from m/z 50 to 1,000. Other conditions were the same as in the anion analysis[4].

Raw data obtained by CE-TOFMS were processed with the automatic integration software MasterHands[5]. Peak information including m/z, migration time (MT) and area was obtained. Peak area was converted to relative peak area according to the equation given below. Each peak was aligned according to similar migration time on CE and m/z value determined by TOFMS.

$$\text{Relative peak Area} = \text{Metabolite Peak Area}/(\text{Internal Standard Peak Area} \times \text{Sample Amount})$$

The metabolic pathway map was provided using public-domain software, VANTED: Visualisation and Analysis of Networks containing Experimental Data[6].

Drug metabolizing activity. Ketoprofen (15 mg/kg) was administered intravenously to the NOD/SCID mice into which hiPSC-LBs were transplanted through the cranial window (n=3). Sham-operated NOD/SCID mice were used as a control. Urine samples (0-2 hr) were collected in 0.5 M acetate buffer (pH 5.0). After adding 1 N KOH, the urine samples were incubated at 80° C. for 3 hours and then neutralized with an equal volume of 1 N HCl. After adding acetonitrile containing 1% acetic acid, the mixture was centrifuged (15000 rpm, 4° C., 5 min) The supernatant was subjected to liquid chromatograpy-tandem mass spectrometry (LC/MS/MS). LC-20A series (Shimadzu, Kyoto, Japan) equipped with Inertsil ODS-3 column (GL Sciences, Tokyo, Japan) was used for liquid chromatography (LC) experiments. Chromatographic separation was achieved on Inertsil ODS-3 column (5 μm, 4.6×150 mm I.D.; GL Sciences Inc., Tokyo, Japan). The column temperature was maintained at 40° C. A mobile phase consisting of 0.1% acetic acid (solvent A) and 0.1% acetic acid-containing acetonitrile (solvent B) was pumped in at a flow rate of 0.5 mL/min according to the following gradient schedule: a linear gradient from 25 to 80% solvent B (0-15 min), 80% solvent B (15-25 min), a linear gradient from 80 to 25% solvent B (25-26 min), and 25% solvent B (26-35 min). The LC was connected to a 4000 Q Trap system (AB SCIEX, Foster City, Calif.), and operated in negative electrospray ionization mode. The turbo gas was maintained at 600° C. Parent and/or fragment ions were filtered in the first quadrupole and dissociated in the collision cell using nitrogen as the collision gas. Ion spray voltage was set at −4500 V, and the analyzed m/z transitions (Q1/Q3) for ketoprofen and 1-hydroxyketoprofen were 253.1/209.3 and 269.1/209.3, respectively.

Debrisoquine (2 mg/kg) was orally administered to NOD/SCID mice transplanted with hiPSC-LB intracranially (n=3) and mesenterically (n=3). Sham-operated NOD/SCID mice were used as a control. Blood samples were collected 0.5, 1, 2 and 8 hours after administration, and heparin-Na was added. Plasma was centrifugally separated from blood.

Internal standard (niflumic acid 1 μM) and methanol solution (100 μL) were added to 5 μL of the plasma and centrifuged (15000 rpm, 4° C., 5 min). The supernatant was subjected to LC/MS/MS. An Acquity UltraPerformance LC system (Waters, Milford, Mass., USA) equipped with an Aquity UPLC BEH C18 column (Waters, Milford, Mass., USA) was used for LC experiments. Chromatographic separation was achieved on Acquity UPLC BEH C18 (1.7 μm, 2.1×50 mm I.D.; Waters, Milford, Mass., USA). The column temperature was maintained at 40° C. A mobile phase consisting of 10 mM ammonium acetate (solvent A) and acetonitrile (solvent B) was pumped in at a flow rate of 0.8 mL/min according to the following gradient schedule: 0% solvent B (0-0.2 min), a linear gradient from 0 to 30% solvent B (0.2-0.3 min), a linear gradient from 30 to 60% solvent B (0.3-0.85 min), 60% solvent B (0.85-1.15 min), a linear gradient from 60 to 100% solvent B (1.15-1.16 min), and 100% solvent B (1.16-1.5 min). The LC was connected to API4000 system (AB SCIEX, Foster City, Calif.) and operated in positive electrospray ionization mode. The turbo gas was maintained at 450° C. Parent and/or fragment ions were filtered in the first quadrupole and dissociated in the collision cell using nitrogen as the collision gas. Ion spray voltage was set at 5000 V and the analyzed m/z transitions (Q1/Q3) for 4-hyroxydebrisoquine and internal standard were 192.6/132.1 and 283.2/245.4, respectively.

Liver injury model. To evaluate the therapeutic potential of the transplantation strategy of the present inventors, Alb-TRECK/SCID mice were used for liver injury studies. Alb-TRECK/SCID mice were kindly provided by Hiromichi Yonekawa and Kunie Matsuoka (Tokyo Metropolitan Institute of Medical Science). This transgenic strain expresses HBEGF from ALB enhancer/promoter and develops fulminant hepatitis following administration of a small amount of diphtheria toxin (DT)[7]. hFLCs-LBs were transplanted into the mesentery covered with fibrin glue. At day 2 after transplantation, 1.5 µg/kg DT was infused via the tail vein to trigger severe liver injury. Survival was compared between transplanted and non-transplanted mice.

Supplementary Discussion
Feasibility of Cranial Window Model for Functional Liver Tissue Generation Detailed procedures for cranial window preparation were previously described[8]. The present inventors assessed the feasibility of cranial window to study liver cell maturation using transplants of EGFP-expressing E13.5 murine foetal liver cells (mFLCs). A section of mFLCs embedded in collagen/fibronectin gel was cut out and placed at the center of the cranial window. The window was then sealed with an 8-mm cover glass which was adhered to the bone using a histocompatible cyanoacrylate glue. Intravital fluorescence microscopy imaging showed a successful engrafting of transplanted mFLCs and a formation of functional vascular networks within the transplant (FIG. 21a). The transplanted tissue extensively differentiated into tissues resembling hepatic cords, sinusoids and bile ducts, all being characteristic of adult livers and not of donor E13.5 LBs (FIG. 21b). Liver tissue reconstitution by mFLCs was enhanced by addition of HGF and EGF, which are known to stimulate hepatic stem/progenitor cell expansion (FIG. 22)[9,10]. Thus, it was suggested that this transplantation approach provides a useful intravital monitoring system for evaluating LB cell maturation and differentiation.

Intravital Evaluation of Human Liver Cell Maturation

In the process of normal liver development, the morphology of liver cell changes from a round shape into a cobblestone-like shape[11]. This change can be easily visualized by cytokeratin immunostaining (FIG. 16a, left). Using IN Cell Investigator software, the present inventors have found that the roundness (form factor) of mouse liver cells decreases from 0.833±0.18 at E13.5 to 0.568±0.16 at postnatal week 8. Similarly, intravital imaging of single cell morphology revealed that the roundness of transplanted EGFP-labeled hFLCs changes from 0.93±0.07 at day 0 to 0.512±0.13 at day 30 post-transplantation (FIG. 27c, right). Consistent with these observations, enzyme-linked immunosorbent assay (ELISA) showed the occurrence of human albumin production at day 30 post-transplantation and thereafter (FIGS. 16c and d). Therefore, intravital monitoring of cell morphology can be an indicator for predicting the state of in vivo liver cell differentiation.

Detection of Human Specific-Drug Metabolism

The present inventors assessed the human specific-drug metabolism function using ketoprofen (KTP). KTP is primarily metabolized by cytochrome P450s in mice to produce 1-hydroxyketoprofen (OH-KTP)[12], while in humans KTP is mainly metabolized by UDP-glucuronosyltransferase (UGT) to produce ketoprofen glucuronide (KTP-G)[13].

Liver-humanized mice are a useful tool for studying human specific-drug metabolism. The human specific-drug metabolism function in liver-humanized mice was previously reported using high quality adult hepatocytes and immunodeficient mice bearing severely damaged liver. It was observed that UGT facilitated KTP glucuronidation after administration of KTP and that KTP was metabolized to KTP-G by hydrolysis. The KTP/OH-KTP peak area ratio was calculated and compared between hydrolysis and non-hydrolysis samples. The fold increase of the KTP/OH-KTP peak area ratio suggests the formation of KTP-G in samples. The fold increases in the urine of NOD/SCID mice with transplanted hiPSC-LBs and control mice were 11.8±5.2 and 2.3±0.7, respectively, suggesting that KTP glucuronidation (a human specific-drug metabolism function) was observed in hiPSC-LBs-transplanted NOD/SCID mice.

Debrisoquine, which serves as a common phenotyping reagent for human CYP2D6, is metabolized to 4-hydroxydebrisoquine (4-OHDB) in humans but negligible in mice. Importantly, human CYP2D6 is involved in the metabolism of 25% of known drugs and, due to its high number of polymorphisms, contributes to pronounced inter-individual variability. Following the oral administration of debrisoquine, the plasma concentration of 4-OHDB in the mesenterically or cranially transplanted group is higher than that in the sham-operated group, reflecting the production of a human specific-drug metabolite.

Establishment of Mesenteric Transplantation Model of hFLC- or hiPSC-LB Towards Clinical Application Cranial window model is not a very efficient method for organ bud transplantation because it is highly invasive. Therefore, if clinical application is assumed, development of a less invasive transplantation method is necessary. In addition, the transplantable volume is not sufficient to reverse hepatic failure. Hence, the present inventors attempted to examine the possibility of a minimally invasive mesenteric transplantation model with clinical relevance because portal blood flow was considered to be important for improvement of hepatic functions. Consistent with the expectations of the present inventors, a recent report showed that the intraperitoneal site could support human adult hepatocyte engraftment and maintenance of hepatic functions, presumably due to host vessel recruitment from mesenteric blood flow[15]. In vitro-grown hFLC-LBs or hiPSC-LBs were transplanted on the mesentery (FIG. 33a).

Stimulation by ⅔ Partial Hepatectomy

To determine whether hepatic cell maturation in hiPSC-LB transplant can be promoted by regenerative factors such as HGF, ⅔ partial hepatectomy (PH) was performed at day 7 post mesenteric transplantation. Following the ⅔ PH, production of human albumin was elevated to 121 ng/ml in the ⅔ PH group from 82.1 ng/ml in a sham-operated group at day 30 post surgery (FIG. 33c). These results suggested that hiPSC-Heps are capable of responding to regenerative stimuli after ⅔PH, presumably because of extensive hepatocyte proliferation and maturing in hiPSC-LB transplants.

Reversal of Liver Failure Using hFLC-LB Mesenteric Transplantation

To evaluate the therapeutic potential of the present inventors' strategy, in vitro-grown hFLC-LBs were transplanted on the mesentery sealed with fibrin glues. As a liver injury model, transgenic immunodeficient mice expressing human HB-EGF precursor under the control of a liver cell-specific albumin promoter were used. These mice, called toxin receptor-mediated cell knockout/severe combined immunodeficient (TRECK/SCID) mice, develop fulminant hepatitis upon administration of a small amount of diphtheria toxin (DT)[7]. DT agent was infused via tail vein at a dose of 1.5 µg/kg at day 2 post-transplantation. Survival curves revealed that all of the TRECK/SCID mice without transplantation died within 10 days. In contrast, 28% of the hFLC-LB transplanted TRECK/SCID mice survived for more than 40 days, indicating the therapeutic potential of the inventors' proof-of-concept (FIG. 32d). However, though this transplant model worked to some extent, it does not achieve a high rescue rate because DT is also toxic to human cells. Therefore, the present inventors adopted a TK-NOG mouse as immunodeficient liver injury model because administration of GCV, which is not toxic to human tissues, induces tissue-specific removal of transgenic liver parenchymal cells at appropriate timing. In this model, the present inventors removed host liver cells at days 7 and 10 post-transplantation at which time transplants are likely to engraft successfully through formation of functional human vascular networks.

SUPPLEMENTARY REFERENCES

1 Crawford, L. W., Foley, J. F. & Elmore, S. A. Histology atlas of the developing mouse hepatobiliary system with emphasis on embryonic days 9.5-18.5. Toxicol Pathol 38, 872-906, (2010).
2 Can, A. & Balci, D. Isolation, culture, and characterization of human umbilical cord stroma-derived mesenchymal stem cells. Methods Mol Biol 698, 51-62, (2011).
3 Soga, T. & Heiger, D. N. Amino acid analysis by capillary electrophoresis electrospray ionization mass spectrometry. Anal Chem 72, 1236-1241, (2000).
4 Soga, T. et al. Analysis of nucleotides by pressure-assisted capillary electrophoresis-mass spectrometry using silanol mask technique. J Chromatogr A 1159, 125-133, (2007).
5 Sugimoto, M., Wong, D. T., Hirayama, A., Soga, T. & Tomita, M. Capillary electrophoresis mass spectrometry-based saliva metabolomics identified oral, breast and pancreatic cancer-specific profiles. Metabolomics 6, 78-95, (2010).
6 Junker, B. H., Klukas, C. & Schreiber, F. VANTED: a system for advanced data analysis and visualization in the context of biological networks. BMC Bioinformatics 7, 109, (2006).
7 Saito, M. et al. Diphtheria toxin receptor-mediated conditional and targeted cell ablation in transgenic mice. Nat Biotechnol 19, 746-750, (2001).
8 Yuan, F. et al. Vascular permeability and microcirculation of gliomas and mammary carcinomas transplanted in rat and mouse cranial windows. Cancer Res 54, 4564-4568, (1994).
9 Suzuki, A., Iwama, A., Miyashita, H., Nakauchi, H. & Taniguchi, H. Role for growth factors and extracellular matrix in controlling differentiation of prospectively isolated hepatic stem cells. Development 130, 2513-2524, (2003).
10 Suzuki, A. et al. Clonal identification and characterization of self-renewing pluripotent stem cells in the developing liver. J Cell Biol 156, 173-184, (2002).
11 Shiojiri, N. et al. Quantitative analysis of cell allocation during liver development, using the spf(ash)-heterozygous female mouse. Am J Pathol 156, 65-75, (2000).
12 Populaire, P. et al. [Biological behavior: serum levels, excretion and biotransformation of (3-benzoylphenyl)-2-propionic acid, or ketoprofen, in animals and men]. Ann Pharm Fr 31, 735-749, (1973).
13 Ishizaki, T. et al. Pharmacokinetics of ketoprofen following single oral, intramuscular and rectal doses and after repeated oral administration. Eur J Clin Pharmacol 18, 407-414, (1980).
14 Yamasaki, C. et al. In vitro evaluation of cytochrome P450 and glucuronidation activities in hepatocytes isolated from liver-humanized mice. Drug Metab Pharmacokinet 25, 539-550, (2010).
15 Chen, A. A. et al. Humanized mice with ectopic artificial liver tissues. Proc Natl Acad Sci USA 108, 11842-11847, (2011).

All publications, patents and patent applications cited herein are incorporated herein by reference in their entirety.

INDUSTRIAL APPLICABILITY

Tissues and organs prepared according to the method of the present invention can be used for drug discovery screening and the like. Therefore, the present invention is applicable to industries such as pharmaceutical industry.

The invention claimed is:
1. A method of preparing a liver organ bud, comprising culturing hepatocytes together with a vascular endothelial cell and a mesenchymal stem cell in a medium with no use of a scaffolding to form the liver organ bud, wherein the liver organ bud is a structure capable of differentiating into a liver organ through maturing, wherein the culturing excludes culturing mesenchymal cells in which none of CD133, CD271 and Nestin are expressed, and wherein the medium is a medium for culturing endothelial vascular cells, a medium for culturing organ cells, or a mixture of these two media, and wherein the culturing step has a culture ratio of the hepatocytes: the vascular endothelial cell:the mesenchymal stem cell of 10:10-5:2-1, wherein the culturing has a time period of 3 to 10 days and wherein the liver organ bud is at least 100 µm in size.
2. The method of claim 1, wherein the hepatocytes are induced pluripotent stem cell-derived cells.
3. The method of claim 2, wherein the induced pluripotent stem cells are derived from human.
4. The method of claim 1, wherein the vascular endothelial cell and hepatocytes are plated on a gel and cultured together with at least one cell and/or factor selected from the group consisting of mesenchymal stem cells, factors secreted from vascular endothelial cells, factors secreted from mesenchymal stem cells, and factors secreted as a result of the presence of both vascular endothelial cells and mesenchymal stem cells.
5. The method of claim 1, wherein the vascular endothelial cell is a differentiated cell.
6. The method of claim 1, wherein the vascular endothelial cell is an undifferentiated cell.
7. The method of claim 1, wherein the culturing step has a time period of 6 days.
8. The method of claim 1, wherein the liver organ bud is a three-dimensional structure.

9. The method of claim 1, wherein the mesenchymal stem cell is a human mesenchymal stem cell.

10. The method of claim 1, wherein the method excludes culturing the hepatocytes on a solubilized basement membrane preparation extracted from Engelbreth-Holm-Swarm (EHS) mouse sarcoma.

11. The method of claim 1, wherein the hepatocytes are isolated hepatocytes.

12. The method of claim 1, wherein the liver organ bud is at least 1 mm in size.

13. The method of claim 1, wherein the liver organ bud is at least 5 mm in size.

14. A method of preparing a liver organ bud, comprising culturing hepatocytes together with a vascular endothelial cell and a mesenchymal stem cell in a medium with no use of a scaffolding to form the liver organ bud, wherein the liver organ bud is a structure capable of differentiating into a liver organ through maturing, wherein the culturing excludes culturing mesenchymal cells that do not express CD133, and wherein the medium is a medium for culturing endothelial vascular cells, a medium for culturing organ cells, or a mixture of these two media, and wherein the culturing step has a culture ratio of the hepatocytes: the vascular endothelial cell:the mesenchymal stem cell of 10:10-5:2-1, wherein the culturing has a time period of 3 to 10 days and wherein the liver organ bud is at least 100 µm in size.

15. A method of preparing a liver organ bud, comprising culturing hepatocytes together with a vascular endothelial cell and a mesenchymal stem cell in a medium with no use of a scaffolding to form the liver organ bud, wherein the liver organ bud is a structure capable of differentiating into a liver organ through maturing, wherein the culturing excludes culturing mesenchymal cells that do not express CD271, and wherein the medium is a medium for culturing endothelial vascular cells, a medium for culturing organ cells, or a mixture of these two media, and wherein the culturing step has a culture ratio of the hepatocytes: the vascular endothelial cell:the mesenchymal stem cell of 10:10-5:2-1, wherein the culturing has a time period of 3 to 10 days and wherein the liver organ bud is at least 100 µm in size.

16. A method of preparing a liver organ bud, comprising culturing isolated hepatocytes together with a vascular endothelial cell and a mesenchymal stem cell in a medium with no use of a scaffolding to form the liver organ bud having at least 100 µm in size and is configured to be transplanted, wherein the liver organ bud is a structure capable of differentiating into a liver organ through maturing, wherein the culturing excludes culturing mesenchymal cells that do not express Nestin, and wherein the medium is a medium for culturing endothelial vascular cells, a medium for culturing organ cells, or a mixture of these two media, and wherein the culturing step has a culture ratio of the hepatocytes: the vascular endothelial cell:the mesenchymal stem cell of 10:10-5:24, wherein the culturing has a time period of 3 to 10 days.

* * * * *